(12) United States Patent
Young et al.

(10) Patent No.: US 9,033,931 B2
(45) Date of Patent: *May 19, 2015

(54) SUBCUTANEOUS VASCULAR ACCESS PORTS HAVING ATTACHMENT FEATURES

(71) Applicant: Vital Access Corporation, Salt Lake City, UT (US)

(72) Inventors: Nathaniel P. Young, Salt Lake City, UT (US); G. Doug Smith, Sandy, UT (US); Mark A. Crawford, Sandy, UT (US); Randall K. Jones, Murray, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/725,529

(22) Filed: Dec. 21, 2012

(65) Prior Publication Data

US 2013/0245550 A1 Sep. 19, 2013

Related U.S. Application Data

(63) Continuation of application No. 12/697,167, filed on Jan. 29, 2010, now Pat. No. 8,337,464.

(60) Provisional application No. 61/229,023, filed on Jul. 28, 2009, provisional application No. 61/148,372, filed on Jan. 29, 2009.

(51) Int. Cl.
| | |
|---|---|
| *A61M 5/00* | (2006.01) |
| *A61M 39/02* | (2006.01) |
| *A61B 17/00* | (2006.01) |
| *A61B 17/34* | (2006.01) |
| *A61M 1/36* | (2006.01) |
| *A61M 1/14* | (2006.01) |

(52) U.S. Cl.
CPC ........ *A61M 39/0208* (2013.01); *A61B 17/0057* (2013.01); *A61B 17/3423* (2013.01); *A61B 2017/3425* (2013.01); *A61M 1/3653* (2013.01); *A61M 1/14* (2013.01); *A61M 1/3659* (2014.02); *A61M 1/3661* (2014.02)

(58) Field of Classification Search
USPC .......... 604/20–22, 174, 175, 93.01, 115, 116, 604/288.01, 288.02, 288.03; 606/108, 153; 623/1.1, 1.23
See application file for complete search history.

(56) References Cited

U.S. PATENT DOCUMENTS

| | | | |
|---|---|---|---|
| 3,998,222 | A | 12/1976 | Shihata |
| 4,164,221 | A | 8/1979 | Bentley |

(Continued)

FOREIGN PATENT DOCUMENTS

| | | |
|---|---|---|
| JP | 53-95592 U | 1/1952 |
| WO | WO 2007/109164 A2 | 9/2007 |

(Continued)

OTHER PUBLICATIONS

Brunette et al., 'Titanium in Medicine: Material Science, Surface Science, Engineering, Biological Responses and Medical Applications', Berlin; Springer, 2001, Isbn 3-540-66936-1, p727.

(Continued)

*Primary Examiner* — Laura Bouchelle
(74) *Attorney, Agent, or Firm* — Stoel Rives LLP

(57) ABSTRACT

Ports for accessing a vessels within a patient include passageways that can guide needles or other access devices directly into the vessels. The ports can be implanted subcutaneously within a patient. Some ports may be used in the creation and use of vascular access buttonholes.

21 Claims, 57 Drawing Sheets

(56) References Cited

U.S. PATENT DOCUMENTS

| | | |
|---|---|---|
| 4,318,401 A | 3/1982 | Zimmerman |
| 4,405,319 A | 9/1983 | Cosentino |
| 4,423,730 A | 1/1984 | Gabbay |
| 4,484,912 A | 11/1984 | Raible |
| 4,559,033 A | 12/1985 | Stephen et al. |
| 4,667,673 A | 5/1987 | Li |
| 4,781,695 A | 11/1988 | Dalton |
| 4,822,341 A | 4/1989 | Colone |
| 5,092,849 A | 3/1992 | Sampson |
| 5,127,412 A | 7/1992 | Cosmetto et al. |
| 5,222,963 A | 6/1993 | Brinkerhoff et al. |
| 5,222,974 A | 6/1993 | Kensey et al. |
| 5,263,930 A | 11/1993 | Ensminger |
| 5,275,322 A | 1/1994 | Brinkerhoff et al. |
| 5,281,199 A | 1/1994 | Ensminger et al. |
| 5,282,827 A | 2/1994 | Kensey et al. |
| 5,306,254 A | 4/1994 | Nash et al. |
| 5,334,217 A | 8/1994 | Das |
| 5,350,360 A | 9/1994 | Ensminger |
| 5,356,381 A | 10/1994 | Ensminger et al. |
| 5,441,517 A | 8/1995 | Kensey et al. |
| 5,527,277 A | 6/1996 | Ensminger et al. |
| 5,540,715 A | 7/1996 | Katsaros et al. |
| 5,662,616 A | 9/1997 | Bousquet |
| 5,676,689 A | 10/1997 | Kensey et al. |
| 5,707,393 A | 1/1998 | Kensey et al. |
| 5,741,228 A | 4/1998 | Lambrecht et al. |
| 5,792,104 A | 8/1998 | Speckman et al. |
| 5,817,113 A | 10/1998 | Gifford et al. |
| 5,848,989 A | 12/1998 | Villani |
| 5,861,004 A | 1/1999 | Kensey et al. |
| 5,882,341 A | 3/1999 | Bousquet |
| 5,989,213 A | 11/1999 | Maginot |
| 6,004,301 A | 12/1999 | Carter |
| 6,004,341 A | 12/1999 | Zhu et al. |
| 6,007,563 A | 12/1999 | Nash et al. |
| 6,007,576 A | 12/1999 | McClellan |
| 6,090,130 A | 7/2000 | Nash et al. |
| 6,099,508 A | 8/2000 | Bousquet |
| 6,156,016 A | 12/2000 | Maginot |
| 6,190,371 B1 | 2/2001 | Maginot et al. |
| 6,213,973 B1 | 4/2001 | Eliasen et al. |
| 6,261,255 B1 | 7/2001 | Mullis et al. |
| 6,261,257 B1 | 7/2001 | Uflacker et al. |
| 6,287,322 B1 | 9/2001 | Zhu et al. |
| 6,355,020 B1 | 3/2002 | Bousquet |
| 6,425,901 B1 | 7/2002 | Zhu et al. |
| 6,475,207 B1 | 11/2002 | Maginot et al. |
| 6,508,790 B1 | 1/2003 | Lawrence |
| 6,524,326 B1 | 2/2003 | Zhu et al. |
| 6,527,754 B1 | 3/2003 | Tallarida et al. |
| 6,544,206 B1 | 4/2003 | Johnston, Jr. |
| 6,585,705 B1 | 7/2003 | Maginot et al. |
| 6,595,941 B1 | 7/2003 | Blatter |
| 6,626,921 B2 | 9/2003 | Blatter et al. |
| 6,656,151 B1 | 12/2003 | Blatter |
| 6,682,489 B2 | 1/2004 | Tenerz et al. |
| 6,723,084 B1 | 4/2004 | Maginot et al. |
| 6,726,704 B1 | 4/2004 | Loshakove et al. |
| 6,726,711 B1 | 4/2004 | Langenbach et al. |
| 6,743,218 B2 | 6/2004 | Maginot et al. |
| 6,764,500 B1 | 7/2004 | Muijs Van De Moer et al. |
| 6,913,609 B2 | 7/2005 | Yencho |
| 6,960,185 B2 | 11/2005 | Adaniya et al. |
| 6,964,675 B2 | 11/2005 | Zhu et al. |
| 6,979,338 B1 | 12/2005 | Loshakove et al. |
| 6,997,914 B2 | 2/2006 | Smith et al. |
| 7,008,412 B2 | 3/2006 | Maginot |
| 7,022,131 B1 | 4/2006 | Derowe et al. |
| 7,025,741 B2 | 4/2006 | Cull |
| 7,044,916 B2 | 5/2006 | Tenerz et al. |
| 7,060,084 B1 | 6/2006 | Loshakove et al. |
| 7,063,711 B1 | 6/2006 | Loshakove et al. |
| 7,073,509 B2 | 7/2006 | Tenerz et al. |
| 7,118,546 B2 | 10/2006 | Blatter |
| 7,128,734 B1 | 10/2006 | Wilson et al. |
| 7,261,705 B2 | 8/2007 | Edoga et al. |
| 7,285,097 B2 | 10/2007 | Tenerz et al. |
| 7,331,981 B2 | 2/2008 | Cates et al. |
| 7,396,359 B1 | 7/2008 | Derowe et al. |
| 7,708,722 B2 | 5/2010 | Glenn |
| 7,828,781 B2 | 11/2010 | Edoga et al. |
| 7,909,804 B2 | 3/2011 | Stats |
| 8,034,064 B2 | 10/2011 | Blatter |
| 8,337,464 B2 | 12/2012 | Young et al. |
| 8,337,465 B2 | 12/2012 | Young et al. |
| 8,343,028 B2 | 1/2013 | Gregoric et al. |
| 8,409,228 B2 | 4/2013 | Blatter et al. |
| 8,574,204 B2 | 11/2013 | Bourne et al. |
| 8,668,706 B2 | 3/2014 | Blatter et al. |
| 8,690,816 B2 | 4/2014 | Dakin et al. |
| 2001/0007931 A1 | 7/2001 | Blatter |
| 2001/0037094 A1 | 11/2001 | Adaniya et al. |
| 2001/0056266 A1 | 12/2001 | Tallarida et al. |
| 2002/0087127 A1 | 7/2002 | Finch, Jr. et al. |
| 2003/0004520 A1 | 1/2003 | Haarala et al. |
| 2003/0023208 A1 | 1/2003 | Osypka et al. |
| 2003/0078597 A1 | 4/2003 | Blatter et al. |
| 2003/0089757 A1 | 5/2003 | Whitman |
| 2004/0097994 A1 | 5/2004 | Blatter |
| 2004/0133173 A1 | 7/2004 | Edoga et al. |
| 2004/0254537 A1 | 12/2004 | Conlon et al. |
| 2004/0260333 A1 | 12/2004 | Dubrul et al. |
| 2005/0171565 A1 | 8/2005 | Yencho et al. |
| 2005/0177176 A1 | 8/2005 | Gerbi et al. |
| 2005/0283188 A1 | 12/2005 | Loshakove et al. |
| 2006/0247605 A1 | 1/2006 | Loshakove et al. |
| 2007/0083156 A1 | 4/2007 | Muto et al. |
| 2007/0123811 A1 | 5/2007 | Squitieri |
| 2007/0265584 A1 | 11/2007 | Hickman et al. |
| 2008/0051811 A1 | 2/2008 | Blatter et al. |
| 2008/0086075 A1 | 4/2008 | Isik et al. |
| 2008/0086100 A1 | 4/2008 | Isaacson et al. |
| 2008/0147114 A1 | 6/2008 | Derowe et al. |
| 2008/0195124 A1 | 8/2008 | Borghi |
| 2008/0243080 A1 | 10/2008 | Chang |
| 2008/0249509 A1 | 10/2008 | Glenn |
| 2009/0076466 A1 | 3/2009 | Quebbemann et al. |
| 2009/0118683 A1 | 5/2009 | Hanson et al. |
| 2009/0192473 A1 | 7/2009 | Crocker et al. |
| 2009/0209918 A1 | 8/2009 | Berglund |
| 2010/0121358 A1 | 5/2010 | Blatter et al. |
| 2010/0152640 A1 | 6/2010 | Golding et al. |
| 2010/0152658 A1 | 6/2010 | Hanson et al. |
| 2010/0191166 A1 | 7/2010 | Phillips et al. |
| 2010/0191179 A1 | 7/2010 | Young et al. |
| 2010/0191191 A1 | 7/2010 | Young et al. |
| 2010/0274223 A1 | 12/2010 | Nugent et al. |
| 2010/0318016 A1 | 12/2010 | Nugent et al. |
| 2011/0184347 A1 | 7/2011 | Mason |
| 2011/0213309 A1 | 9/2011 | Young et al. |
| 2012/0245536 A1 | 9/2012 | Gerber et al. |
| 2013/0060200 A1 | 3/2013 | Dalton |
| 2013/0066282 A1 | 3/2013 | Dalton |
| 2013/0184725 A1 | 7/2013 | Blatter et al. |
| 2013/0245550 A1 | 9/2013 | Young et al. |
| 2013/0245572 A1 | 9/2013 | Young et al. |
| 2014/0163588 A1 | 2/2014 | Blatter et al. |
| 2014/0207086 A1 | 7/2014 | Stats et al. |

FOREIGN PATENT DOCUMENTS

| | | |
|---|---|---|
| WO | WO 2009/149474 | 12/2009 |
| WO | WO 2010/088532 | 8/2010 |
| WO | WO 2010/088541 | 8/2010 |
| WO | WO 2011/094712 | 8/2011 |

OTHER PUBLICATIONS

International Search Report and Written Opinion dated Jul. 31, 2009 for PCT/US2009/046684,.

International Preliminary Report dated Dec. 06, 2010 for PCT/US2009/046664.

(56) References Cited

OTHER PUBLICATIONS

International Search Report and Written Opinion dated Apr. 08, 2010 for PCT/US2010/022607,.
International Preliminary Report dated Aug. 11, 2011 for PCT/US2010/022607.
International Search Report and Written Opinion dated Apr. 08, 2010 for PCT/US2010/022622,.
International Preliminary Report dated Aug. 11, 2011 for PCT/US2010/022622.
International Search Report dated Mar. 25, 2011 for PCT/US2011/023228.
Preliminary Amendment dated 07/14;2010 for U.S. Application No. 12/697,190.
Second Preliminary Amendment dated Feb. 17,2011 for U.S. Appl. No. 12/697,190.
Preliminary Amendment dated Jul. 14, 2010 for U.S. Appl. No. 12/697,192.
Second Preliminary Amendment dated Feb. 17, 2011 for U.S. Appl. No. 12/697,192.
Office Action dated Feb. 1, 2012 for U.S. Appl. No. 12/480,678.
Office Action dated Sep. 13, 2011 for U.S. Appl. No. 12/697,190.
Preliminary Amendment dated Jan. 25, 2010 for U.S. Appl. No. 12/480,678.
Office Action dated Oct. 9, 2012 for U.S. Appl. No. 12/697,167.
Interview Summary dated Feb. 3, 2012 for U.S. Appl. No. 12/697,190.
Amendment and Response dated Mar. 13, 2012 for U.S. Appl. No. 12/697,190.
Amendment and Response dated Aug. 1, 2012 for U.S. Appl. No. 12/480,678.
Interview Summary dated Aug. 27, 2012 for U.S. Appl. No. 12/480,678.
Supplemental Amendment and Response dated Sep. 6, 2012 for U.S. Appl. No. 12/480,678.
Notice of Allowance dated Jul. 12, 2012 for U.S. Appl. No. 12/697,190.
Office Action dated Jun. 19, 2012 for U.S. Appl. No. 12/697,190.
Amendment After Final dated Jun. 21, 2012 for U.S. Appl. No. 12/697,190.
Office Action dated Feb. 26, 2013 for U.S. Appl. No. 12/697,192.
Office Action dated Aug. 29, 2013 for U.S. Appl. No. 12/697,192.
Notice of Allowance dated Nov. 29, 2012 for U.S. Appl. No. 12/480,678.
Notice of Allowance dated May 10, 2013 for U.S. Appl. No. 13/781,575.
Notice of Allowance dated Oct. 7, 2013 for U.S. Appl. No. 13/781,575.
Office Action dated Aug. 7, 2013 for U.S. Appl. No. 13/018,277.
Notice of Allowance dated Feb. 19, 2014 for U.S. Appl. No. 13/018,277.
International Preliminary Report on Patentability dated Jul. 31, 2012 in International Application No. PCT/US2011/023228.
Office Action dated Oct. 9, 2012 in U.S. Patent Appl. No. 12/697,192.
Amendment dated Dec. 11, 2012 in U.S. Appl. No. 12/697,192.
Interview Summary dated Dec. 18, 2012 in U.S. Appl. No. 12/697,192.
Office Action dated Feb. 26, 2013 in U.S. Appl. No. 12/697,192.
Amendment dated Jun. 25, 2013 in U.S. Appl. No. 12/697,192.
Office Action dated Mar. 28, 2014 in U.S. Appl. No. 12/697,192.
Amendment dated Sep. 29, 2014 in U.S. Appl. No. 12/697,192.
Notice of Allowance dated Nov. 13, 2014 in U.S. Appl. No. 12/697,192.
Notice of Allowance dated Jun. 3, 2014 in U.S. Appl. No. 13/018,277.
Notice of Allowance dated Sep. 18, 2014 in U.S. Appl. No. 13/018,277.
Extended European Search Report that issued on Jul. 2, 2014 in European Application No. 11737838.0.

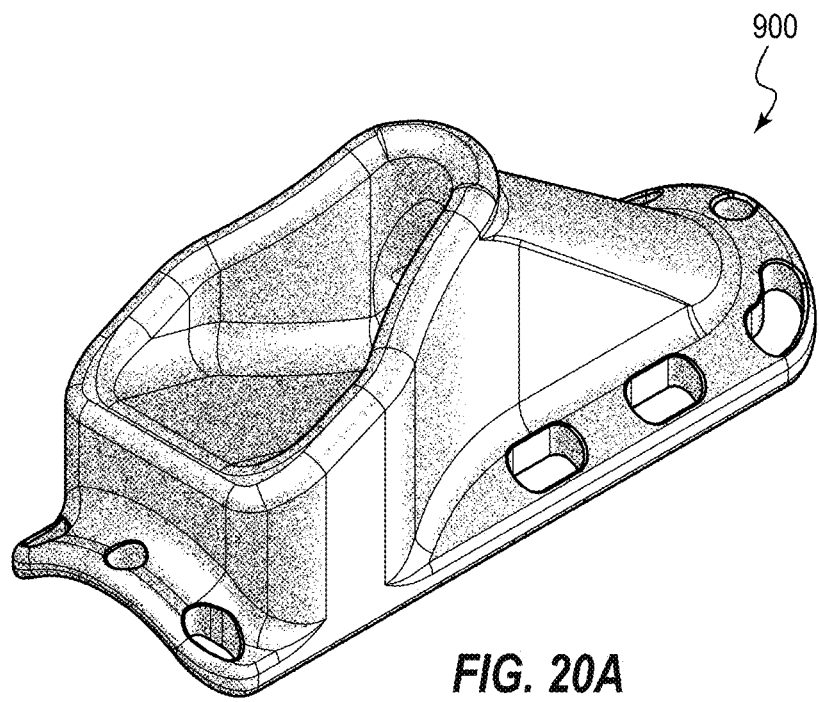
FIG. 20A
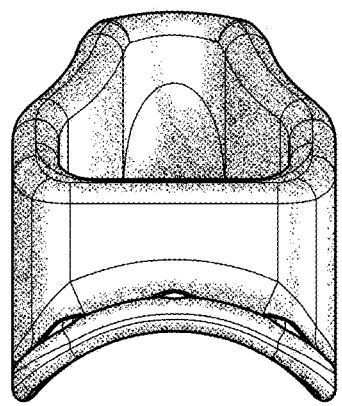 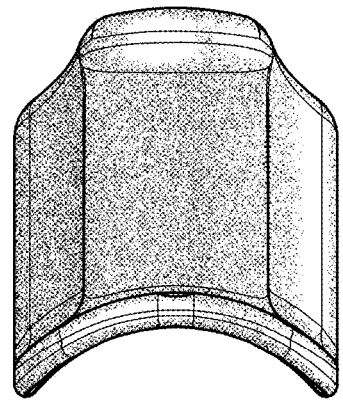
FIG. 20B    FIG. 20C

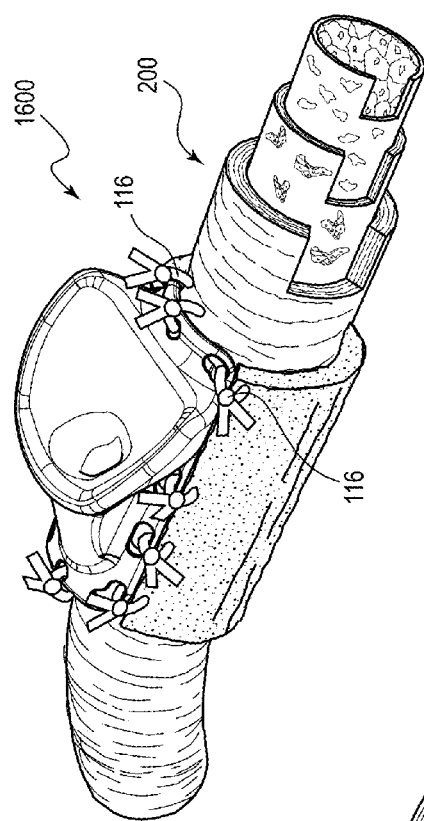
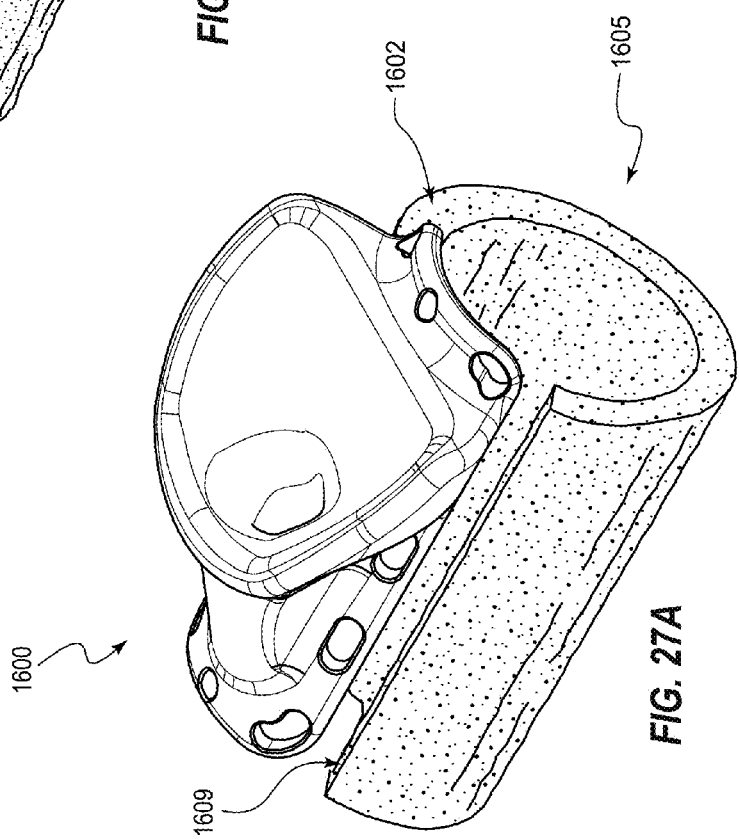
FIG. 27B
FIG. 27A

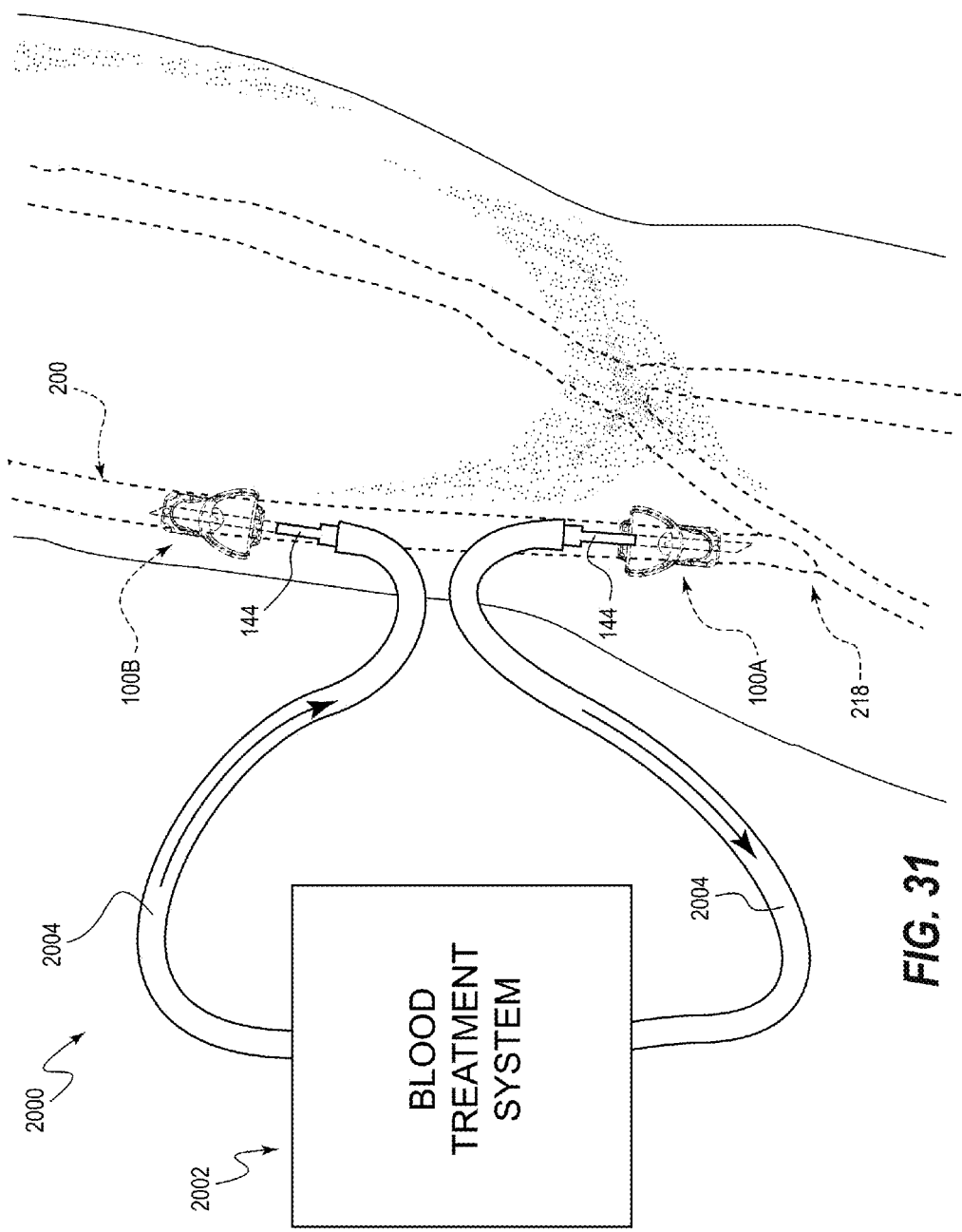

SUBCUTANEOUS VASCULAR ACCESS PORTS HAVING ATTACHMENT FEATURES

CROSS-REFERENCE TO RELATED APPLICATIONS

This application is a continuation of U.S. patent application Ser. No. 12/697,167, titled VASCULAR ACCESS PORTS AND RELATED METHODS, filed on Jan. 29, 2010, which claims the benefit under 35 U.S.C. §119(e) of U.S. Provisional Patent Application No. 61/148,372, titled VASCULAR ACCESS METHODS, APPARATUS AND SYSTEMS, filed on Jan. 29, 2009, and of U.S. Provisional Patent Application No. 61/229,023, titled SURGICALLY IMPLANTED DIRECT VASCULAR ACCESS PORT METHOD AND APPARATUS, filed on Jul. 28, 2009, the entire contents of each of which are hereby incorporated by reference herein.

STATEMENT REGARDING FEDERALLY SPONSORED RESEARCH OR DEVELOPMENT

The invention was made with support from the U.S. Government under Grant No. SBIR R44 CA 139608, which was awarded by the National Institutes of Health. The U.S. Government has certain rights in the invention.

TECHNICAL FIELD

The present disclosure relates to subcutaneous vascular access ports and related systems and methods.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 20A is a perspective view of another embodiment of a vascular access port;
FIG. 20B is a rear elevation view thereof;
FIG. 20C is a front elevation view thereof;
FIG. 27A is a perspective view of another embodiment of a vascular access port;
FIG. 27B is a perspective view of the vascular access port of FIG. 27A coupled to a vessel;
FIG. 31 is a perspective view of an embodiment of a vascular access system that can be used for the external treatment of blood.

DETAILED DESCRIPTION

Figure 1:
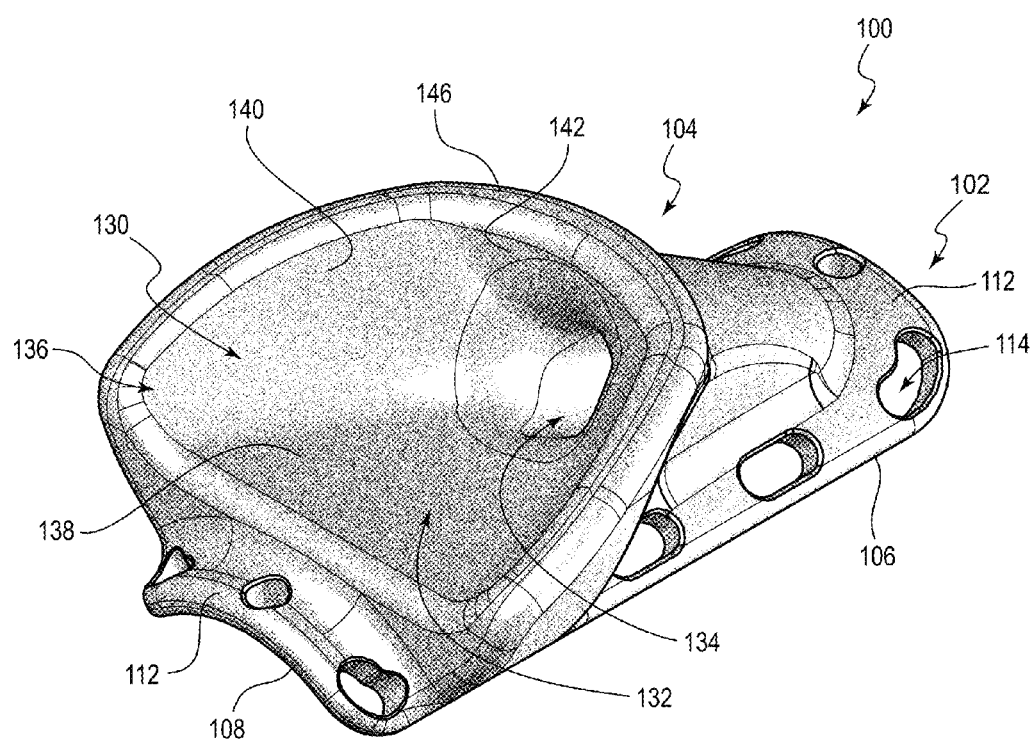
FIG. 1 is a perspective view of an embodiment of a vascular access port.
Figure 2:
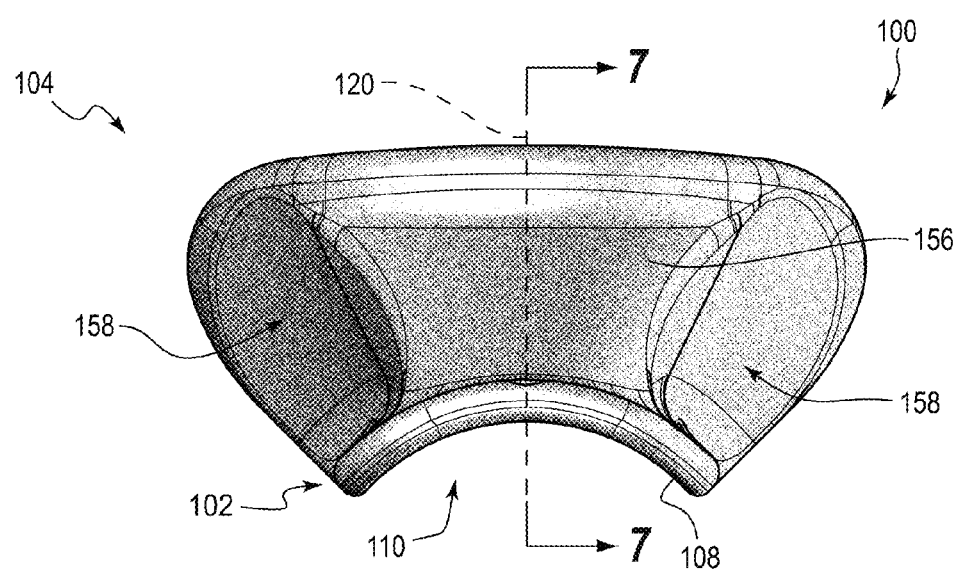
FIG. 2 is a front elevation view thereof.

Certain embodiments of vascular access ports described herein are configured to be implanted subcutaneously in a patient for relatively long or indefinite periods. The vascular access ports can be implanted in any suitable manner and can be substantially fixed relative to a vessel wall once implanted. For example, in some implantation methods, a bottom surface of a vascular access port placed in contact with the tunica adventitia of a vessel and the port is secured to the vessel via one or more sutures that extend through at least a portion of every layer of the vessel. In further embodiments, a portion of the tunica adventitia is separated or removed from a blood vessel such that the bottom surface of a port is relatively close to the tunica media layer of the blood vessel, and the port is secured to the vessel via one or more sutures that extend through at least a portion of the tunica adventitia layer and substantially entirely through the media and the tunica intima layers. The surface of the port that contacts the vessel wall can comprise an opening through which an access device, such as a needle, can be inserted into a lumen of the blood vessel. The vascular access ports can be well-suited for buttonhole cannulation techniques in which buttonhole access sites are created in vessel walls and/or are used to access the vessels. The term "buttonhole" is used herein in its ordinary sense in the field of vascular access (e.g., in the field of hemodialysis), particularly in the context of cannulation techniques, and the term can include single-site cannulation holes that are approximately the same size as access devices that are inserted therethrough (e.g., needles or other cannulation devices), and that can permit relatively easy insertion of the access devices as compared with other areas along a vessel wall. Similarly, the ports can be well-suited for the creation and/or use of tracts through the skin of a patient through which the buttonholes can be repeatedly accessed. These and other features and advantages of various embodiments of vascular access ports, of systems that employ the ports, and of methods of implanting and using the ports will be apparent from the disclosure herein.

FIGS. 1-7 illustrate an embodiment of a vascular access port 100. The vascular access port 100 includes a base 102 and a body 104. In the illustrated embodiment, the base 102 and the body 104 are integrally formed as a unitary piece, and the body 104 extends away from the base 102. The base 102 is elongated in a longitudinal direction. In particular, the illustrated base 102 defines a substantially rectangular perimeter 106 that extends a greater distance in a longitudinal direction than it does in a transverse direction (see, e.g., FIG. 5). The edges and corners of the rectangular perimeter 106 can be rounded, which can prevent trauma to surrounding tissue when the vascular access port 100 is implanted.

The base 102 can include a base surface or bottom surface 108 that is configured to face a vessel when the vascular access port 100 is coupled to the vessel. The bottom surface 108 can be configured to conform to a contour of a wall of the vessel. For example, the bottom surface 108 of the base 102 can be bowed in the transverse direction and can have a radius of curvature that is substantially the same as a radius of curvature of an outer surface of a vessel to which the vascular access port 100 is to be attached. The bowed bottom surface 108 can define a cavity 110 (see FIGS. 2 and 3) into which at least a portion of a circumference of a vessel can be received. In the illustrated embodiment, the width and the curvature of the bottom surface 108 are such that the cavity 110 is sized to receive a substantial portion of the circumference of a vessel therein. Such a configuration can permit the bottom surface 108 to form a stable contact with the vessel. Other suitable arrangements are also possible, as discussed below.

The base 102 can include one or more connection flanges 112 that extend about a least a portion of a periphery of the base 102. In the illustrated embodiment, a first connection flange 112 extends about a front end of the base 102 and a second connection flange 112 is at a back end of the base 102. One or more attachment channels or attachment passages 114 can extend through the connection flanges 112. The attachment passages 114 can be configured to permit one or more ties or attachment devices 116 to extend therethrough so as to attach the vascular access port 100 to a vessel (see, e.g., FIGS. 8, 9C, 10F, 11A, and 12), as discussed further below. Any suitable attachment devices 116 may be used, such as one or more sutures, pinch rings, hooks, or wires. Accordingly, in some embodiments, one or more of the attachment passages 114 may be referred to as suture holes. As further discussed below, in the illustrated embodiment, the base 102 includes a centrally situated attachment passage 114 at each of the front and rearward ends thereof.

Figure 3:
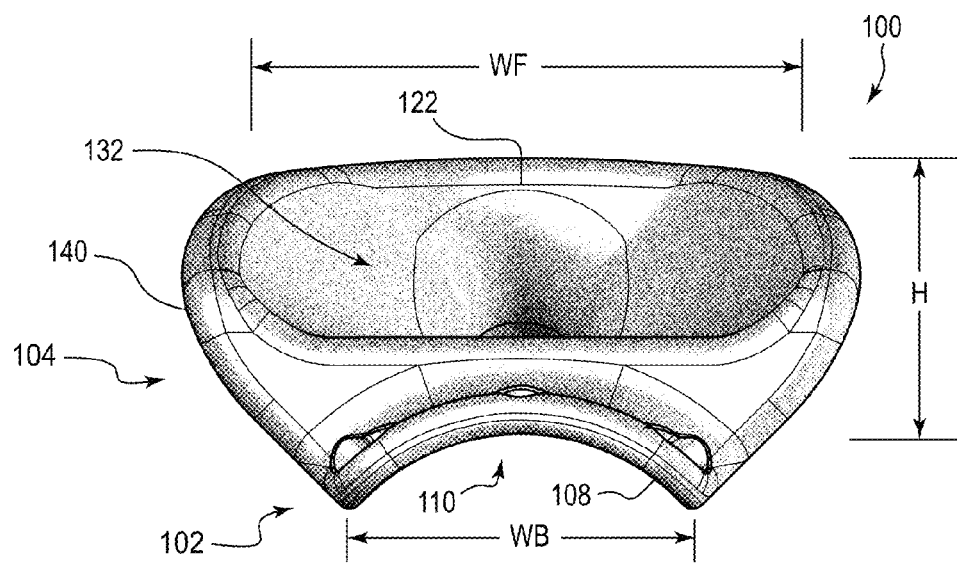
FIG. 3 is a rear elevation view thereof.
Figure 4:
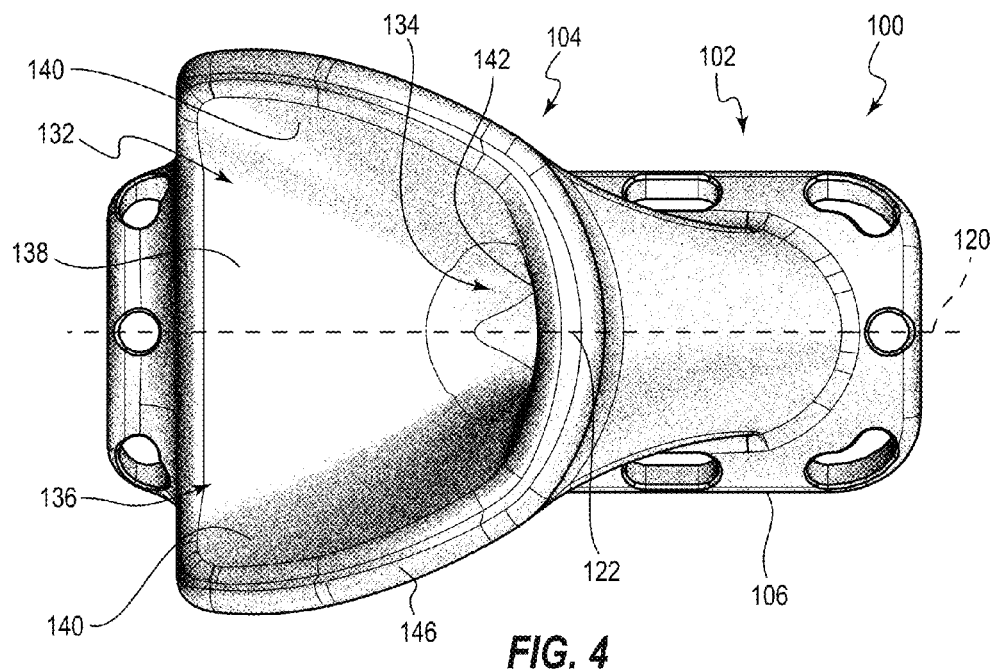
FIG. 4 is a top plan view thereof.
Figure 6:
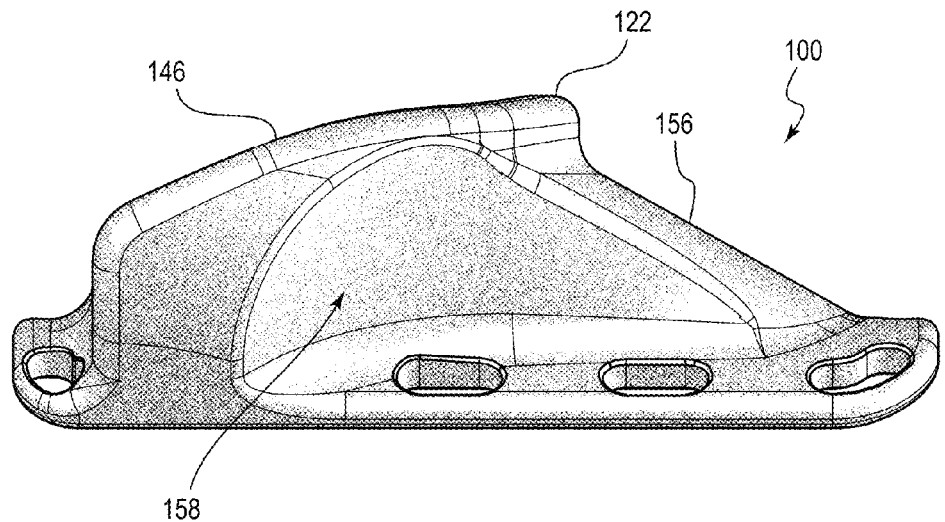
FIG. 6 is a right side elevation view thereof, wherein a left side elevation view is a mirror image of the right side elevation view.

The body 104 can extend upwardly from the base 102. In the illustrated embodiment, the body rises upwardly along a central vertical longitudinal plane 120 (see FIGS. 2 and 4) of the vascular access port 100. With reference to FIG. 4, the body 104 can expand outwardly from the central vertical longitudinal plane 120 and can widen in a rearward direction. Additionally, as shown in FIGS. 3, 4, and 6, a pinnacle region 122 of the body 104 can be positioned along the central vertical longitudinal plane 120 and at approximately a longitudinal center of the body 104. It is noted that directional terms, such as bottom, front, and rearward, are used relative to the orientation of the vascular access port 100 shown in FIG. 1. Such directional terms are not intended to limit the possible orientations of the vascular access port 100 within a patient. For example, in some embodiments, the front end of the vascular access port 100 may be oriented upstream from the rearward end thereof when the port 100 is coupled to a vessel, whereas in other embodiments, the front end may be oriented downstream from the rearward end.

Figure 5:
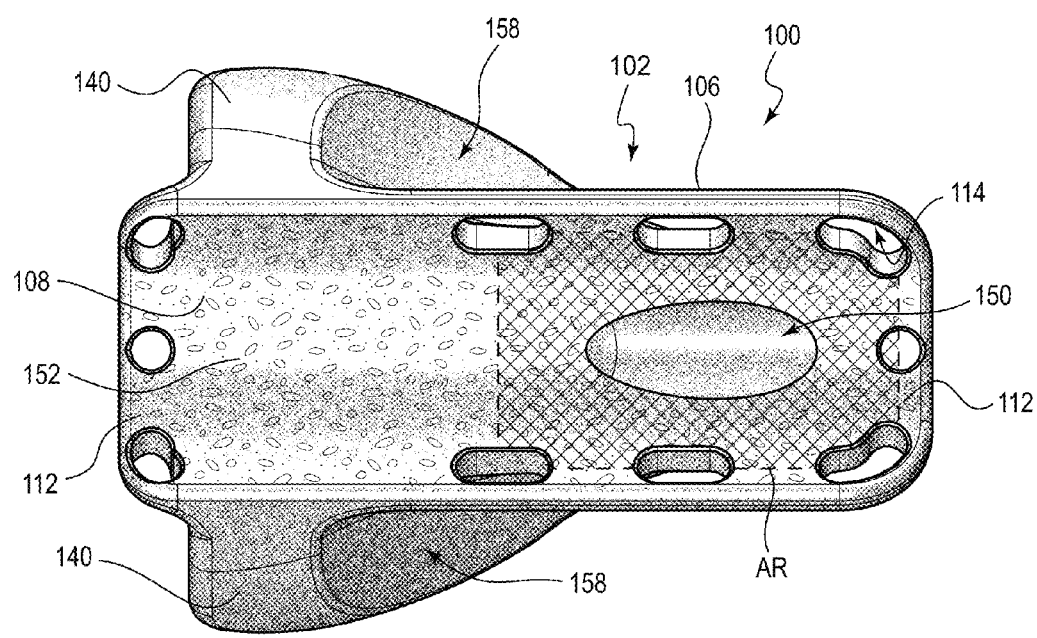
FIG. 5 is a bottom plan view thereof.
Figure 7:
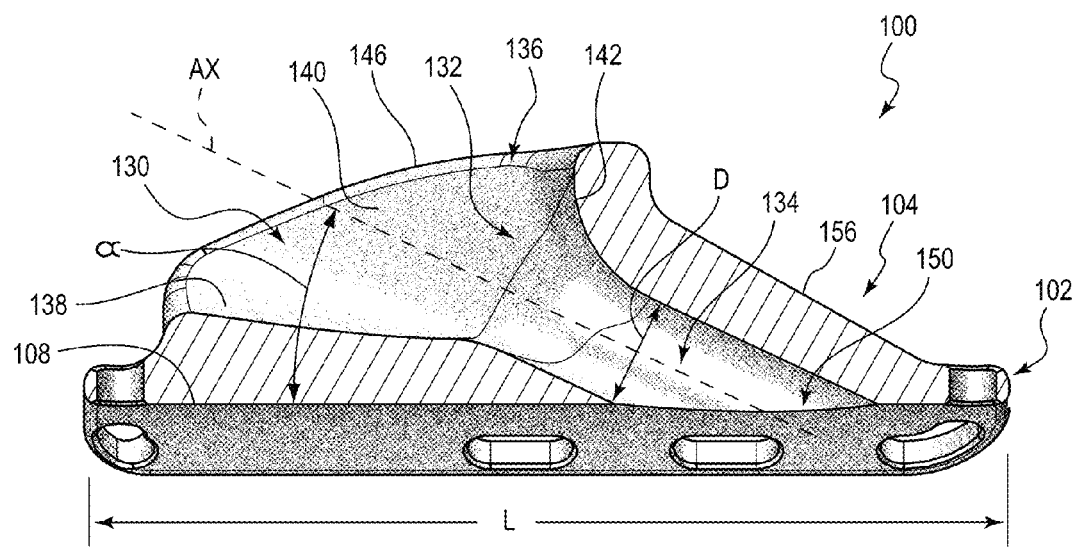
FIG. 7 is a cross-sectional view of the vascular access port of FIG. 1 taken along the view line 7-7 in FIG. 2.

A guidance passageway 130 can extend through the body 104. In the illustrated embodiment, the guidance passageway 130 includes a funnel region 132 and a channel 134. The funnel region 132 defines a relatively large entry mouth 136, which extends about or circumscribes the proximal end or proximal opening thereof, and the funnel region 132 narrows from the entry mouth 136 in a forward and downward direction. In the illustrated embodiment, a forward end of the funnel region 132 transitions into the channel 134. The funnel region 132 can include a base surface 138 that projects rearwardly from the channel 134 and that flares outwardly in the rearward direction. As shown in FIG. 7, the base surface 138 of the funnel region 132 can be angled upwardly (in a rearward direction) relative to the bottom surface 108 of the base 102. The funnel region 132 can further include wings 140 that each curve upwardly and outwardly from the base surface 138 and that are each joined to a backstop portion 142 at a forward end thereof. As shown in FIGS. 4 and 5, the wings 140 can extend outwardly past the perimeter 106 of the base 102 so as to provide for a wide entry mouth 136 of the funnel region 132. The backstop portion 142 can rise upwardly from an upper surface of the channel 134 and may include a surface that is directed substantially vertically. The backstop portion 142 can span the channel 134, and at least a portion thereof can be positioned directly above the channel 134.

The funnel region 132 can fully encompass an entrance end of the channel 134 and can encourage a tip of an access device 144, such as a needle (see FIG. 11B), to enter the channel 134. The funnel region 132 thus can serve as an enlarged target area that can assist in directing an access device 144 to a desired portion of a vessel, as discussed further below. The funnel region 132 can comprise a material that can prevent or discourage a tip of an access device 144 from embedding therein or removing a portion thereof as the tip moves toward the channel 134. For example, in various embodiments, the funnel region 132 can comprise titanium, stainless steel, a rigid plastic, or a similar material.

At least a portion of the entry mouth 136 of the funnel region 132 can include a palpation projection 146, such as a palpation ridge. In the illustrated embodiment, the palpation projection 146 is substantially U-shaped and extends over the wings 140 and the backstop portion 142 of the funnel region 132, and the pinnacle region 122 of the body 104 is located at a forward end of the palpation projection 146. The palpation projection 146 can be rounded or radiused so as to be free from sharp edges that could lead to tissue erosion. As further discussed below, the palpation projection 146 can be used to locate the vascular access port 100 and/or confirm an orientation thereof when the port 100 is positioned subcutaneously in a patient.

The entry mouth 136 of the funnel region 132 may be used to assist in achieving hemostasis after removal of an access device 144 from the vascular access port 100. To this end, the palpation projection 146 may substantially define a plane, in some embodiments. As shown in FIG. 6, the palpation projection 146 of the illustrated embodiment is nearly or substantially planar, as it is not perfectly planar due to a slight curvature in the longitudinal direction. The palpation projection 146 also exhibits a slight curvature in the transverse direction, as can be seen in FIG. 3. Moreover, in the illustrated embodiment, a rearward edge of the entry mouth 136 smoothly transitions into the palpation projection 146 at either end thereof and is only slightly below the substantially planar region defined by the palpation projection 146. Accordingly, as further discussed below, a seal can readily be formed about a periphery of the entry mouth 136 of an implanted vascular access port 100 by pressing tissue that surrounds the port 100 against the entry mouth 136.

With reference to FIG. 7, the channel 134 can extend through the base 102, and a bottom end of the channel 134 can define an opening 150 in the bottom surface 108 of the base 102. The opening 150 may be referred to as a distal opening 150 of the guidance passageway 130. The channel 134 can be configured to constrain movement of one or more access devices 144 inserted individually therethrough along a predetermined or repeatable path toward the opening 150. Accordingly, when the vascular access device 100 is fixed relative to a vessel, the channel 134 and the opening 150 can cause the one or more access devices 144 to cannulate the same portion of the vessel. In certain embodiments, the channel 134 defines a substantially constant inner diameter D along a length thereof, which can constrain the movement of an access device 144 that has an outer diameter that is slightly smaller than the diameter D. For example, in the illustrated embodiment, the channel 134 is substantially cylindrical and can constrain movement of a substantially cylindrical access device 144 (e.g., a fistula needle) that has an outer diameter slightly smaller than the diameter D (see FIG. 11B). The diameter D and/or the length of the channel 134 can be selected to achieve a desired amount of constraint for a given access device 144.

With continued reference to FIG. 7, the channel 134 can define a central axis AX, which can define an acute angle $\alpha$ relative to the bottom surface 108. For example, in the illustrated embodiment, the axis AX and a longitudinal line along the bottom surface 108 form the angle $\alpha$. In FIG. 7, the longitudinal line is represented in FIG. 7 by a line L that defines a longitudinal length of the base 10. When the vascular access port 100 is connected to a vessel, the longitudinal line L can be substantially parallel to a longitudinal axis of a lumen of the vessel (see FIG. 11A). Accordingly, in the illustrated embodiment, the channel 134 can constrain movement of an access device 144 along a path that is both nonparallel and non-orthogonal to the lumen of the vessel. In particular, the channel 134 can constrain movement of the access device 144 along a path that is at or is approximately at the angle $\alpha$ relative to the lumen of the vessel. In various embodiments, the angle $\alpha$ can have a value that is no greater than about 15, 20, 25, 30, 35, 45, or 60 degrees; can have a value that is no less than about 10, 15, 20, 25, 30, 35, 45, or 60 degrees; or can have a value that is within a range of from about 30 degrees to about 60 degrees, from about 15 degrees to about 45 degrees, or from about 20 degrees to about 35 degrees. As further discussed below, some protocols for the creation and use of buttonhole cannulation sites can require introduction of a needle into a vessel at a designated acute angle. Accordingly, certain embodiments of the vascular access port 100 can be configured for use with such protocols, and the angle $\alpha$ can be selected to correspond with the angle designated by the protocol.

As previously discussed, the diameter D defined by the channel 134 can be larger than a diameter of an access device 144 that is inserted through the channel 134. In some embodiments, the channel 134 is larger than the access device 144 by a sufficient amount to allow the access device 144 to pass through it easily or with little or no resistance. Reduction or elimination of insertion and removal forces between an access device 144 and the channel 134 can assist in maintaining a secure attachment between the vascular access port 100 and a vessel over the course of multiple insertion and removal events. Moreover, in the illustrated embodiment, the channel 134 is open, unobstructed, clear, free, or vacant. Stated otherwise, the channel 134 is devoid of closure apparatus, such as, for example, septums, valves, obturators, etc., which could be used to selectively open the channel 134 prior to or during insertion of an access device 144 therein, or which could be used to selectively close the channel 134 during or after removal of an access device 144 therefrom. The term "closure apparatus," as used herein, is directed to mechanical, electromechanical, or other synthetic, foreign, or non-native devices or systems that may be manufactured outside of a patient and introduced into a patient, but does not include natural or patient-generated materials that may close the channel 134, such as, for example, clotted blood, tissue ingrowth, or vascular structures, such as a neointima or a pseudo vessel wall.

In certain embodiments, a configuration of the channel 134, or more generally, the guidance passageway 130, can remain unchanged upon insertion of an access device 144 therein or removal of an access device 144 therefrom, which may result, at least in part, from an absence of closure apparatus within the channel 134 or the guidance passageway 130. More generally, a configuration of the vascular access port 100 can remain unchanged upon insertion of an access device 144 therein or removal of an access device 144 therefrom. Stated otherwise, in certain embodiments, no portion of one or more of the channel 134, the guidance passageway 130, and the vascular access port 100 may be deformed, rotated, translated, pivoted, expanded, contracted, or otherwise moved relative to remaining portions of one or more of the channel 134, the guidance passageway 130, and the vascular access port 100. Any resistive forces to the insertion or removal of an access device 144 that might be provided by closure apparatus thus are absent during use of the vascular access port 100. Methods by which hemostasis may be achieved via the vascular access port 100 in the absence of closure apparatus are discussed below.

Manufacture of embodiments of the vascular access port 100 can be facilitated by their lack of closure apparatus. For example, in the illustrated embodiment, the vascular access port 100 comprises a unitary piece and/or comprises a single material, and it is devoid of moving parts. Likewise, in the illustrated embodiment, the guidance passageway 130 is defined by a single unitary piece and/or by a single material, and it is devoid of moving parts. Other or further embodiments may comprise multiple parts that are fixedly attached to each other in a non-separable fashion. Embodiments of the vascular access port 100 can be manufactured via any suitable method, such as machining, die casting, injection molding, etc., and may comprise any suitable biocompatible material, such as, for example, titanium, stainless steel, rigid plastic, etc. In some embodiments, the vascular access port 100 comprises a resorbable material. For example, in various embodiments, the vascular access port 100 can comprise one or more of caprilactone and glycolide (e.g., Panacryl, in proportions of about 90% and 10%, respectively); ε-caprolactone; cellulose; ethylene oxide with propylene oxide (e.g., Pleuronic F-108); ethylene oxide with block polymer (e.g., DynaGraft proloxamer); glycolide, dioxanone, and trimethylene carbonate (e.g., Biosyn, in proportions of about 60%, 14%, and 26%, respectively); glycolide and ε-caprolactone (e.g., Monocryl); hyaluronic acid ester (e.g., Hyaff); poly(butylene-terephthalate)-co-(polyethyleneglycol) (e.g., Poly-active, Osteo-active); polydioxanon (e.g., PDS); polyethyleenoxyde, polyglactin (e.g. Vicryl, Vicryl Rapide, Vicryl Plus, Polysorb); polyglecapron (e.g., Monocryl); polyglycolic acid (e.g., Dexon); polyglyconate (e.g., Maxon); polyglyceride (e.g., Trilucent); polylactic acid (e.g., PLLA); poly L-lactic acid (PLLA) and polyglycolic acid (PGA) (e.g., in proportions of about 82% and 18%, respectively); poly L-lactic acid (PLLA) and copolymer (e.g., Lactosorb); poly-L-lactide, poly-D-lactide, and poly-glycolide; polyvinylalcohol (e.g., Bioinblue); polysaccharide; and propylene oxide.

In other embodiments, the vascular access port 100 can be formed of a combination of materials. For example, as discussed further below, in some embodiments, the guidance passageway 130 can be formed of a material that remains rigid indefinitely, or for a relatively long period, such as titanium, stainless steel, or a first type of resorbable material, and other portions of the vascular access port 100 can comprise a resorbable material, such as, for example, a second type of resorbable material that is resorbed within the body of a patient much quicker than is the first type of resorbable material.

With reference to FIG. 5, the bottom surface 108 of the base 102 can include any suitable ingrowth-inducing covering 152, which can facilitate integration or ingrowth of tissue in order to provide or enhance an attachment between a vessel and the vascular access port 100. In some embodiments, the ingrowth-inducing covering comprises a porous or roughened texture, which can be formed in any suitable manner. For example, in some embodiments, the texture is provided by compaction and sintering of metallic beads or powders, such as titanium beads, onto the bottom surface 108. In some embodiments, the beads may have a diameter of about 5 thousandths of an inch (i.e., approximately 0.13 millimeters) or smaller. In other or further embodiments, the ingrowth-inducing covering 152 can be formed by machining, sandblasting, laser etching, or injection molding of the bottom surface 108, or by attaching to the bottom surface 108 a fabric, such as polyester, Dacron®, or e-PTFE.

The ingrowth-inducing covering 152 can extend over the entire bottom surface 108 of the base 102, as shown in the illustrated embodiment, or over a significant portion thereof. In some embodiments, it can be desirable for the ingrowth-inducing covering 152 to cover a region that is forward of and/or that encompasses the opening 150 so as to provide a secure attachment between a vessel and the base 102 in this region, which can assist in ensuring that access devices 144 inserted through the opening 150 are consistently and repeatedly directed to the same portion of the vessel. For example, an attachment area AR may be defined over which it is desirable to provide a secure attachment to a vessel. The attachment area AR may be encompassed by a series of attachment passages 114 through which one or more attachment devices 116 may be advanced through the sidewall of a vessel into the lumen of a vessel to couple the vascular access device 100 to a vessel. The attachment area AR likewise may be covered by the ingrowth-inducing covering 152 which can provide a further connection between the vascular access port 100 and an outer layer of the vessel (e.g., the adventitia or media). The attachment area AR can surround the opening 150, as shown.

In some embodiments, the base 102 can be provided with an adhesive (not shown) in addition to or instead of the ingrowth-inducing covering 152 to provide a secure attachment between the base 102 and a vessel. For example, in some embodiments, the adhesive can comprise cyanoacrylate or fibrin glue.

It can be desirable for the vascular access port 100 to be configured for sufficiently secure attachment to a vessel such that the port 100 remains fixed relative to the vessel when it is influenced by forces from a needle or other access device 144. For example, attachment devices 116 coupled to the attachment passages 114, tissue attached to the ingrowth-inducing covering 152, and/or a bond provided by adhesives can resist relative longitudinal movement between the vascular access port 100 and the vessel when a tip of the access device 144 is urged forwardly along the funnel region 132 or forwardly within the channel 134. Similarly, such attachment features can resist relative rotational movement between the vascular access port 100 and the vessel when a tip of the access device 144 presses downwardly on either of the wings 140.

In some embodiments, it can be desirable to constrain the ingrowth-inducing covering 152 to the bottom surface 108 of the base 102, such as when it is desired to discourage, inhibit, or prevent the body 104 from attaching to surrounding tissue when the vascular access port 100 is implanted in a patient. For example, vessels can be somewhat mobile relative to surrounding tissue, and it may be more desirable for the vascular access port 100 to remain fixed relative to a vessel rather than relative to the tissue that surrounds the vessel. Accordingly, in some embodiments, the body 104 is relatively smooth. In other embodiments, at least a portion of the body 104 can comprise an ingrowth-inducing covering 152.

In some embodiments, at least a portion of the vascular access port 100 can include a covering (not shown), such as a coating and/or an embedded portion, that comprises one or more materials or agents that provide antiseptic, antimicrobial, antibiotic, antiviral, antifungal, anti-infection, or other desirable properties to the vascular access port 100, such as the ability to inhibit, decrease, or eliminate the growth of microorganisms at or near a surface of the port. For example, in various embodiments, the vascular access port 100 can comprise one or more of silver, platinum, gold, zinc, iodine, phosphorus, bismuth, alexidine, 5-flurouracil, chlorhexidine, sulfadiazine, benzalkonium chloride, heparin, complexed heparin, benzalkonoium chloride, 2,3 dimercaptopropanol, ciprofloxacin, cosmocil, cyclodextrin, dicloxacillin, EDTA, EGTA, myeloperoxidase, eosinophil peroxidase, fusidic acid, hexyl bromide, triclosan, polymyxin B, isopropanol, minocycline rifampin, minocycline EDTA, octenidine, ortho-phenyl phenol, triclocarban, triclosan, cephazolin, clindamycin, dicloxacillin, fusidic acid, oxacillin, rifampin, antibodies, peptides, polypeptides, free fatty acids, and oxidative enzymes. In some embodiments, the coating and/or the embedded material may be separate or independent from (e.g., non-coextensive with) the ingrowth-inducing covering 152. For example, in some embodiments, the ingrowth-inducing covering 152 is constrained to the base 102 of the vascular access port 100, whereas an antimicrobial covering is constrained to the body 104 of the vascular access port 100.

In the illustrated embodiment, a forward face 156 of the body 104 rises smoothly from the base 102 and is angled rearwardly. As shown in FIG. 7, in some embodiments, the forward face 156 may generally follow a contour of the channel 134 and may be substantially parallel thereto. For example, the forward face 156 can be convexly rounded in a manner similar to the channel 134. The body 104 can smoothly transition from the forward face 156 into depressions 158 at either side thereof, which can provide for a relatively smaller surface area of the body to which tissue might attach. The depressions 158 also can reduce the material costs associated with manufacture of the vascular access port 100.

Various parameters of the vascular access port 100 can be adjusted or selected to achieve a desired performance. For example, with reference to FIG. 3, a maximum width WF of the funnel region 132 can be greater than a maximum width WB of the base 102. Such an arrangement may be desirable where the vascular access port 100 is configured to be coupled with a relatively small vessel, or where a relatively large target area otherwise is desired. In various embodiments, the width WF is no less than about 1.0, 1.25, 1.50, 1.75, or 2.0 times the value of the width WB.

In some embodiments, the width WB of the base 102 can be approximately the same as or smaller than a width of a vessel to which the vascular access port 100 is configured to be attached. In various embodiments, the width WB of the base 102 can be no less than about 6, 7, 8, 9, 10, 11 or 12 millimeters, or can be no more than about 6, 7, 8, 9, 10, 11, or 12 millimeters.

In some embodiments, a height H of the vascular access port 100 can be adjusted or selected depending on the depth at which the port 100 is to be implanted within the patient. For example, some embodiments of the vascular access port 100 may be well-suited for use with a shallow vessel, such as a vein associated with an arteriovenous fistula in a forearm, whereas other embodiments may be well-suited for use with deeper vessels, such as the basilic vein in the upper arm. The depth at which the port 100 is located beneath a surface of the skin of the patient also can vary from patient to patient due to differences in anatomy. Sites at which various embodiments of the vascular access port 100 can be implanted include the cephalic, basilic, femoral, jugular, subclavian, or other suitable veins; arteries; fistulas; the stomach; other organs; or, more generally, any suitable structure where a walled membrane encircles or encapsulates a region.

In some embodiments, it can be desirable for an implanted vascular access port 100 to be beneath the surface of the skin of a patient by a sufficient amount to prevent tissue erosion, yet not so deep that palpation of the vascular access port 100 is difficult or provides insufficient information regarding the position or orientation of the port. In various embodiments, a minimum distance between a surface of the skin of a patient and an implanted port is no more than about 3, 4, 5, or 6 millimeters, is no less than about 3, 4, 5, or 6 millimeters, or is about 3, 4, 5, or 6 millimeters.

The height H can be defined as a minimum distance between the pinnacle region 122 and the bottom surface 108 of the base 102, and the height H can be selected, adjusted, or otherwise configured so as to achieve a desired depth of the vascular access port 100 beneath the surface of the skin of a patient. In various embodiments, the height H can be no greater than about 2, 3, 4, 5, 6, 7, 8, 9, 10, 11, 12, 13, 14, or 15 millimeters, or can be no less than about 2, 3, 4, 5, 6, 7, 8, 9, 10, 11, 12, 13, 14, or 15 millimeters. In other or further embodiments, the height H can be no more than about 0.5, 0.75, 1.0, 1.5, 2.0, 2.5, 3.0, or 3.5 times the width WB of the base 102, or can be no less than about 0.5, 0.75, 1.0, 1.5, or 2.0, 2.5, 3.0, or 3.5 times the width WB of the base 102. In other or further embodiments, the angle α, as defined above, can vary with the height H. For example, in some embodiments, the angle α increases with increasing height H.

It will be appreciated that various features of the embodiments of the vascular access port 100 discussed above can be altered or modified. For example, in some embodiments, the base 102 and the body 104 comprise separate pieces that are joined to each other. For example, the base 102 may comprise a relatively compliant material that can readily change shape so as to conform to a surface of a vessel, while at least a portion of the body 104 (e.g., the funnel region 132) can comprise a relatively rigid material. In other or further embodiments, the cavity 110 defined by the base 102 can be sized to receive any portion of a circumference of a vessel therein. Different sizes and configurations of the guidance passageway 130 are also possible, as further discussed below.

The vascular access port 100 can be implanted in a patient and used in any suitable methods. As mentioned above, it can be desirable to secure the vascular access port 100 to a vessel in such a manner that the bottom opening 150 defined by the guidance passageway 130 is fixed relative to the vessel, which can allow the guidance passageway 130 and/or the opening 150 to repeatedly direct an access device to the same portion of the vessel.

Figure 8:
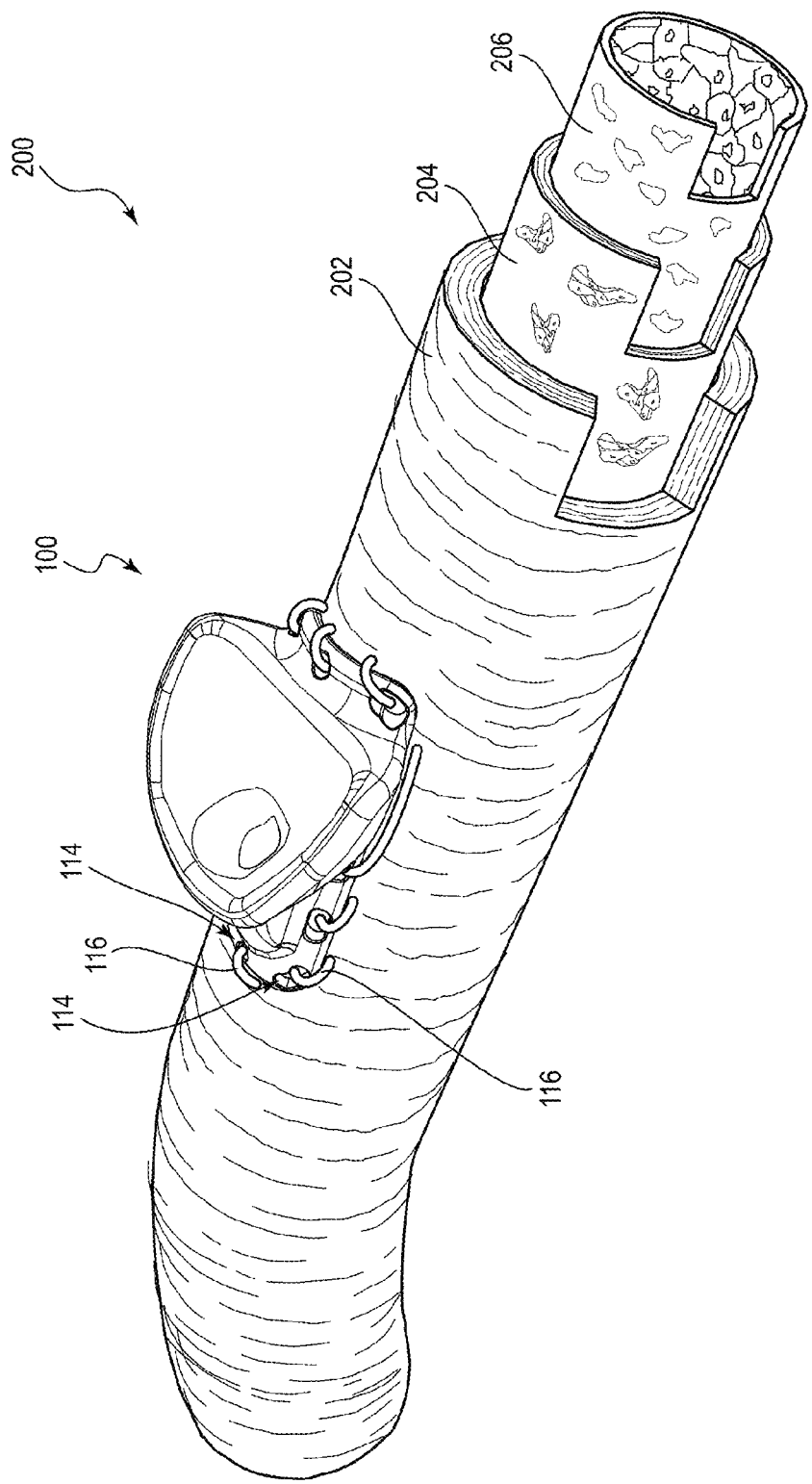
FIG. 8 is a perspective partial cutaway view of the vascular access port of FIG. 1 coupled with a vessel.

FIG. 8 depicts an example of one such arrangement. The vascular access port 100 is fixedly and directly secured to a vessel 200, which comprises three layers: the tunica adventita (or adventitia) layer 202, the tunica media (or media) layer 204, and the tunica intima (or intima) layer 206. The term "direct," when used herein with reference to securing or attaching a vascular access port 100 to the vessel 200, means that some portion of the vascular access port 100 is in abutting contact with the vessel 200 and is fixedly attached thereto. In the illustrated embodiment, an attachment device 116 comprises a running suture that extends through each attachment passage 114 of the vascular access port 100. One or more loops of the suture can extend through all three layers 202, 204, 206 of the vessel 200.

In certain embodiments, it can be desirable to ensure that one or more attachment devices 116 extend through more layers of the vessel 200 than just the adventitia layer 202 (or a portion thereof), or stated otherwise, through the media and/or the intima layers 204, 206. For example, it has been found that attachment of certain ports solely to the adventitia layer 202 (i.e., without attachment to other tissues) can result in mobility of the ports relative to the media and intima layers 204, 206. The ports may shift longitudinally and/or laterally relative to the inner layers 204, 206 of the vessel 200 from such activities as palpation of the ports during cannulation procedures or various day-to-day occurrences. Such mobility of a vascular access port can potentially result in the creation of multiple puncture sites in the vessel 200 over the course of repeated cannulations, which can weaken the vessel wall over time and potentially result in an aneurysm, vessel stenosis, hematoma, and/or bleeding.

FIGS. 9A-9E depict various stages of an illustrative method for implanting a vascular access port 100 in a patient 210 such that the vascular access port 100 provides direct access to a vessel within the patient 210. The term "patient" is used broadly herein and includes any animal subject who can or does undergo some process or procedure, whether provided by another or self-administered, and the term is not limited to an individual within a healthcare facility. The vascular access port 100 may be used with any suitable vessel, such as an artery 212, a vein 214 (both shown in FIG. 9A), or an artificial graft (see FIG. 14B). As previously discussed, the vessel may be at any of a variety of positions within the patient 210, such as the neck, the upper arm, the forearm, or the leg, and it may be located at a relatively deep or shallow position relative to the skin 216 of the patient. Numerous uses of an implanted port 100 are possible, including, for example, hemodialysis, chemotherapy, antibiotic therapy, total parenteral nutrition, pain management, aquapheresis, plasmapheresis, hydration, or long-term therapies of any suitable variety. In the illustrated method, a vascular access port 100 is shown being implanted in a forearm of the patient 210—specifically, the vascular access port 100 is shown being connected to a vein 214 that is associated with an arterio-venous fistula 218 for use in hemodialysis. It is noted that the vein 214 is a three-layered vessel such as the vessel 200 depicted in FIG. 8, and thus may be referred to hereafter as a vessel 200 to illustrate the more general applicability of the procedures discussed.

Figure 9A:
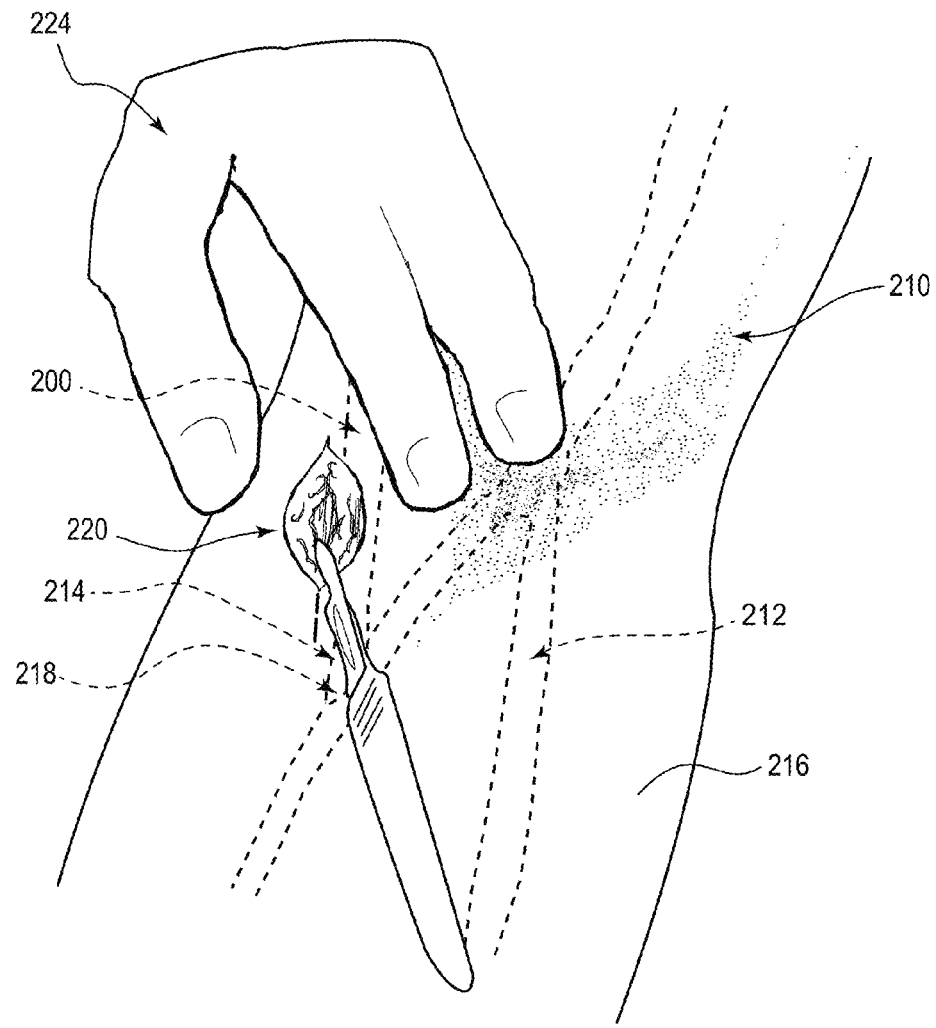
FIG. 9A is a perspective view of a stage of an illustrative method of implanting an embodiment of a vascular access port in a patient depicting the creation of an incision.

With reference to FIG. 9A, an incision 220 can be made in the skin 216 of the patient 210. In the illustrated embodiment, the incision 220 can be from about 4 centimeters to about 5 centimeters in length. The incision 220 can extend substantially parallel to the vessel 200, but can be offset relative thereto (i.e., is not directly over the vessel 200). In the illustrated embodiment, the incision 220 is offset from a position directly over the vessel 200 by a distance of from about 2 centimeters to about 3 centimeters. As discussed further with respect to FIG. 9E, such an orientation of the incision 220 can facilitate access to the vascular access port 100 after the implantation procedure is complete. In other methods, the incision 220 can be directly over the vessel 200 and/or at an angle or entirely transverse relative thereto. The incision 220 can be made by a practitioner 224 using any suitable techniques and instruments.

Figure 9B:
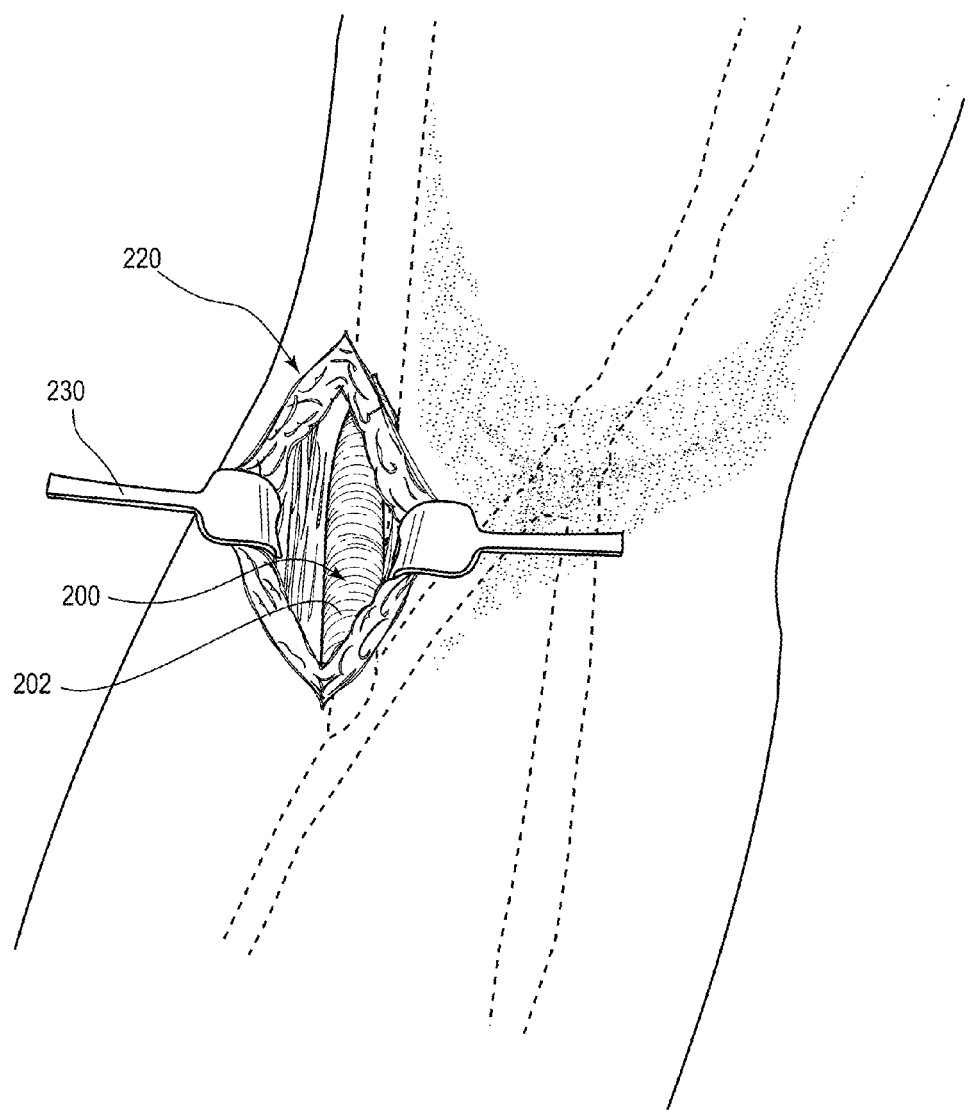
FIG. 9B is a perspective view of another stage of the method of FIG. 9A in which a vessel is exposed.

With reference to FIG. 9B, the vessel 200 can be exposed by removing, partially removing, or separating skin, fat, and fascial layers from the adventitia layer 202 of the vessel 200 at the site of the incision 220. Exposure of the vessel 200 can be maintained in any suitable manner, such as by the use of tissue spreaders 230.

Figure 9C:
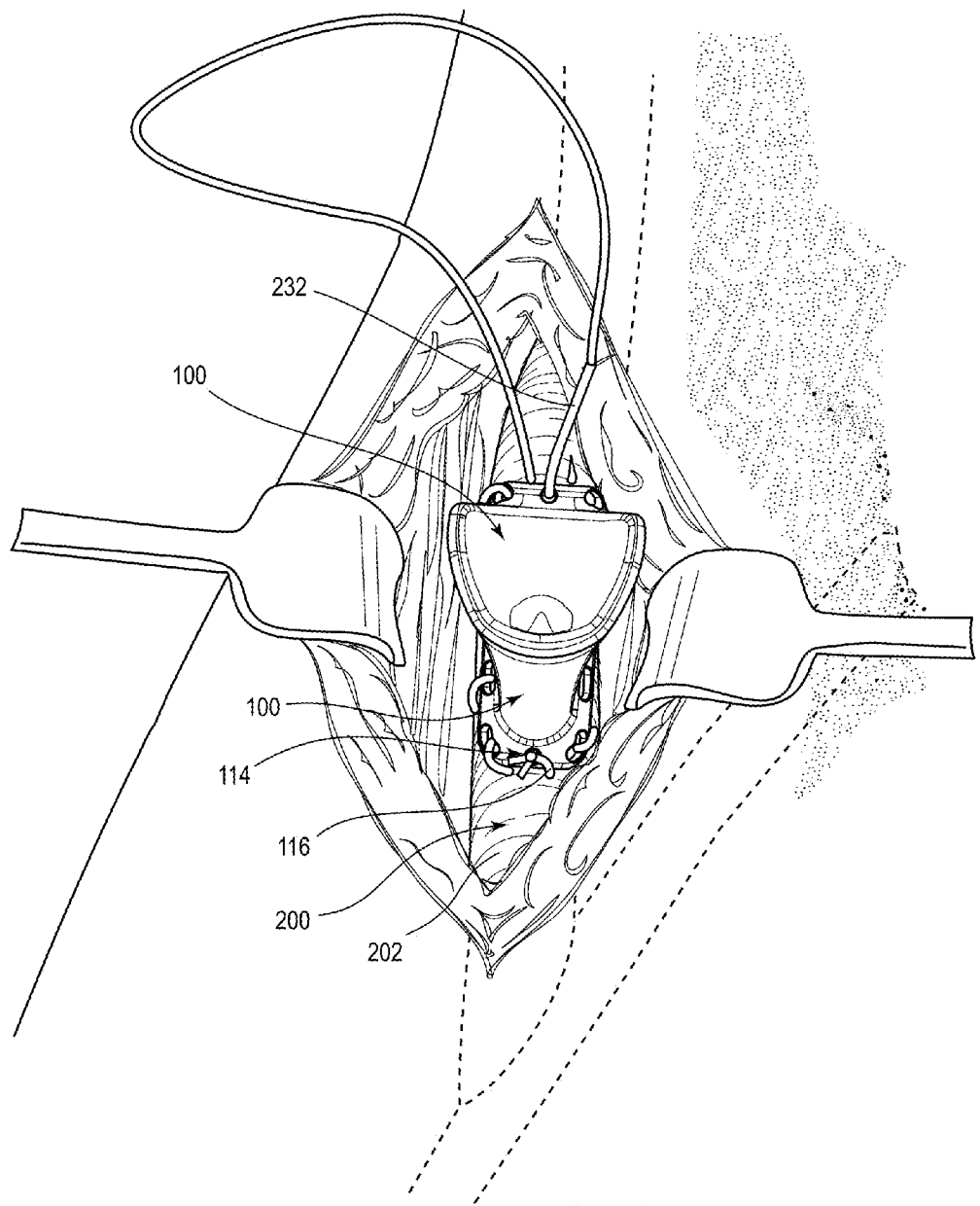
FIG. 9C is a perspective view of another stage of the method of FIG. 9A in which an attachment is made between the vascular access port and the vessel.

With reference to FIG. 9C, an initial attachment of the vascular access port 100 to the vessel 200 can be achieved at the front end or the back end of the vascular access port 100. In some procedures, an attachment device 116 can be inserted through all three layers 202, 204, 206 (see FIG. 8) of the vessel 200 and through an attachment passage 114 at each of the front and back ends of the vascular access port 100 along a lateral center of the port 100 prior to use of any of the remaining attachment passages 114. Initial attachment of the front end and/or the back end of the vascular access port 100 can assist in ensuring that a desired orientation of the vascular access port 100 is achieved and maintained during the course of the implantation procedure.

As previously mentioned, any suitable attachment device (or devices) 116 may be used in securing the vascular access port 100 to the vessel 200. The attachment devices 116 can include, for example, one or more sutures, pinch rings, hooks, or wires. Once an attachment device 116 is in a desired position, it can be securely tied, crimped, twisted, or otherwise fastened.

In the illustrated embodiment, the attachment device 116 comprises a running suture, which can be looped through multiple attachment passages 114. In the illustrated embodiment, a single running suture 116 is used to secure the vascular access port 100 to the vessel 200. In other embodiments, the suture 116 may extend through fewer passages 114 and one or more additional sutures 116 may be used. For example, as previously discussed, in some embodiments, a separate suture 116 is secured at each end of the vascular access port 100 prior to providing sutures in any of the remaining attachment passages 114.

Various options are available for securing one or more sutures 116 in place. For example, in some procedures, a suture needle 232 can be inserted through the wall of the vessel 200 at a position near an attachment passage 114, and can then pass through the attachment passage 114 after having passed through the vessel wall. A suture 116 associated with the suture needle 232 can then be tied using a surgical knot and the excess suture trimmed. In other procedures, a suture 116 can be positioned at a desired location within the wall of the vessel 200 such that at least one leg thereof protrudes from the adventitia layer 202. The protruding leg of the suture 116 can be received through a desired attachment passage 114 of the vascular access port 100 as the port 100 is brought into contact with the vessel 200. The suture 116 can then be tied and trimmed. Either approach may be used to secure sutures 116 through any desired number of attachment passages 114 of the vascular access port 100. Any other suitable suturing or attachment technique may be used. In some embodiments, only a portion of the available attachment passages 114 are used.

Figure 9D:
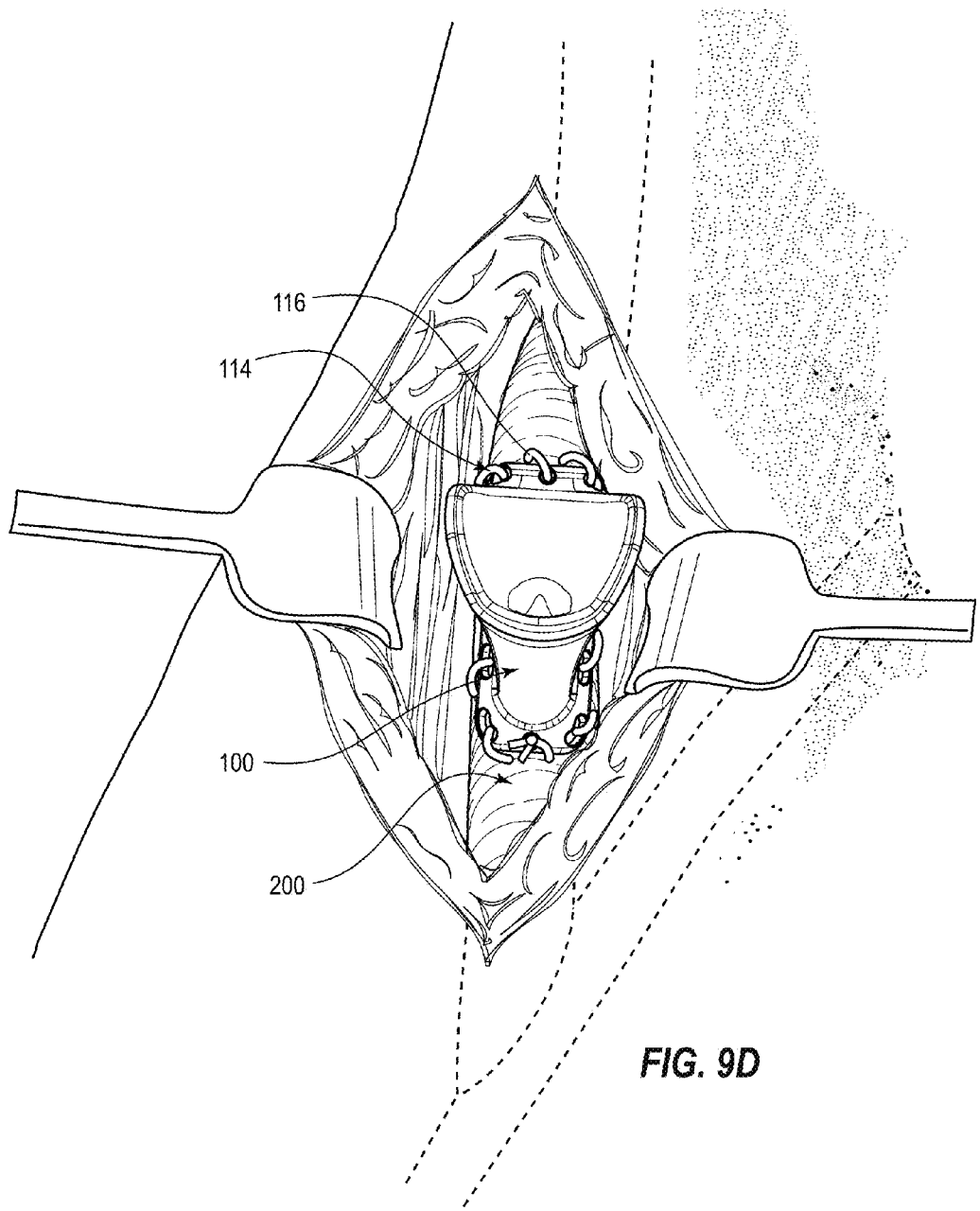
FIG. 9D is a perspective view of another stage of the method of FIG. 9A in which additional attachments have been made between the vascular access port and the vessel.

With reference to FIG. 9D, additional sutures 116 can be used to secure the vascular access port 100 to the vessel 200 via any or all of the remaining attachment passages 114, as desired. In some embodiments, the attachment passages 114 are filled, such as with silicone, so as to prevent ingrowth of tissue. In other embodiments, the attachment passages 114 are left open, which can permit ingrowth of tissue therein or therethrough.

Figure 9E:
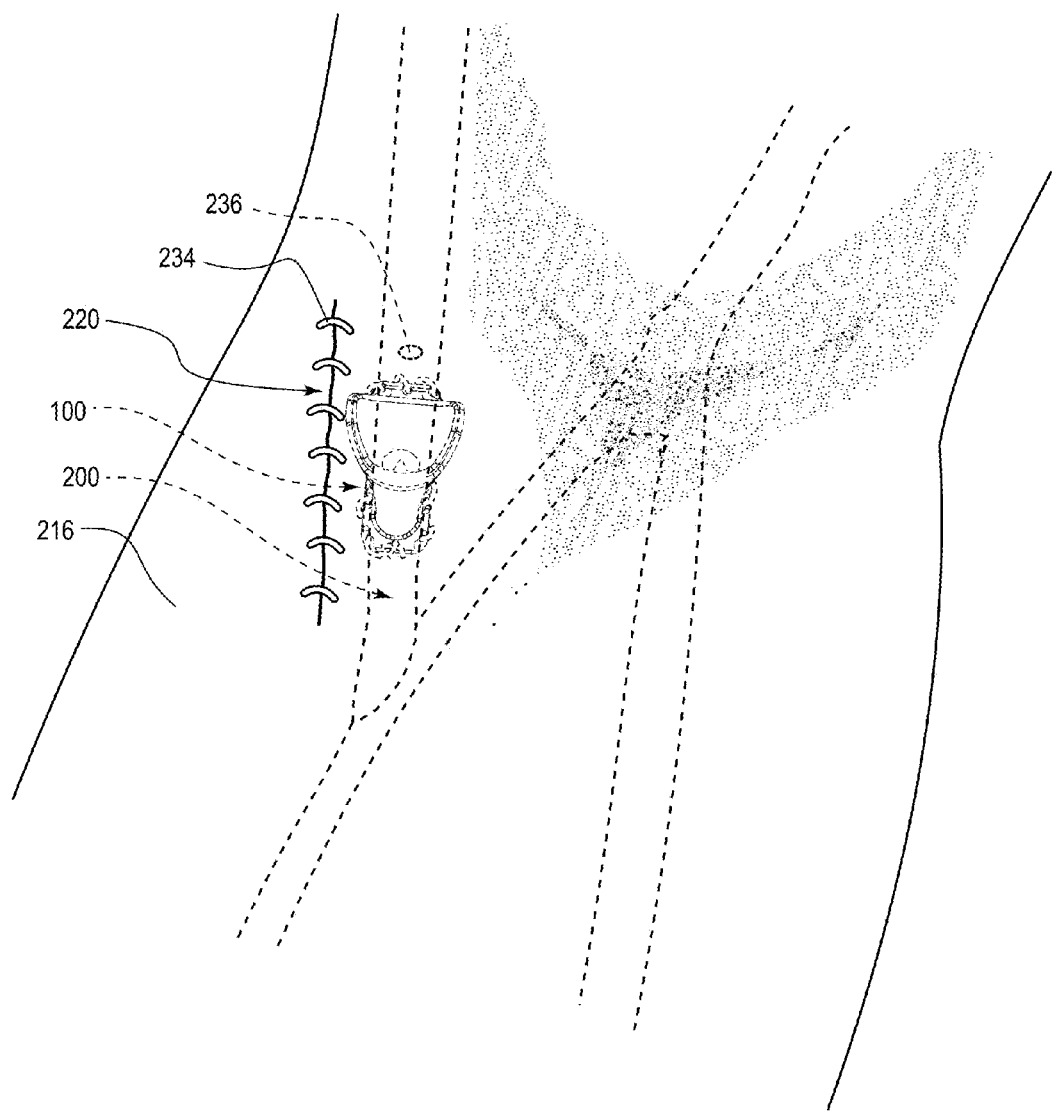
FIG. 9E is a perspective view of another stage of the method of FIG. 9A in which the incision has been closed.

With reference FIG. 9E, the site of the incision 220 can be closed in any suitable manner, such as, for example, via one or more sutures 234. As previously mentioned, the incision 220 can be offset from a position that is directly above the vascular access port 100. In such arrangements, an access device 144 can be inserted through the skin 216 to the vascular access port 100 via a surface insertion site 236 with little or no interaction with the site of the incision 220, or stated otherwise, without contacting any or much scar tissue at or beneath the surface of the skin 216. In certain cases, this may assist in the creation of an insertion tract that extends from the surface insertion site 236 to the vascular access port 100, as discussed further below.

In certain embodiments, it can be desirable to wait for a period of days or weeks after implantation of the vascular access port 100 before accessing the vessel 200 thereby. The waiting period can provide sufficient time for tissue ingrowth at the appropriate areas of the vascular access port 100, which can provide a more secure connection between the vascular access port 100 and the vessel 200.

FIGS. 10A-10G depict various stages of another illustrative method for implanting a vascular access port 100 in the patient 210 such that the vascular access port 100 provides direct access to the vessel 200 within the patient 210. Although the methods shown in FIGS. 9A-9E and 10A-10G are depicted relative to the same site within the patient 210, it is to be understood that the methods also may be used at other sites.

Figure 10A:
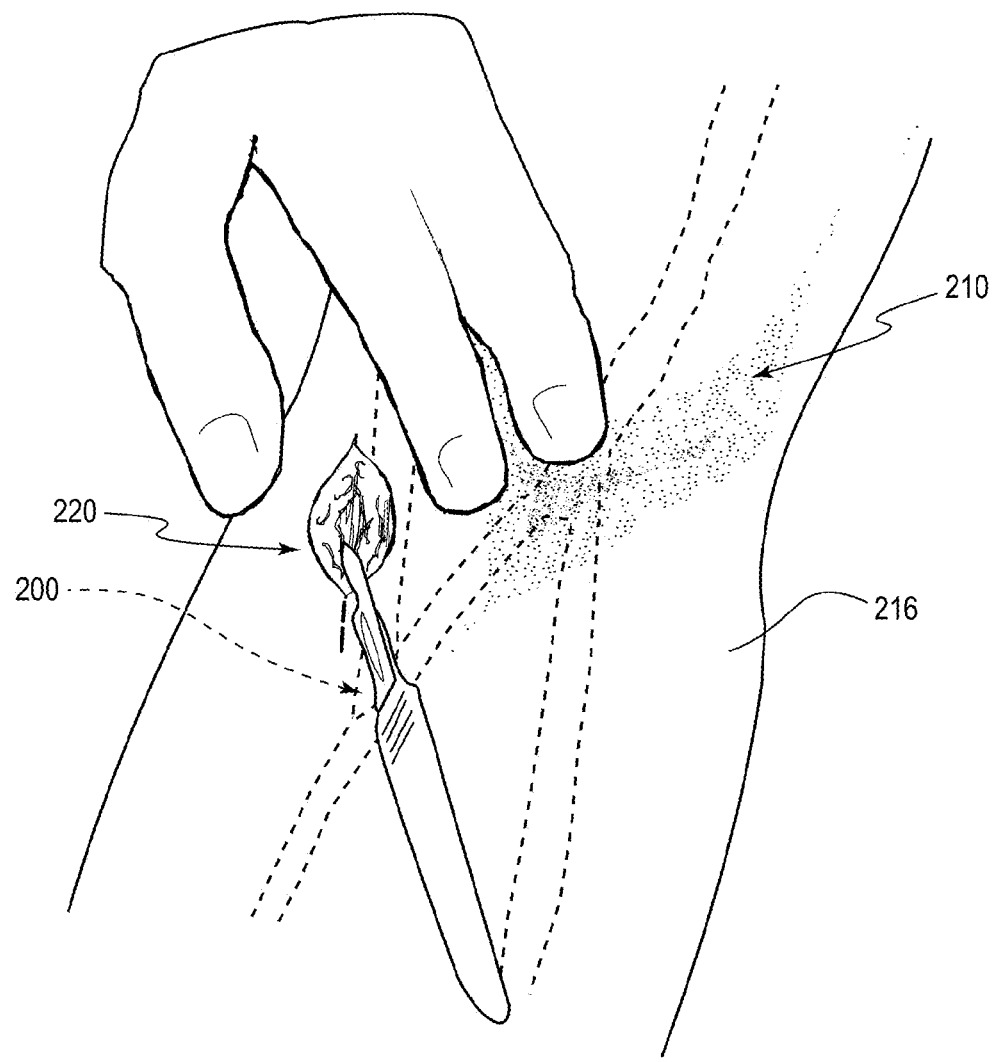
FIG. 10A is a perspective view of a stage of another illustrative method of implanting an embodiment of a vascular access port depicting the creation of an incision in the skin of a patient.

With reference to FIG. 10A, an incision 220 can be made in the skin 216 of the patient 210, which in some embodiments can be from about 4 centimeters to about 5 centimeters in length. The incision 220 can extend substantially parallel to vessel 200 and can be offset relative thereto. In some embodiments, the offset can be by a distance of from about 2 centimeters to about 3 centimeters.

Figure 10B:
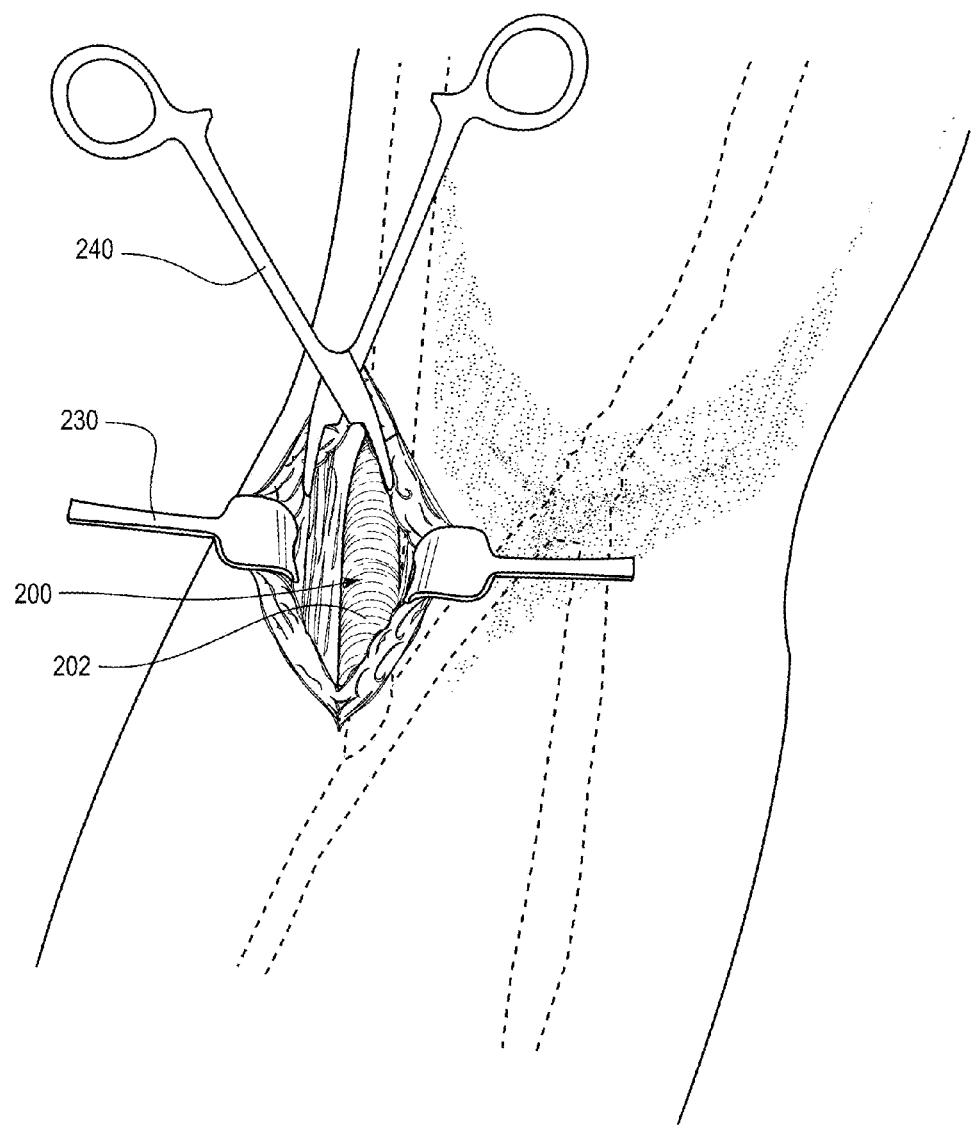
FIG. 10B is a perspective view of another stage of the method of FIG. 10A in which adventitia of a vessel is isolated.

With reference to FIG. 10B, the vessel 200 can be exposed by removing, partially removing, or separating skin, fat, and fascial layers from the adventitia layer 202 of the vessel 200 at the site of the incision 220. In some cases, a hemostat 240 can assist in this process. Exposure of the vessel 200 can be maintained in any suitable manner, such as by the use of tissue spreaders 230.

Figure 10C:
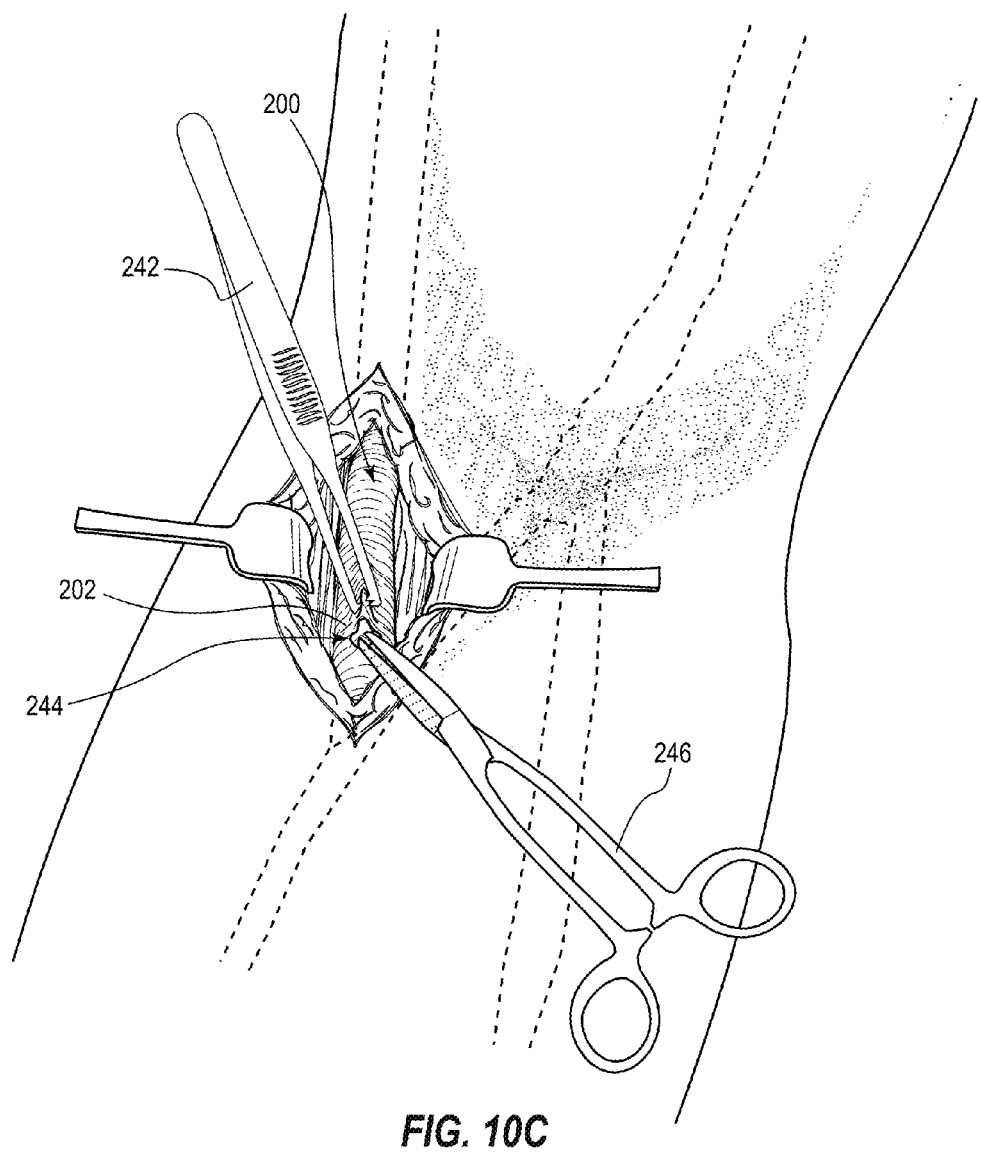
FIG. 10C is a perspective view of another stage of the method of FIG. 10A in which in incision is made in the adventitia.

With reference to FIG. 10C, a portion of the adventitia 202 can be isolated or separated from other portions of the vessel 200 in any suitable manner, such as via one or more forceps 242. Each set of forceps 242 can be used to capture or gather up a portion of the adventitia 202 and/or fascia layers or fat that may not have been removed or spread apart by the tissue spreaders 230.

With reference to FIG. 10C, while the portion of adventitia 202 is being held in its separated state, a small incision 244 can be made therein in any suitable manner, such as via a scalpel or via scissors 246.

Figure 10D:
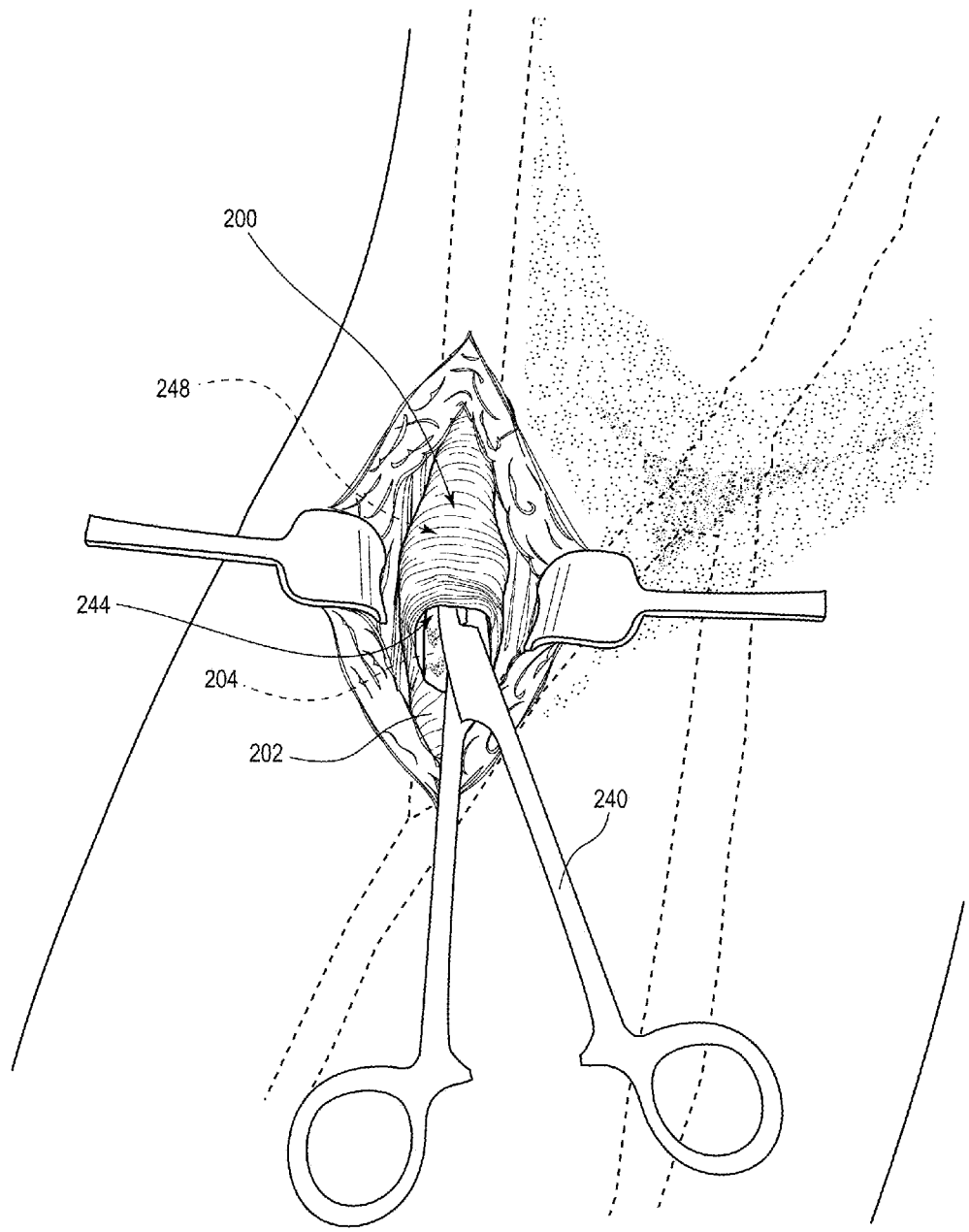
FIG. 10D is a perspective view of another stage of the method of FIG. 10A in which a pocket is formed in the adventitia.

With reference to FIG. 10D, a hemostat 240 can be inserted through the incision 244 so as to slide between the isolated adventitia 202 and the remaining layers of the vessel 200. In instances, it can be difficult to separate all of the adventitia 202 from the media layer 204 of the vessel 200. This, in the illustrated embodiment, the media layer 204 is shown, but is obscured by a thin layer of adventitia 202. The hemostat 240 can be used to bluntly dilate a pocket 248 within the adventitia 202 layer. Although not depicted, in some cases, the forceps 242 may be used to maintain control of the adventitia 202 during formation of the pocket 248.

In certain embodiments, the pocket 248 can be sufficiently large to receive the vascular access port 100 therein, while in others, the pocket 248 can be slightly smaller than the vascular access port 100. In some embodiments, the pocket 248 can have a length of no more than about 2.0, 2.5, 3.0, or 3.5 centimeters, and can have a width of no more than about 70, 80, or 90 percent of a width of the outer diameter of the media layer 204.

Figure 10E:
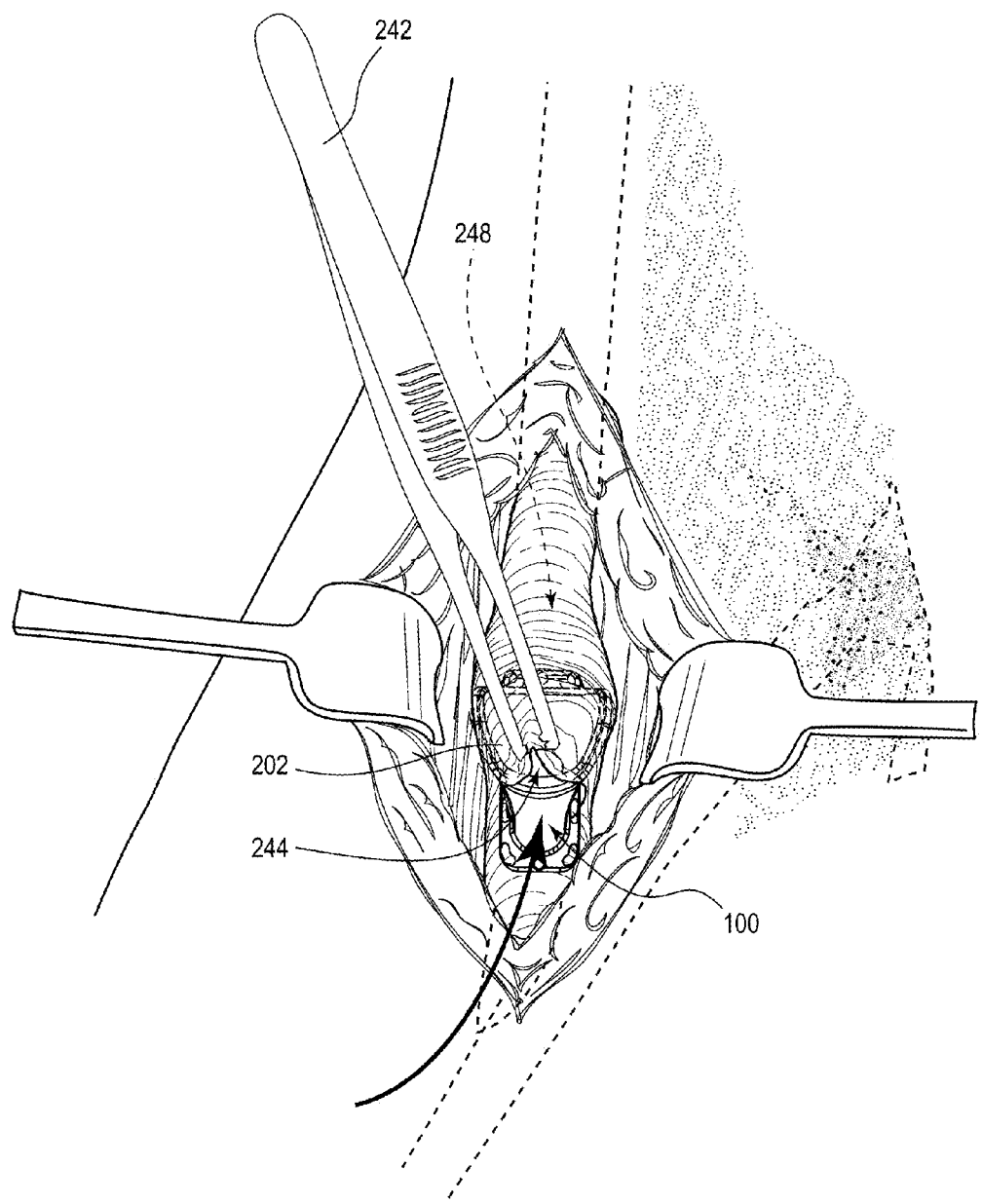
FIG. 10E is a perspective view of another stage of the method of FIG. 10A in which an embodiment of a vascular access port is inserted into the pocket.

With reference to FIG. 10E, the vascular access port 100 can be inserted through the incision 244 into the pocket 248. In some cases, the forceps 242 or other clamping devices are used to maintain control of the adventitia 202 during insertion of the vascular access port 100. The vascular access port 100 can be introduced into the pocket 248 either rearward end first, as shown, or forward end first, and the port 100 can be pushed to the end of the pocket 248 opposite the incision 244.

Figure 10F:
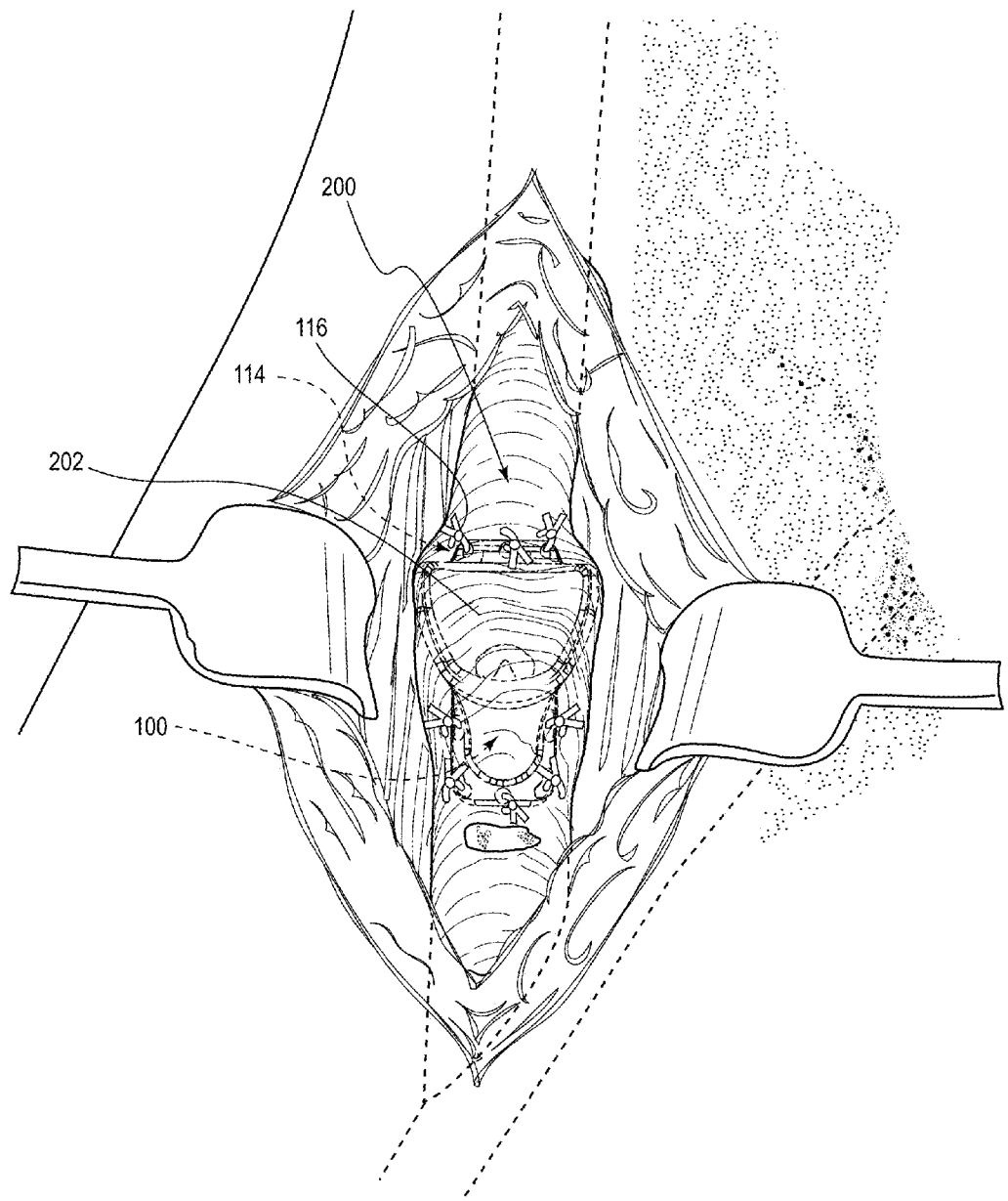
FIG. 10F is a perspective view of another stage of the method of FIG. 10A in which attachments have been made between the vascular access port and the vessel.

With reference to FIG. 10F, the adventitia 202 can cover all or substantially all of the implanted vascular access port 100 when it is within the pocket 248. Sutures 116 can be advanced through the adventitia 202, through the attachment passages 114, and through the remaining portion of the adventitia layer 202, as well as through the entirety of the media and intima layers 204, 206 to attach the vascular access port 100 to the vessel 200. Suture knots thus may be tied outside of the adventitia 202. In other embodiments, the sutures 116 do not pass through the separated portion of the adventitia 202 and may be tied prior to being covered by the adventitia 202.

Figure 10G:
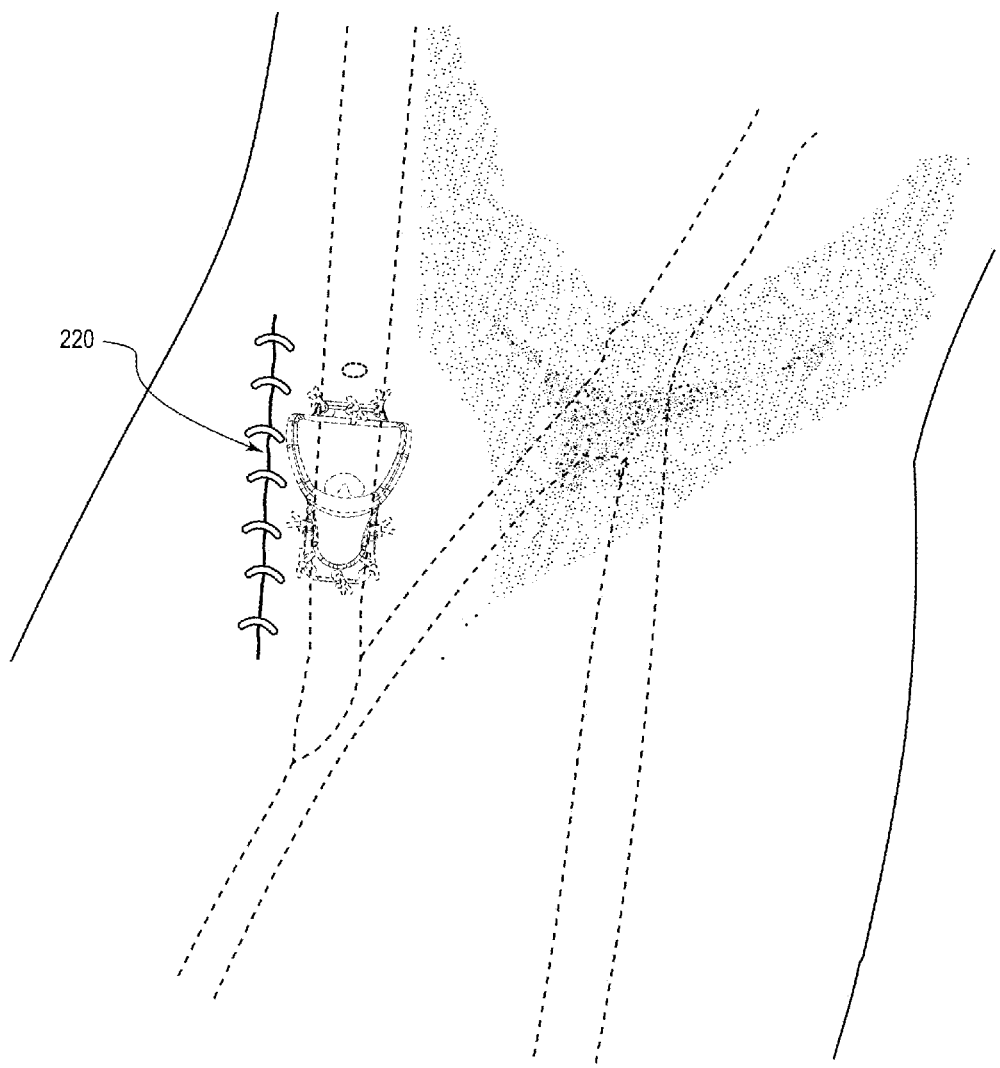
FIG. 10G is a perspective view of another stage of the method of FIG. 10A in which the incision in the skin of the patient has been closed.

FIG. 10G depicts the site of the incision 220 in a closed configuration. The incision 220 can be closed in any suitable manner, such as in any of the manners described above with respect to FIG. 9E.

With reference again to FIGS. 10C-10F, in other methods, at least a portion of the adventitia 202 can be removed rather than forming the pocket 248 therein. The vascular access port 100 may be placed atop a thin layer of the adventitia 202 at a site from which the at least a portion of adventitia 202 has been removed, and sutures 116 may be directly inserted through the attachment passages 114 and through the thinned adventitia layer 202, the media layer 204, and the intima layer 206. The vascular access port 100 may, at least initially, be less stable relative to the vessel 200 when it is implanted in this manner, rather than when it is inserted into the pocket 248.

FIGS. 11A-11E depict various procedures that may be performed relative to an implanted vascular access port 100. As will be discussed, the vascular access port 100 can facilitate the creation of a buttonhole. The vascular access port 100 likewise can facilitate use of the buttonhole once it is formed. These and/or other advantages of the vascular access port 100 will be apparent from the disclosure that follows.

Additionally, as previously mentioned, tissue may grow into or attach to various areas of the vascular access port 100. For example, vessel tissue may grow into the ingrowth-inducing covering 152. In some embodiments, skin tissue may grow into at least a portion of the guidance passageway 130, although such ingrowth is not shown in FIGS. 11A-11E.

Figure 11A:
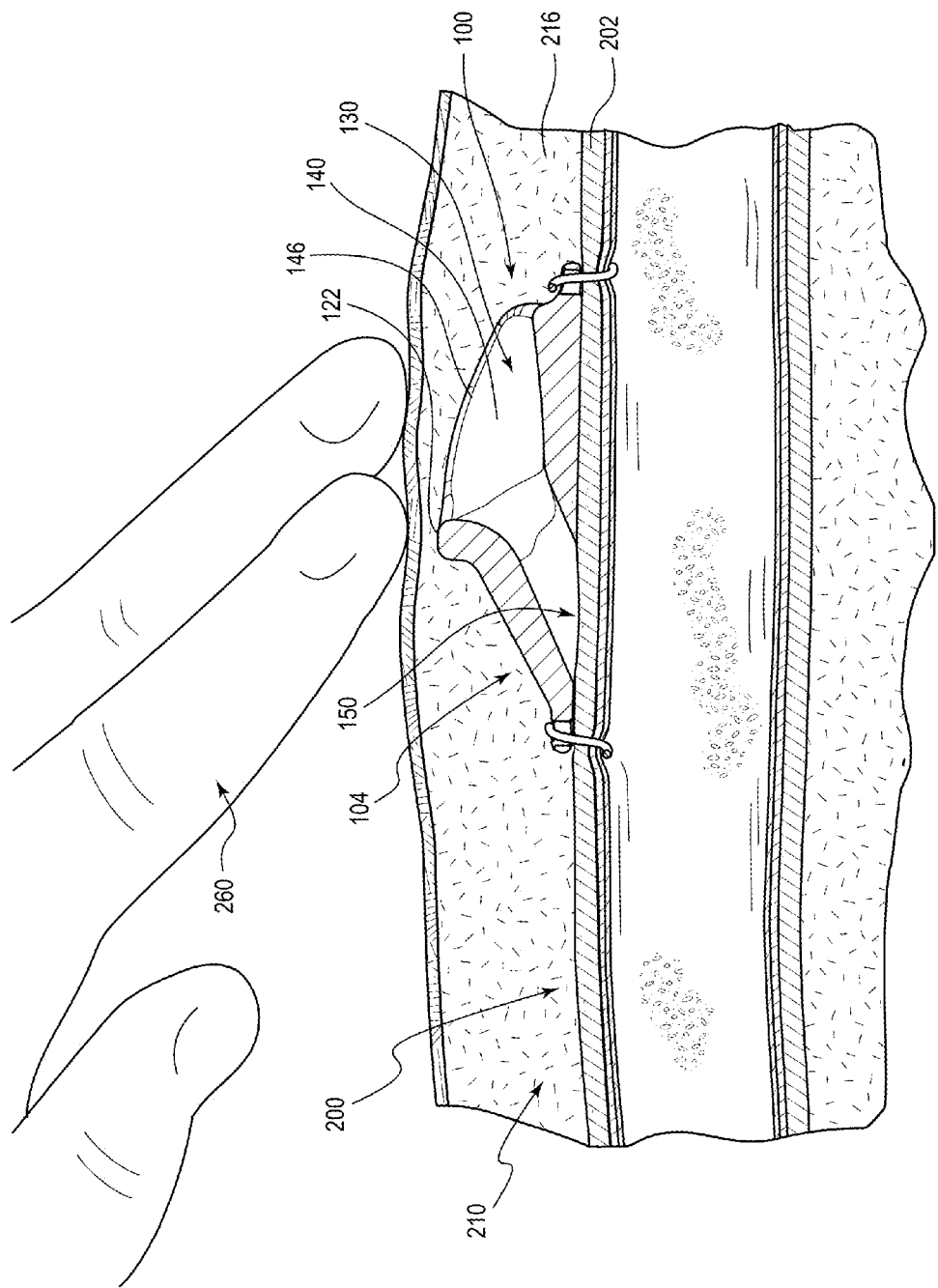
FIG. 11A is a cross-sectional view of a palpations stage of an illustrative method relating to the creation and use of a buttonhole access site to access a lumen of a vessel.

FIG. 11A depicts an embodiment of the vascular access port 100 that has been implanted in the patient 210 in any suitable manner, such as via the method depicted in FIGS. 9A-9E. The opening 150 of the guidance passageway 130 is at or adjacent to the vessel 200. Specifically, in the illustrated embodiment, the opening 150 is at the adventitia layer 202 of the vessel 200.

In the stage that is shown, a clinician 260 palpates the skin 216 to locate and determine the orientation of the vascular access port 100. The term "clinician" is used broadly herein and includes any individual who conducts a process or procedure relative to an implanted access port 100, whether that individual is the individual in whom the access port 100 is implanted (e.g., a patient) or someone else, and the term is not limited to an individual within a healthcare facility. In the illustrated embodiment, the clinician 260 is using fingers to contact the skin 216 located above the pinnacle region 122 of the palpation projection 146. In other instances, the clinician 260 can palpate any other suitable portion of the body 104 to determine the location (e.g., depth) and orientation of the port 100. For example, the clinician 260 may use one or more fingers and/or a thumb to contact the skin 216 that is over or beside other portions of the palpation projection 146, or to squeeze the skin 216 that is at either side of the wings 140. In still other or further embodiments, a clinician may visually determine a location and orientation of the port 100. Prior or subsequent to the stage shown in FIG. 11A, the clinician 260 can clean a surface of the skin with any suitable antiseptic so as to reduce the risk of introducing pathogens into the bloodstream of the patient.

Figure 11B:
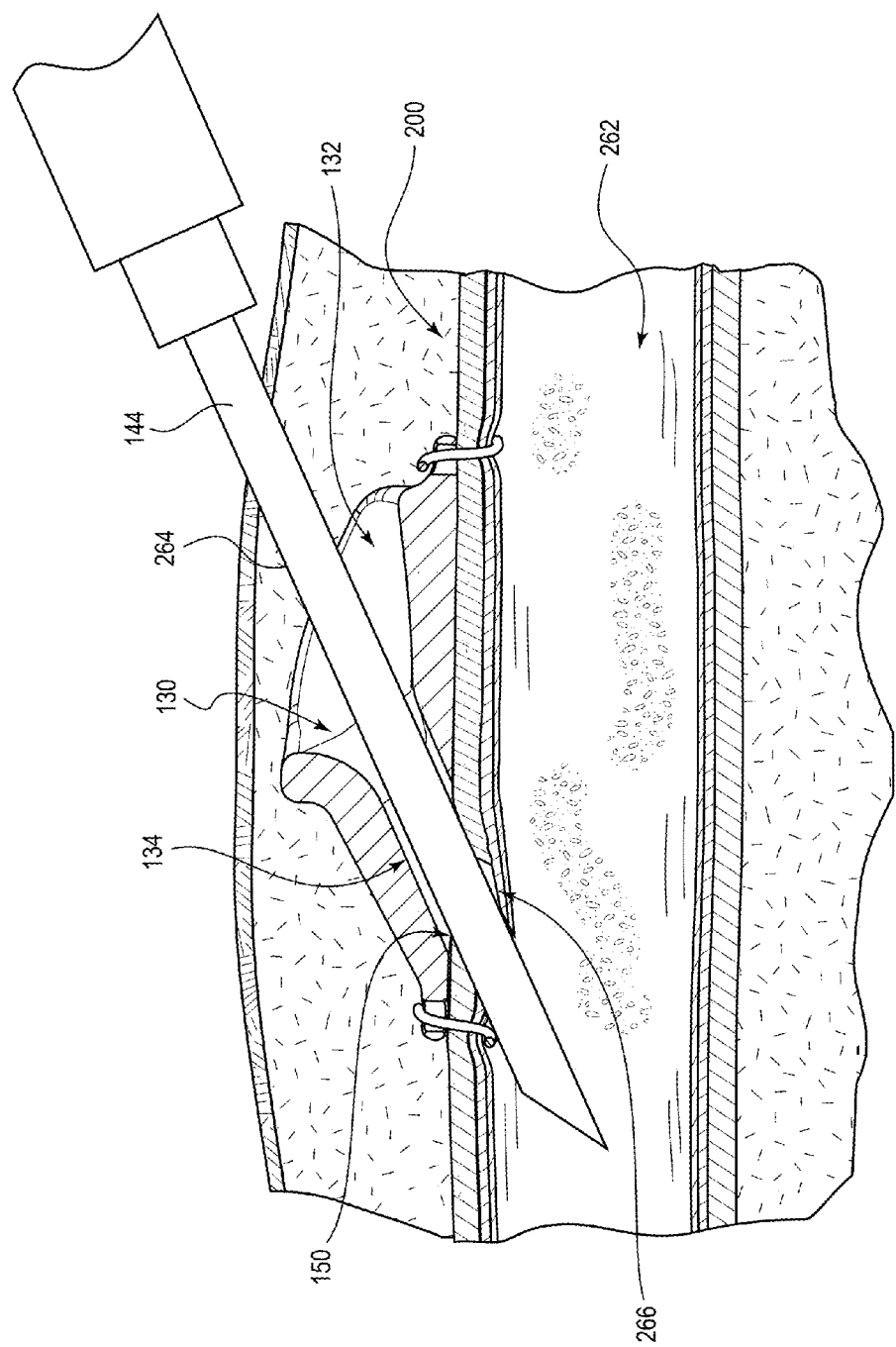
FIG. 11B is a cross-sectional view of another stage of the method of FIG. 11A in which a needle having a sharp tip is inserted into the lumen of the vessel via an embodiment of a vascular access port.

FIG. 11B illustrates an embodiment of an access device 144 directly accessing a lumen 262 of the vessel 200 via the vascular access port 100 for a first time. Although the fingers of the clinician 260 are not shown in FIG. 11B, the clinician 260 may continue to palpate the vascular access port 100 while inserting the access device 144 into the skin and the vascular access port 100. This can aid in achieving a desired alignment of the access device 144 with the guidance channel 130. The clinician 260 also may make minor adjustments to an orientation of the vascular access port 100 by applying pressure thereto.

The access device 144 can comprise any suitable device configured for fluid communication between a position outside of the skin 216 and the vessel lumen 262 when the device has been introduced into the lumen 262 via the vascular access port 100. For example, in various embodiments, the access device 144 can comprise a needle or a catheter. In many embodiments, the access device 144 can be relatively rigid so as to be able to readily pass through the skin 216. Accordingly, in some embodiments, the catheter may be an over-the-needle catheter.

Standard needles that are presently used in hemodialysis or other procedures may be used with embodiments of the vascular access port 100, which may facilitate use of such ports. For example, standard protocols for making and using buttonholes in vessels via known freehand methods may be readily adapted to "device-assisted" buttonhole techniques that employ the vascular access ports 100, and this can take place without alteration to the instruments called for by the existing protocols.

As the procedural stage depicted in FIG. 11B represents an initial access of the vessel lumen 262, the access device 144 is shown as having a sharp tip, which can allow the access device 144 to more readily be inserted through the unbroken skin so as to form an insertion tract 264, and also through an insertion site 266 of the vessel 200. As further discussed below, however, other embodiments of an access device 144 that have blunt ends may be used after multiple access events have occurred. For example, as discussed hereafter, a sharp access device 144 can be used for a number of access events (e.g., 6, 7, 8, 9, or 10 access events) until an insertion tract has been formed through the skin of a patient, and a blunt access device 144 can be used thereafter.

In certain embodiments, the access device 144 can comprise a needle sized from 14 gauge to 20 gauge. As previously mentioned, the diameter and length of the channel 134 can be configured to direct the access device 144 to a specific region of the vessel 200. This may be achieved by a relatively close fit between the channel 134 of the vascular access port 100, which can provide for a predictable orientation at which the access device 144 will exit the channel 134 through the opening 150. In some instances, it may be desirable for the channel 134 to be sized such that at least a small amount of space exists between an inner wall thereof and an access device 144 when the access device 144 is inserted therein. This can prevent or reduce binding of the access device 144 within the channel 134, which may be more likely to occur if tissue has grown into at least a portion of the channel 134. In some embodiments, a balancing or optimization may be achieved with respect to the spacing between the channel 134 and an access device 144 such that a sufficiently tight fit is achieved to allow the vascular access device 144 to be directed repeatedly to substantially the same area of the vessel 200 and to achieve hemostasis when the vascular access device 144 is inserted into the vessel 200 while inhibiting, reducing the occurrence of, or preventing binding of the vascular access device 144 within the channel 134. In various embodiments, an inner diameter of the channel 134 is larger than an outer diameter of an access device 144 with which it is configured to be used by an amount within a range of from about 0.25 gauge to about 3.0 gauge, from about 0.5 gauge to about 2.0 gauge, from about 0.75 gauge to about 1.5 gauge, or from about 0.75 gauge to about 1.25 gauge; by an amount that is no less than about 0.25, 0.5, 0.75, 1.0, 1.25, 1.5, 1.75, 2.0, 2.5, or 3.0 gauge; or by an amount that is no greater than about 0.25, 0.5, 0.75, 1.0, 1.25, 1.5, 1.75, 2.0, 2.5, or 3.0 gauge. In some embodiments, the channel 134 is about 1 gauge larger than access devices 144 with which it is configured to be used. For example, in the illustrated embodiment, the channel 134 may be sized at approximately 14 gauge and the access device 144 can comprise a 15 gauge fistula needle.

Other configurations for the channel 134 and the access device 144 are also possible. For example, one or more of the channel 134 and the access device 144 may have geometries other than cylindrical. In certain of such embodiments, the geometries of the channel 134 and of the access device 144 may be complementary to each other, whereas in other embodiments, a cross-sectional shape of the channel 134 may be different from a cross-sectional shape of the access device 144.

As previously mentioned, some protocols for the creation and use of buttonhole cannulation sites can require introduction of a needle into a vessel at a designated acute angle. In some embodiments, the angle α defined by the channel 134 (see FIG. 7) can be matched to this specified angle, and the channel 134 can constrain the access device 144 to enter the vessel 200 at the angle α, such that the vascular access port 100 can be configured for use with such protocols.

Figure 11C:
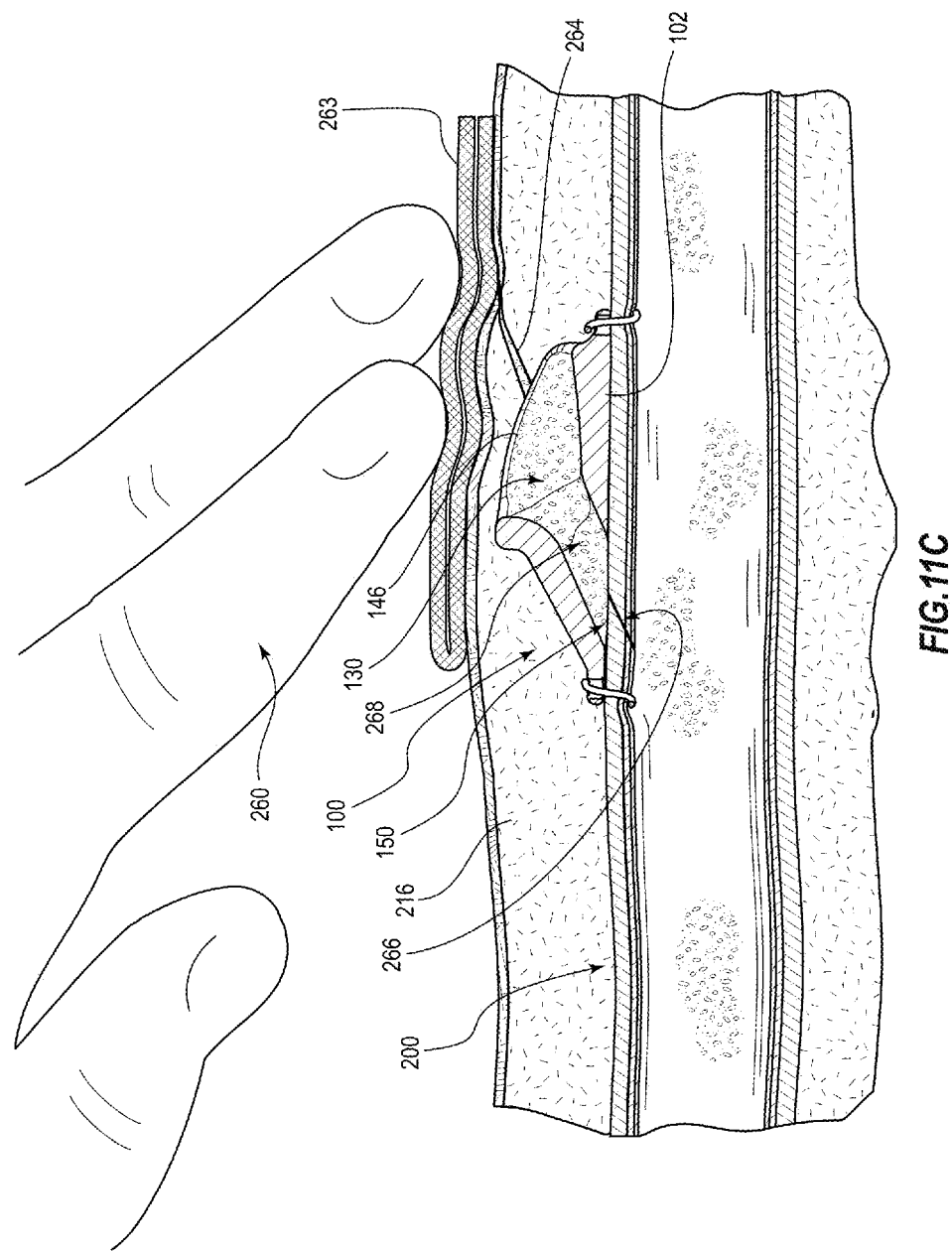
FIG. 11C is a cross-sectional view of another stage of the method of FIG. 11A in which pressure is applied to the skin of the patient.

FIG. 11C illustrates a stage of the procedure after removal of the access device 144. The insertion site 266 is shown in a closed state, in which it is allowed to heal. Prior to closure and healing of the insertion site 266, however, blood 268 can be permitted to exit thereby, and may fill the guidance passageway 130 and the insertion tract 264. The practitioner 260 can apply pressure above the vascular access port 100 to close the insertion tract 264 until bleeding subsides at the surface of the skin 216. For example, the practitioner 260 can apply pressure while simultaneously applying a pad 269 (e.g., gauze) to the upper end of the insertion tract 264. As previously mentioned, the entry mouth 136 of the guidance passageway 130 can be configured to assist in achieving hemostasis. For example, the entry mouth 136 may be relatively planar, and application of pressure above the entry mouth 136 can cause tissue surrounding the guidance passageway 130 to effectively seal the guidance passageway 130 about the entry mouth 136. In some embodiments, a two-finger technique may be used to close the insertion tract 264 while applying pressure to the tissue positioned above the guidance passageway 130. In some embodiments, pressure may be applied for a period of no more than about 5, 6, 7, 8, 9, or 10 minutes in order to achieve hemostasis.

A relatively tight attachment between the vascular access port 100 and the vessel 200, such as may be achieved by tissue ingrowth within the attachment area AR (see FIG. 5) likewise can assist in reaching hemostasis. For example, tissue ingrowth about the opening 150 can inhibit or prevent blood 268 from seeping outwardly between the base 102 of the vascular access port 100 and the vessel 200.

The procedures discussed with respect to FIGS. 11A-11C can be repeated multiple times. For example, with reference again to FIG. 11B, a second access device 144 having a sharp tip can be inserted through the insertion tract 264 toward the vascular access port 100 for a second insertion event. However, during the time between the first and second access events and/or as a result of palpation of the vascular access port 100 during the second access event, the vascular access port 100 and the vessel 200 to which it is attached may have shifted relative to the insertion tract 264 such that the channel 134 is no longer aligned with the insertion tract 264. As the access device 144 is advanced through the insertion tract 264, the tip of the access device 144 can contact the funnel region 132. The funnel region 132 then can direct the tip of the access device 144 into the channel 134 as the access device 144 is further advanced through the insertion tract 264. In some cases, this redirection of the tip of the access device 144 relative to the vascular access port 100 may urge the insertion tract 264 and the channel 134 into alignment with each other. Once the tip of the access device 144 enters the channel 134, the channel 134 directs the tip of the access device 144 to the insertion site 266 of the vessel 200. The vascular access port 100 thus can direct the access device 144 to the same insertion site 266 via which the vessel lumen 262 was accessed in the first access event.

Figure 11D:
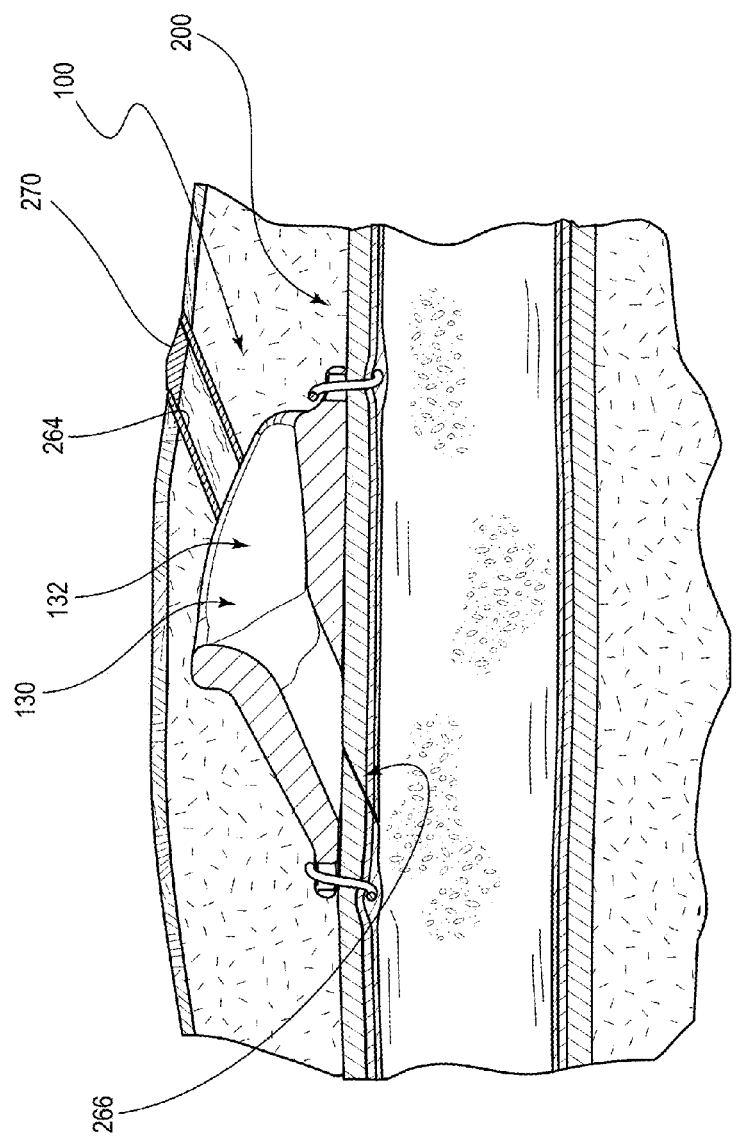
FIG. 11D is a cross-sectional view of another stage of the method of FIG. 11A in which an insertion tract and a buttonhole access site have been formed.

FIG. 11D depicts the insertion tract 264 and the insertion site 266 after multiple access events. As shown, the insertion tract 264 may become more well-defined over time, which may, for example, result from the formation of scar tissue or connective tissue. Similarly, the insertion site 266 may become more well-defined over time such that it may become easier to insert an access device 144 therethrough. Such an insertion site 266 through a vessel wall can be referred to as a buttonhole access site, or more commonly, as a buttonhole. Accordingly, the insertion site 266 may also be referred to herein as a buttonhole 266. In some embodiments, the well-defined insertion tract 264 and/or the buttonhole 266 may be established after 6, 7, 8, 9, or 10 access events.

In other embodiments, the insertion tract 264 and the buttonhole 266 can be formed by inserting an over-the-needle catheter (not shown) through the vascular access port 100. The needle portion can be removed and the catheter portion can be left in place until the insertion tract 264 is well-defined. The catheter then can be removed.

As previously discussed, the vascular access port 100 and the vessel 200 may shift relative to the insertion tract 264 between access events. However, in certain embodiments, the funnel region 132 of the guidance passageway 130 is sufficiently large that a distal end of the insertion tract 264 opens into, or extends through at least a portion of, the funnel region 132 despite any such shifting. Accordingly, the vascular access port 100 may act as a mobile extension of the insertion tract 264, which is configured to ensure that access devices 144 are consistently directed to the buttonhole 266, despite any relative movement between the insertion tract 264 and the vessel 200. In some instances, however, relatively little shifting may occur between the insertion tract 264 and the vascular access port 100, and an access device 144 may be inserted through the insertion tract 264 and directly into the channel 134 with little or no contact with the funnel region 132.

FIG. 11D also illustrates that a scab 270 may form over the insertion tract 264 between access events. The scab 270 may be removed prior to an access event. In other embodiments, a synthetic covering may be provided over or in place of the scab 270.

Figure 11E:
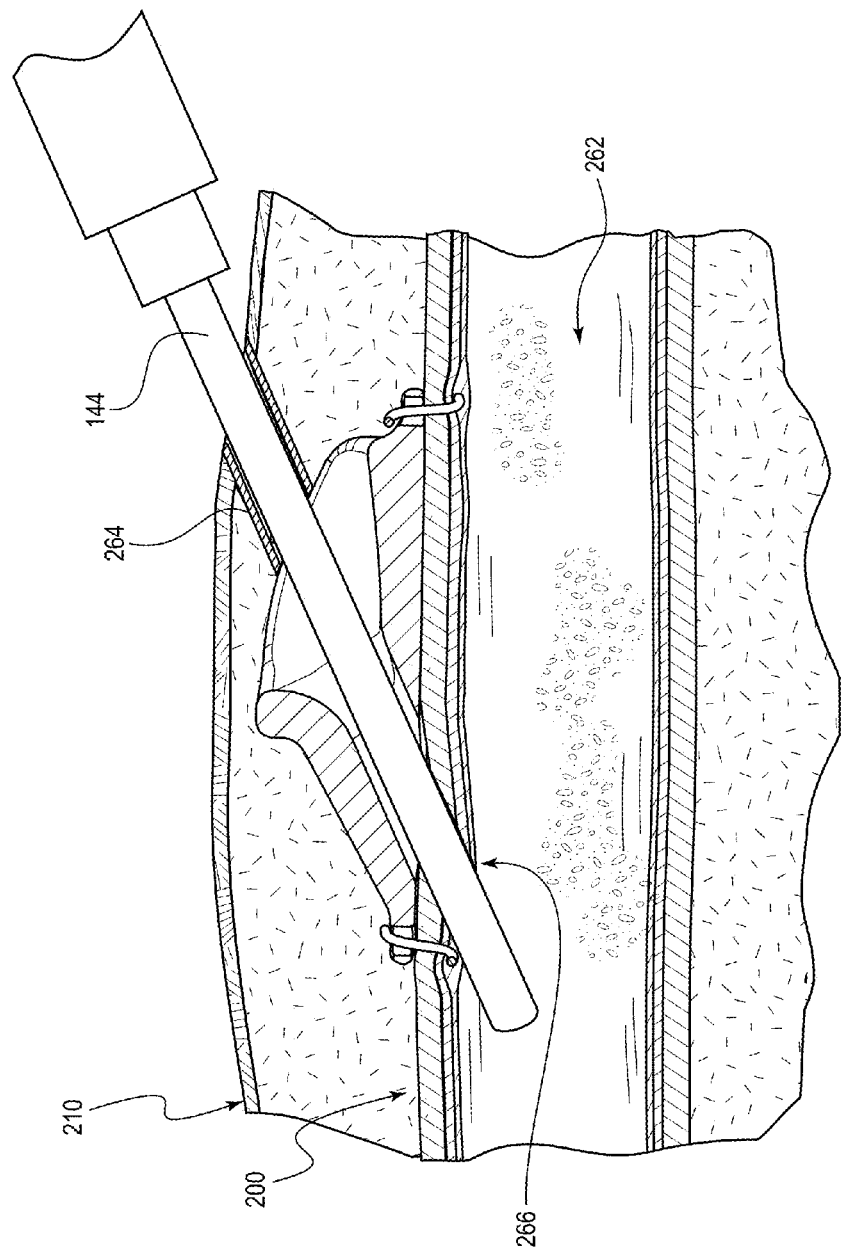
FIG. 11E is a cross-sectional view of another stage of the method of FIG. 11A in which a needle having a blunt tip is inserted into the lumen of the vessel via the insertion tract, the vascular access port, and the buttonhole access site.

FIG. 11E illustrates the use of an access device 144 having a blunt distal end after proper formation of the insertion tract 264 and the buttonhole 266. The blunt end of the access device 144 can guide the device 144 through the insertion tract 264 and through the buttonhole 266, and may do so in a less traumatic or more comfortable manner for the patient 210. Use of a blunt-tipped access device 144 also can reduce the risk of striking through an opposing side of the vessel 200.

As previously mentioned, in some embodiments, an over-the needle catheter can be used with an implanted vascular access port 100. In certain procedures, a needle/catheter assembly can be inserted through the insertion tract 264 into the vessel 200 (e.g., the jugular vein) and then the catheter can be advanced through the vessel to the desired position (e.g., the superior vena cava for certain central venous system applications). An infusion or other desired procedure can then be conducted. The catheter can be removed from the patient after completion of the procedure.

Figure 12:
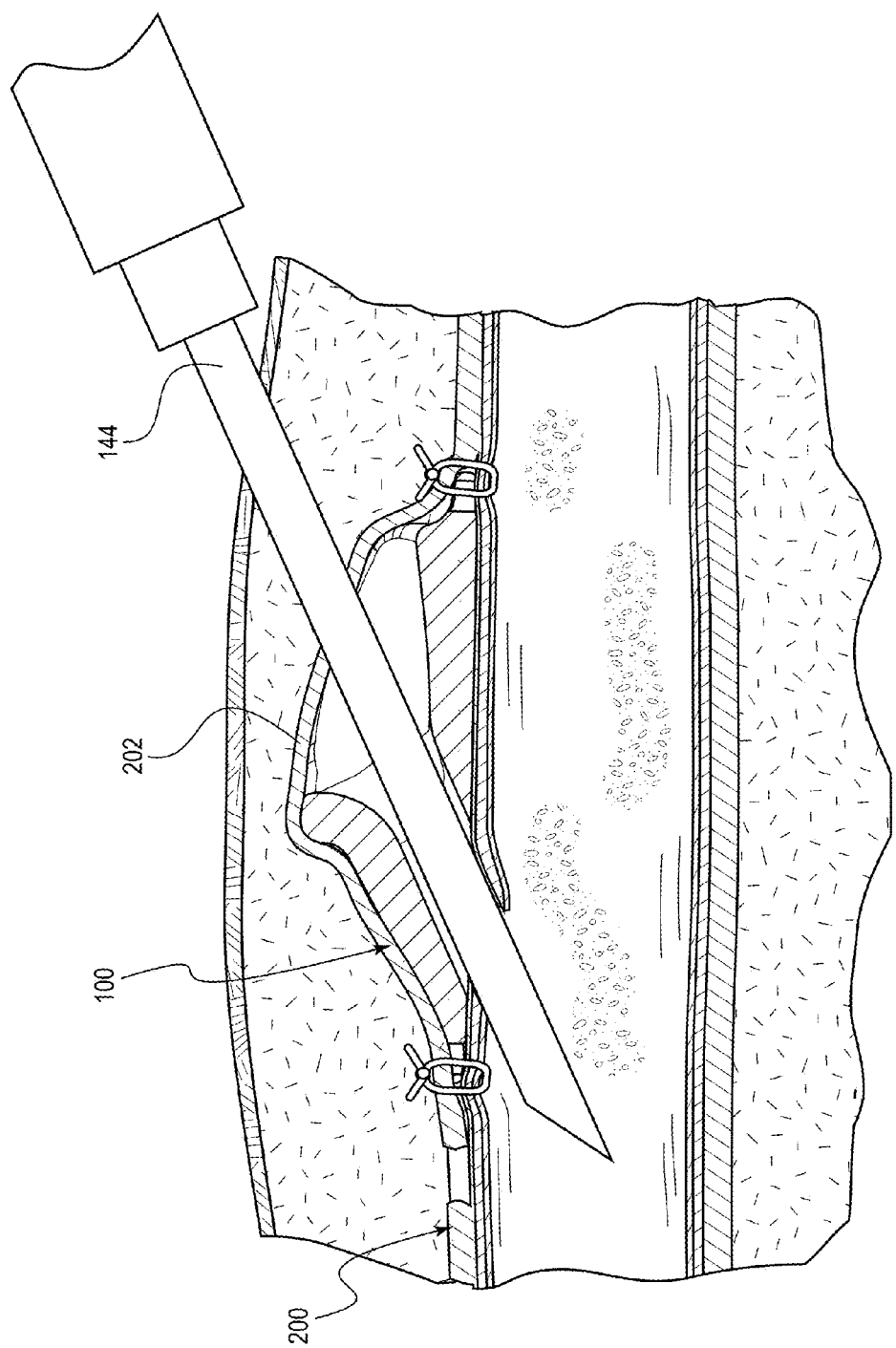
FIG. 12 is a cross-sectional view of a stage of another illustrative method relating to the creation and use of a buttonhole access site to access a lumen of a vessel.

FIG. 12 depicts an embodiment of the vascular access port 100 that has been implanted in the patient 210 via a method such as that depicted in FIGS. 10A-10G. A portion of the adventitia layer 202 of the vessel 200 thus extends over the vascular access port 100. Accordingly, when an access device 144 is inserted into the vessel 200 via the access port 100, it passes through the adventitia layer 202 before entering the vascular access port 100. Otherwise, procedures for creating and using buttonholes can be similar to those described above with respect to FIGS. 11A-11E.

Figure 13:
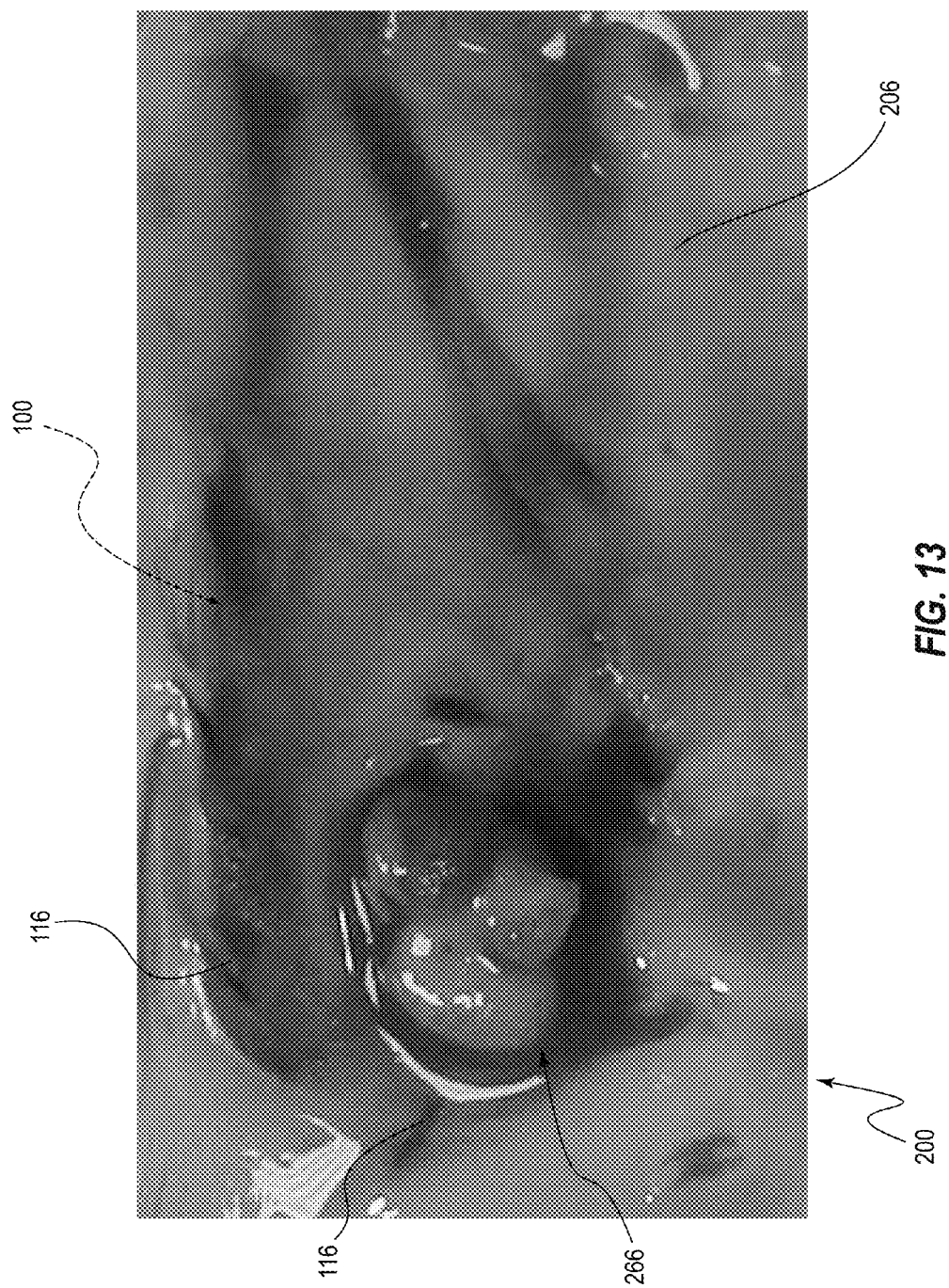
FIG. 13 is a bottom plan view of a filleted vessel that bears an embodiment of a buttonhole access site that has been created via an embodiment of a vascular access port.

FIG. 13 depicts an illustrative example of an embodiment of a buttonhole access site 266 in a vessel 200 that was formed by repeated insertion of access devices 144 through an embodiment of a vascular access port 100. FIG. 13 is a photograph of a filleted portion of the vessel 200, and is shown from a bottom plan view thereof (i.e., a view directed toward the intima layer 206). A contour of the vascular access port 100 is visible in the photograph, as are portions of a running suture 116 that extend through the initima layer 206.

In this particular example, the vascular access port 100 was implanted in a sheep for a period of 9 weeks. After a waiting period to permit for tissue ingrowth, a sharp needle was inserted through the vascular access port 100 to access the vessel 200. Six (6) additional access events were conducted thereafter using a sharp needle, followed by twelve (12) access events using a blunt needle. Accordingly, a total of nineteen (19) cannulations were performed. The access events were conducted at a frequency of three per week.

Figure 14A:
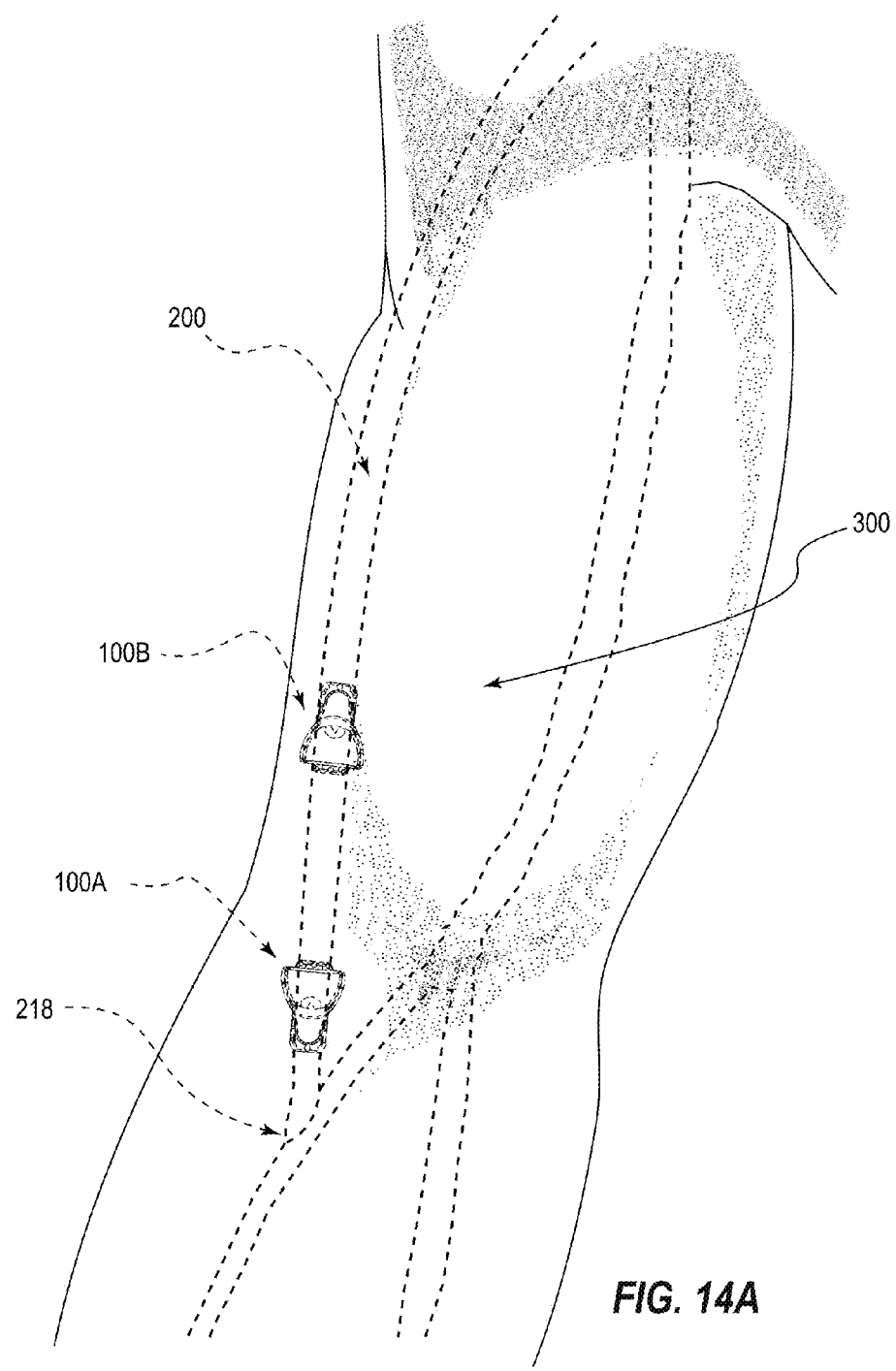
FIG. 14A is a perspective view of an embodiment of a vascular access system that can be used for hemodialysis.

FIG. 14A depicts an embodiment of a hemodialysis system 300 that includes two vascular access ports 100A, 100B. Both of the ports 100A, 100B are shown attached to a vessel 200 that is associated with an arteriovenous fistula 218. One port 100A is directed upstream such that a forward end thereof points in a direction opposite to the flow of blood through the vessel 200, and the other port 100B is directed downstream such that a forward end thereof points in the direction of the blood flow through the vessel 200. A fistula needle may be introduced into each of the ports 100A, 100B and hemodialysis performed. The first port 100A can be an uptake port through which blood is removed from the vessel 200 and delivered to a hemodialysis machine, and the second port 100B can be a return port through which filtered blood is returned to the vessel 200 from the hemodialysis machine.

In other embodiments, the hemodialysis system 300 can comprise only a single vascular access port 100A or 100B. Hemodialysis may be conducted thereby via any suitable method, such as a single-needle hemodialysis technique.

In still other embodiments, the hemodialysis system 300 includes more than two vascular access ports 100A, 100B. A clinician thus can rotate among the ports 100A, 100B, thereby leaving one or more of the ports unused during any given hemodialysis session.

Figure 14B:
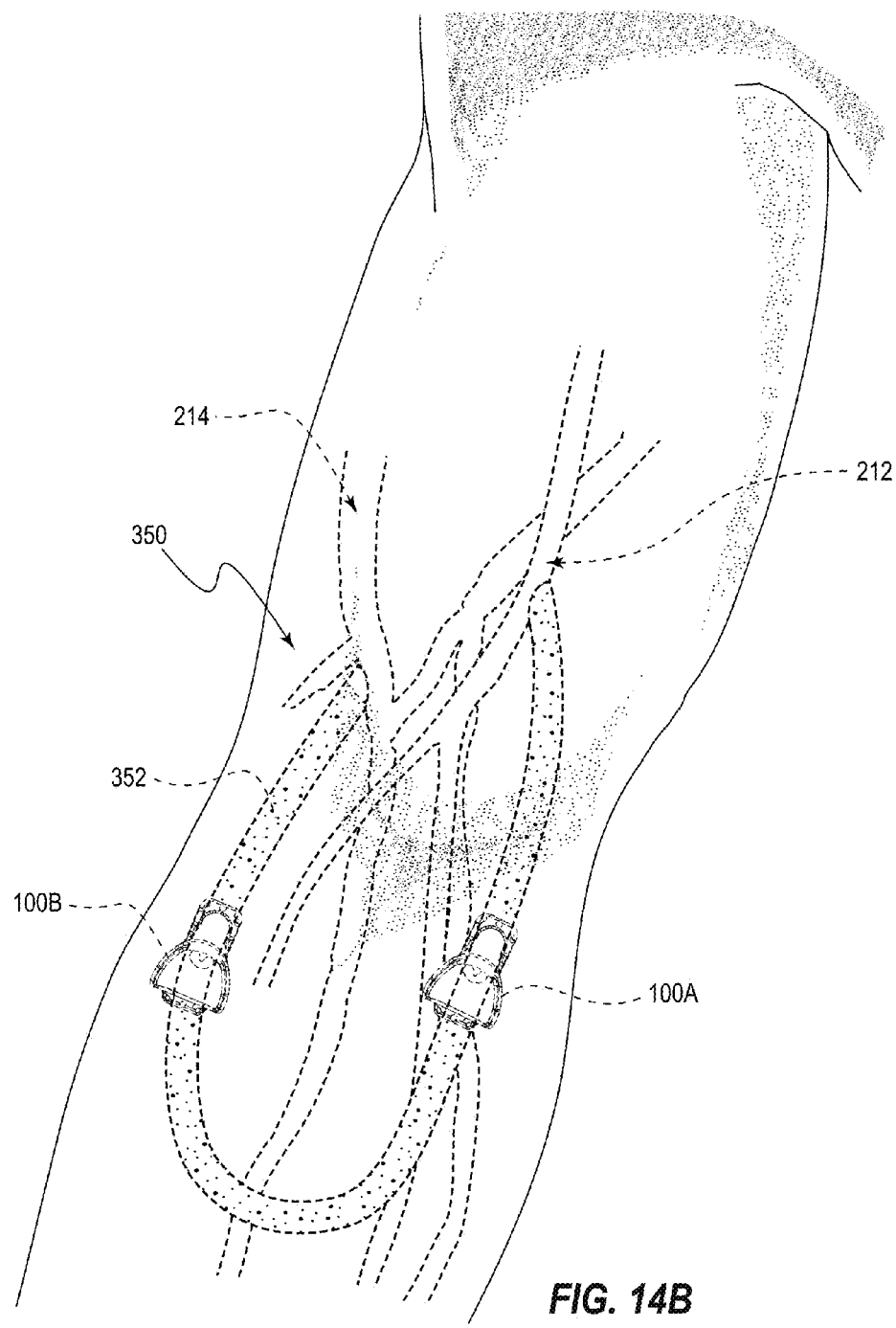
FIG. 14B is a perspective view of another embodiment of a vascular access system that can be used for hemodialysis.
Figure 15A:
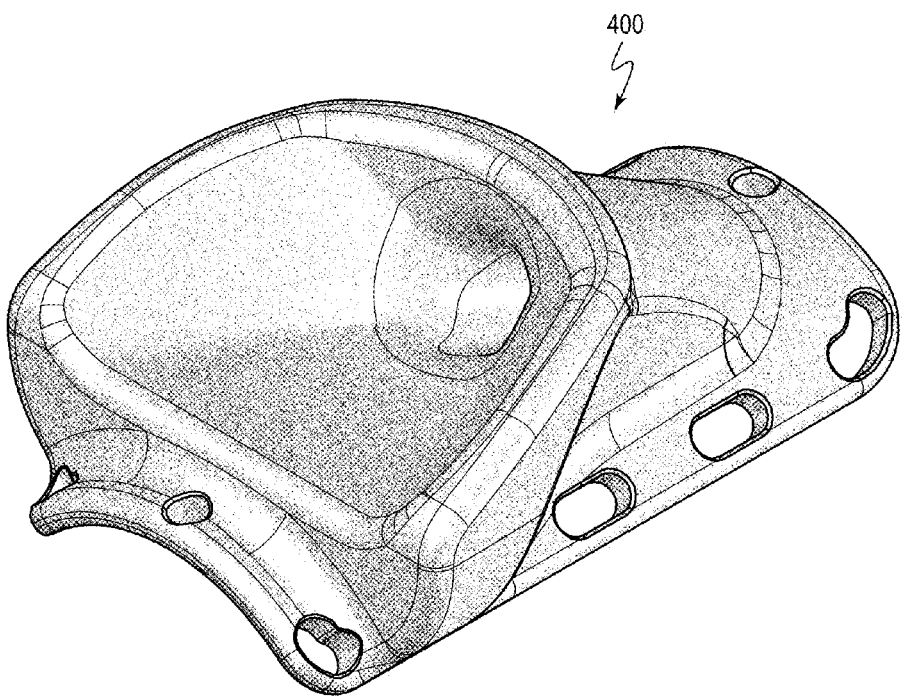
FIG. 15A is a perspective view of another embodiment of a vascular access port.
Figure 15B:
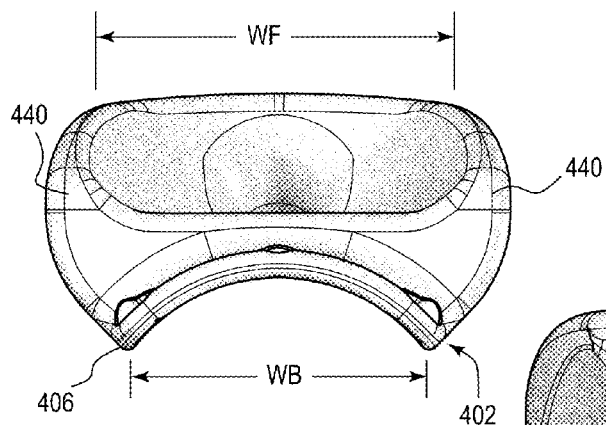
FIG. 15B is a rear elevation view thereof.
Figure 15C:
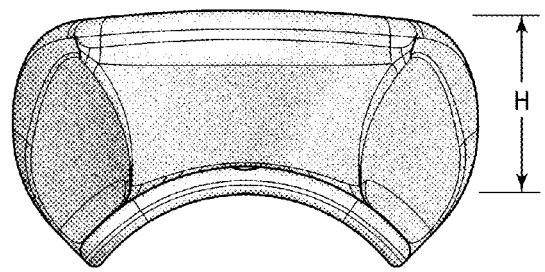
FIG. 15C is a front elevation view thereof.
Figure 15D:
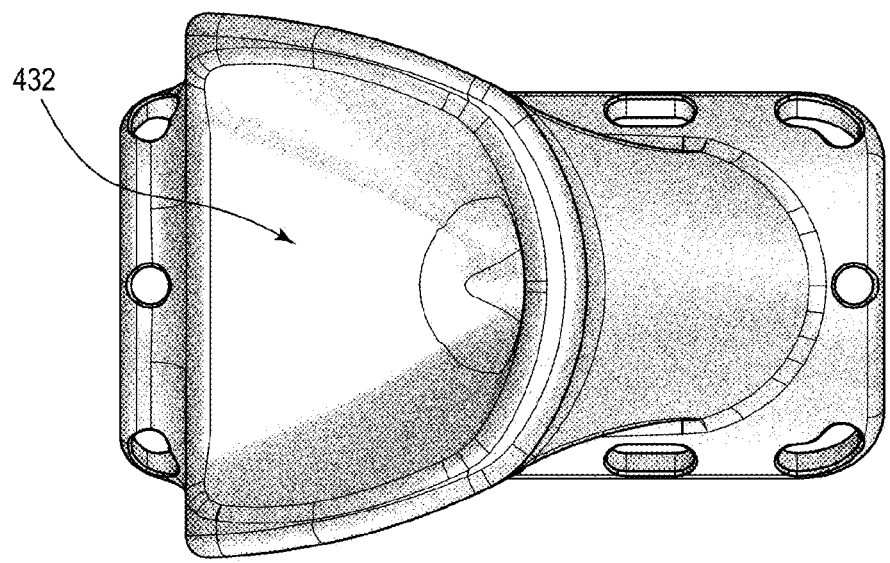
FIG. 15D is a top plan view thereof.
Figure 15E:
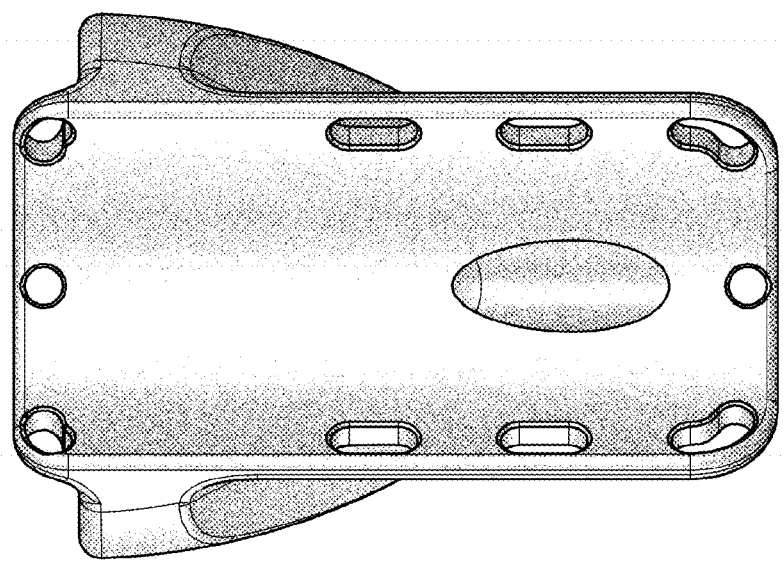
FIG. 15E is a bottom plan view thereof.
Figure 15F:
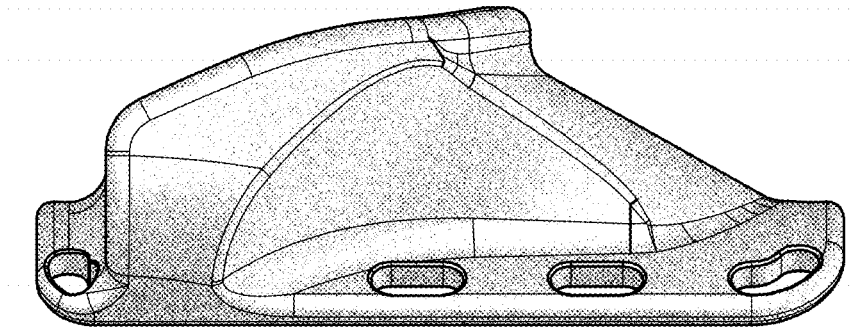
FIG. 15F is a right side elevation view thereof, wherein a left side elevation view is a mirror image of the right side elevation view.
Figure 15G:
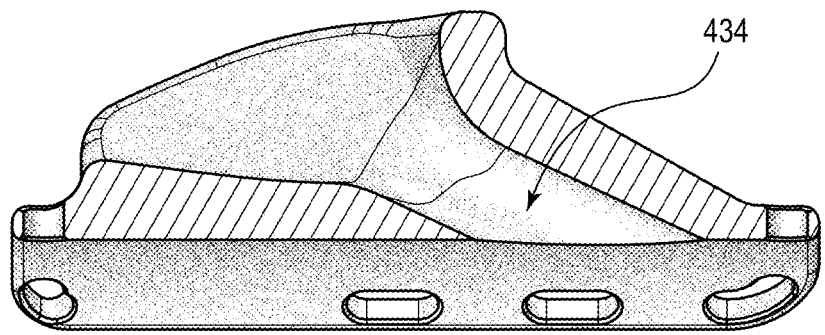
FIG. 15G is a cross-sectional view thereof.
Figure 16A:
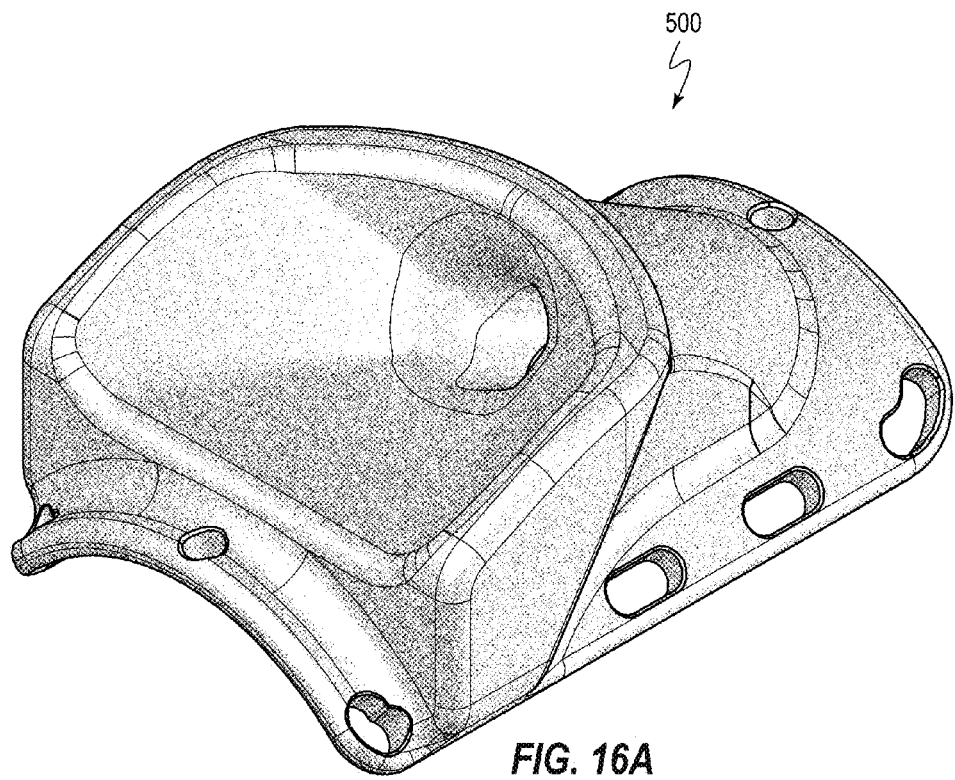
FIG. 16A is a perspective view of another embodiment of a vascular access port.
Figure 16B:
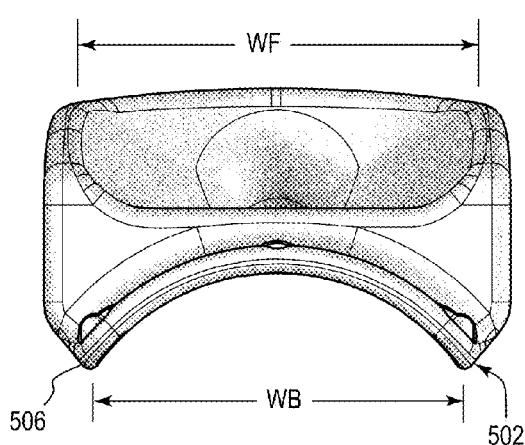
FIG. 16B is a rear elevation view thereof.
Figure 16C:
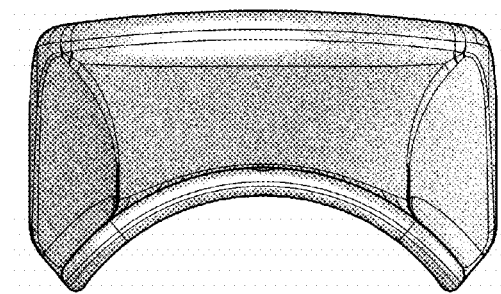
FIG. 16C is a front elevation view thereof.
Figure 16D:
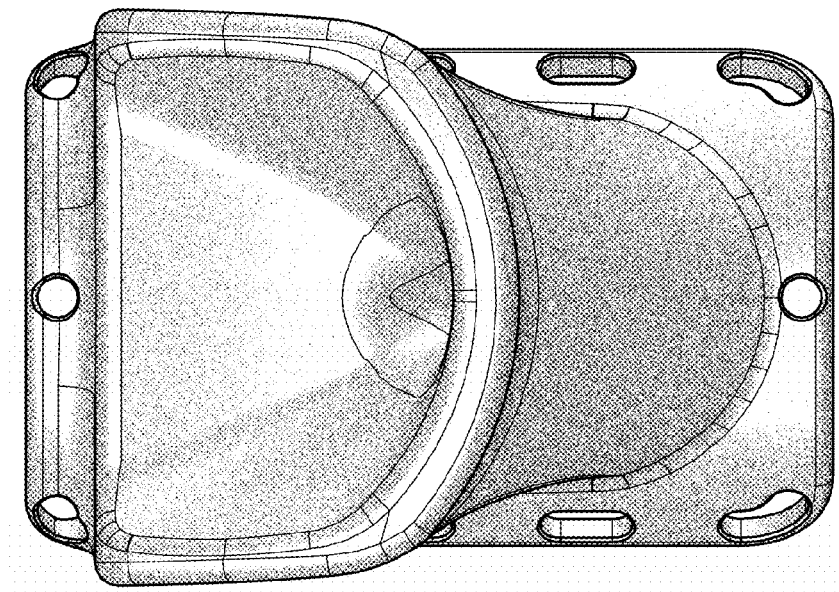
FIG. 16D is a top plan view thereof.
Figure 16E:
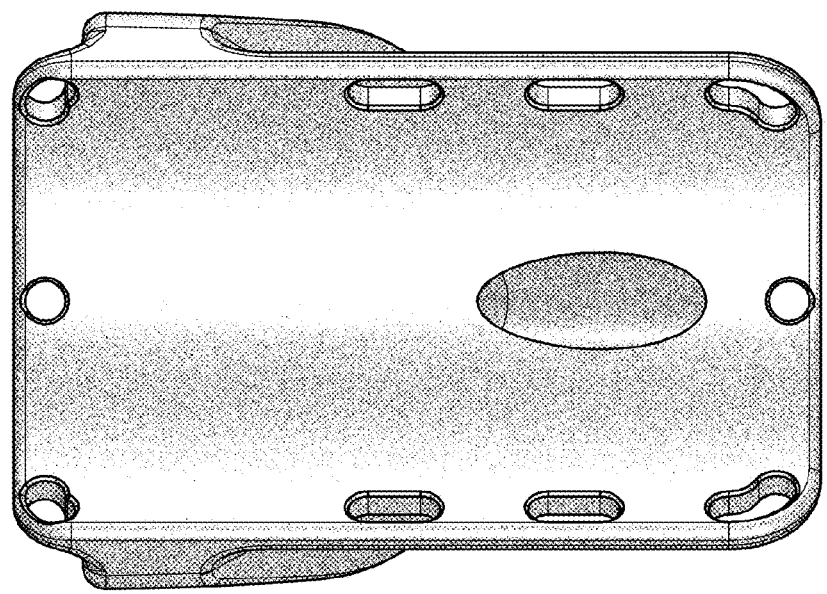
FIG. 16E is a bottom plan view thereof.
Figure 16F:
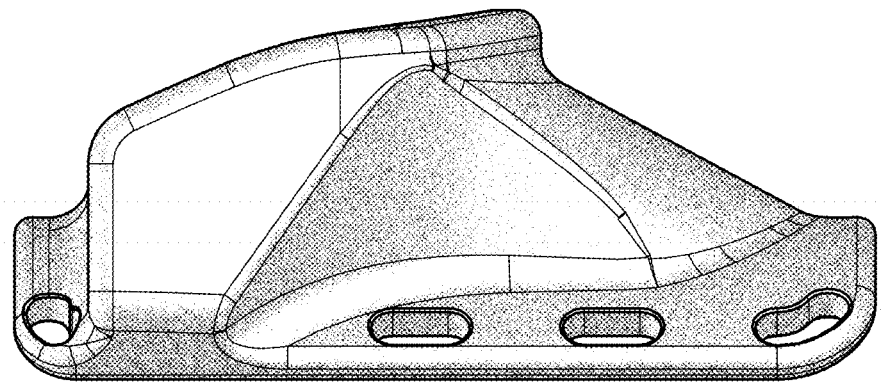
FIG. 16F is a right side elevation view thereof, wherein a left side elevation view is a mirror image of the right side elevation view.
Figure 16G:
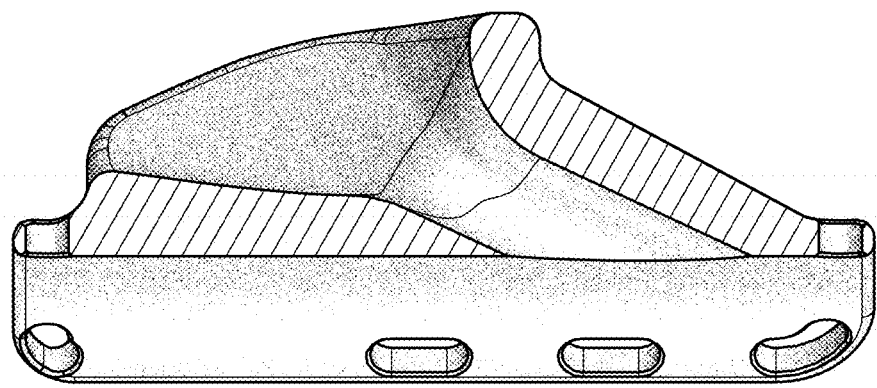
FIG. 16G is a cross-sectional view thereof.

FIG. 14B depicts another embodiment of a hemodialysis system 350. The illustrated embodiment includes two vascular access ports 100A, 100B, but more or fewer ports are possible. Both of the ports 100A, 100B are shown attached to an artificial graft vessel 352 that serves as a shunt between an artery 212 and a vein 214. The graft vessel 352 can comprise any suitable material, such as e-PTFE. The ports 100A, 100B can be attached to the graft vessel 352 prior to its implantation, or may be attached to the graft vessel 352 after it has been implanted. The hemodialysis system 350 can function similarly to the system 300 described above, with the port 100A serving as an uptake port and the port 100B serving as a return port.

FIGS. 15A-15G illustrate another embodiment of a vascular access port 400, which can resemble the vascular access port 100 described above in certain respects. Accordingly, like features are designated with like reference numerals, with the leading digits incremented to "4." Relevant disclosure set forth above regarding similarly identified features thus may not be repeated hereafter. Moreover, specific features of the vascular access port 400 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the vascular access port 400. Any suitable combination of the features and variations of the same described with respect to the vascular access port 100 can be employed with the vascular access port 400, and vice versa. This pattern of disclosure applies equally to further embodiments depicted in subsequent figures and described hereafter.

A width WF of the vascular access port 400 can be approximately the same as the width WF of the vascular access port 100, but a width WB thereof may be somewhat larger than the width WB of the vascular access port 100. Accordingly, wings 440 may extend past a perimeter 406 of a base 402 to a lesser extent than do the wings 140 of the port 100. Additionally, a radius of curvature of the base 402 can be larger than a radius of curvature of the base 102. A height H of the port 400 may be approximately the same as the height H of the port 100.

The port 400 thus can be configured for use with a somewhat larger vessel than the port 100. However, the port 400 can be implanted in a patient at approximately the same depth as the port 100 without substantially changing an observable profile at the surface of the skin of the patient, and can define a funnel region 432 that is only slightly larger than the funnel region 132. Moreover, a channel 434 through the port 400 can be about the same size and configuration (including an angle thereof relative to the base 402) as the channel 134. The port 400 thus may be configured for use with the same type of vessel as the port 100, but with a different patient who may have larger vessels. By way of example, the port 100 may be configured for use with vessels having an outer diameter of approximately 7 millimeters, whereas the port 400 may be configured for use with vessels having an outer diameter of approximately 9 millimeters. Similar methods for implantation and use thus may be performed for each port 100, 400.

A system for providing a selection of vascular access ports for a given use thus may comprise both of the ports 100, 400. For example, a distributor may offer both types of ports 100, 400 as alternatives to accommodate varying needs of a customer, and/or may deliver one or both ports 100, 400 to a customer.

FIGS. 16A-16G illustrate another embodiment of a vascular access port 500, which can resemble the vascular access ports 100, 400 described above in certain respects. A width WF of the vascular access port 500 can be approximately the same as the width WF of the vascular access port 400, but a width WB thereof may be somewhat larger than the width WB of the vascular access port 400. Accordingly, wings 540 may extend past a perimeter 506 of a base 502 to a lesser extent than do the wings 440 of the port 400. Additionally, a radius of curvature of the base 502 can be larger than a radius of curvature of the base 402. A height H of the port 500 may be approximately the same as the height H of the port 400.

The port 500 thus can be configured for use with a somewhat larger vessel than the port 400, and may be configured for use with the same type of vessel as the ports 100, 400 but with a different patient who may have larger vessels. By way of example, the port 500 may be configured for use with vessels that have an outer diameter of approximately 11 millimeters.

A system for providing a selection of vascular access ports for a given use thus may comprise any combination of the ports 100, 400, 500. For example, a distributor may offer two or more of the ports 100, 400, 500 as alternatives to accommodate varying needs of a customer, and/or may deliver one or more of the ports 100, 400, 500 to a customer.

FIGS. 17A-17G illustrate another embodiment of a vascular access port 600, which can resemble the vascular access ports described above in certain respects. The vascular access port 600 can comprise a base 602 that is devoid of attachment passages. Accordingly, the port 600 may be attached to a vessel by some method other than suturing or the like, such as via a biocompatible adhesive. However, in other embodiments, the vascular access port 600 includes attachment passages such as the attachment passages 114 discussed above.

The port 600 can include a guidance passageway 630 that varies from the guidance passageway 130 depicted in FIGS. 1-7. In particular, the guidance passageway 630 comprises a funnel region 632 that extends from a palpation projection 646 to an opening 650 in the base 602. Stated otherwise, the passageway 630 does not include a channel. In some instances, the absence of a channel can prevent or inhibit binding of an access device 144 as it is inserted through the passageway 630. On the other hand, in some instances, the absence of a channel can result in less constraint on an orientation of the access device 144 as it passes through the opening 650, which may complicate the creation or use of a buttonhole in the wall of a vessel.

Figure 17A:
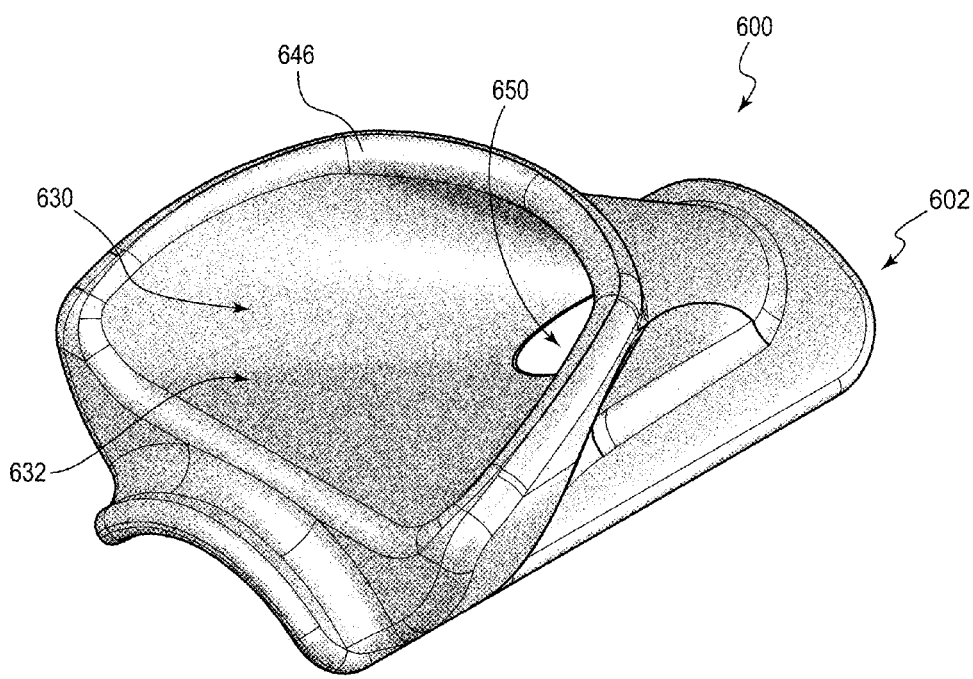
FIG. 17A is a perspective view of another embodiment of a vascular access port.
Figure 17B:
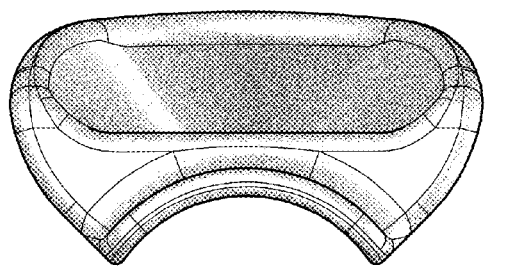
FIG. 17B is a rear elevation view thereof.
Figure 17C:
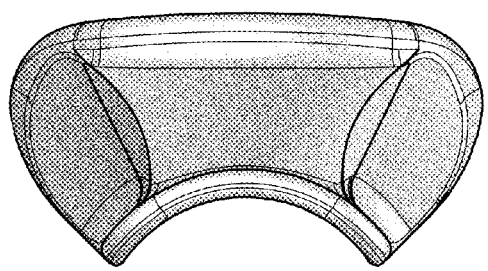
FIG. 17C is a front elevation view thereof.
Figure 17D:
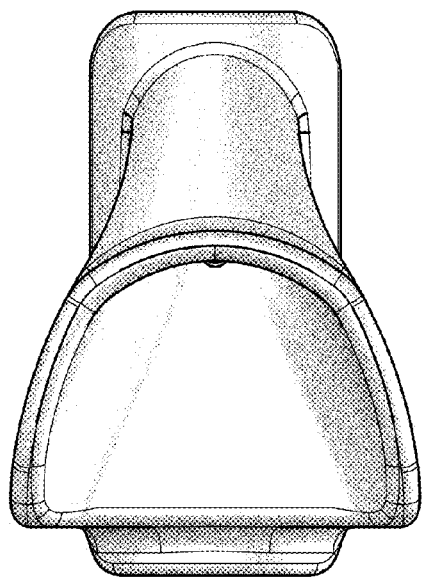
FIG. 17D is a top plan view thereof.
Figure 17E:
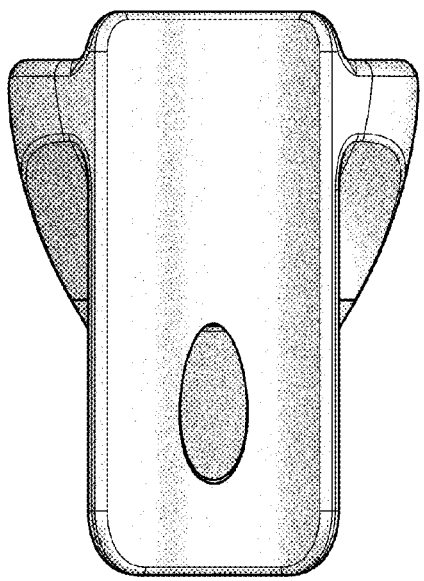
FIG. 17E is a bottom plan view thereof.
Figure 17F:
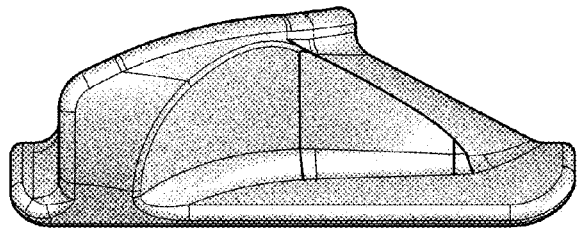
FIG. 17F is a right side elevation view thereof, wherein a left side elevation view is a mirror image of the right side elevation view.
Figure 17G:
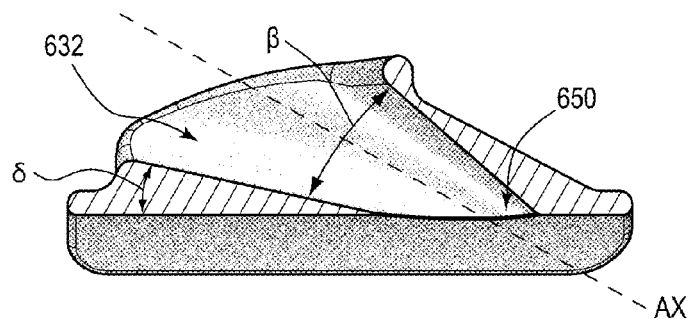
FIG. 17G is a cross-sectional view thereof.
Figure 18A:
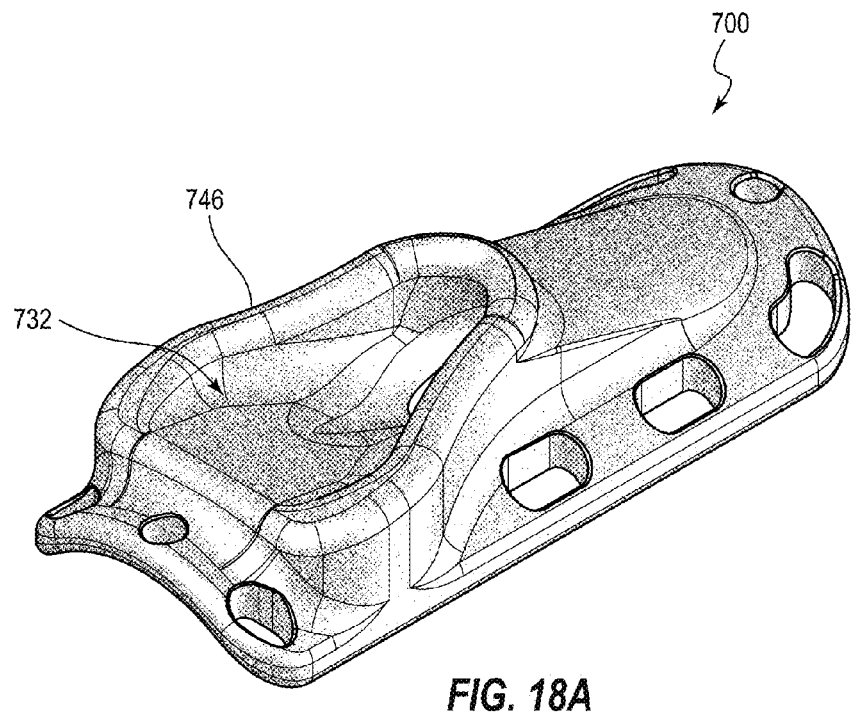
FIG. 18A is a perspective view of another embodiment of a vascular access port.
Figure 18B:
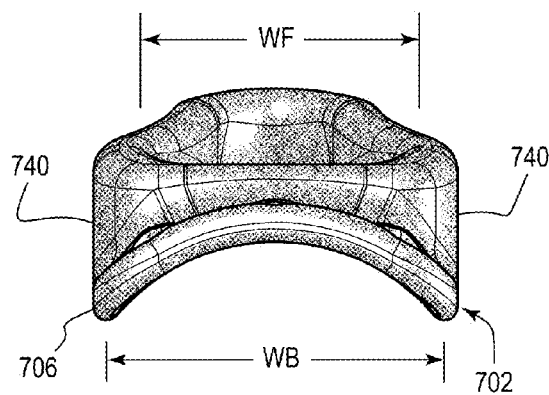
FIG. 18B is a rear elevation view thereof.
Figure 18C:
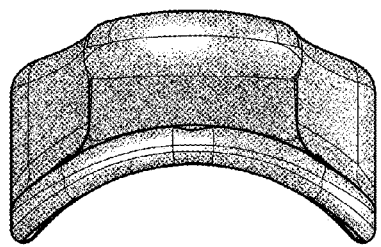
FIG. 18C is a front elevation view thereof.
Figure 18D:
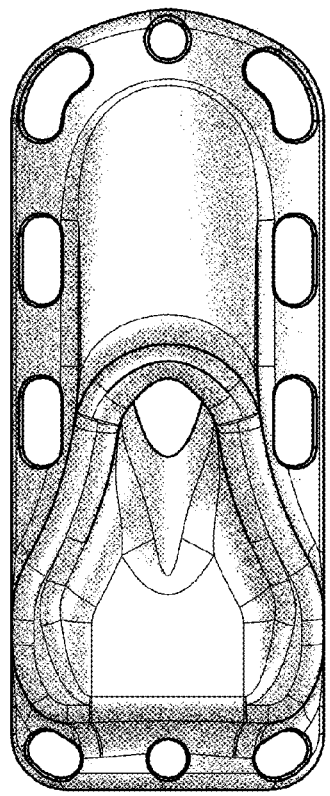
FIG. 18D is a top plan view thereof.
Figure 18E:
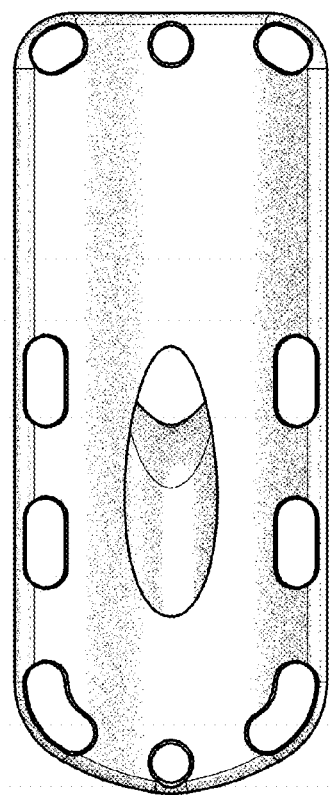
FIG. 18E is a bottom plan view thereof.
Figure 18F:
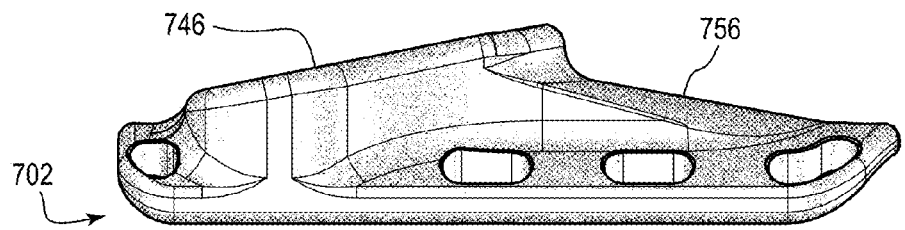
FIG. 18F is a right side elevation view thereof, wherein a left side elevation view is a mirror image of the right side elevation view.
Figure 18G:
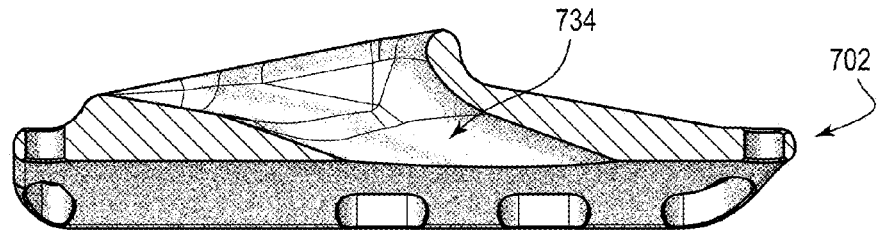
FIG. 18G is a cross-sectional view thereof.
Figure 19A:
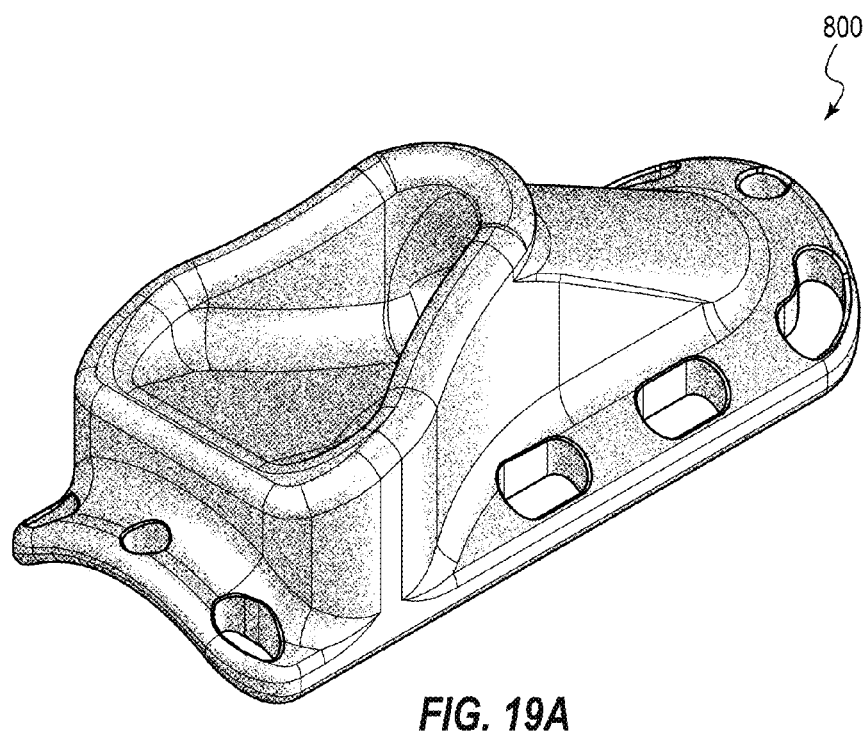
FIG. 19A is a perspective view of another embodiment of a vascular access port.
Figure 19B:
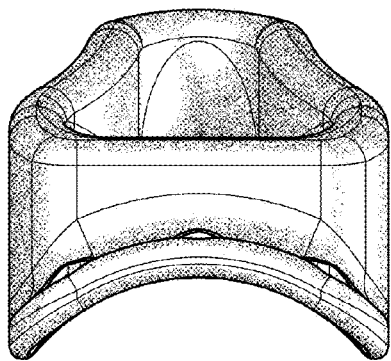
FIG. 19B is a rear elevation view thereof.
Figure 19C:
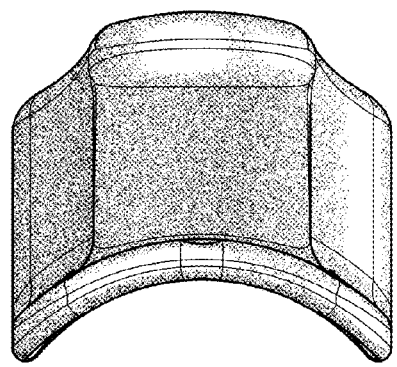
FIG. 19C is a front elevation view thereof.
Figure 19D:
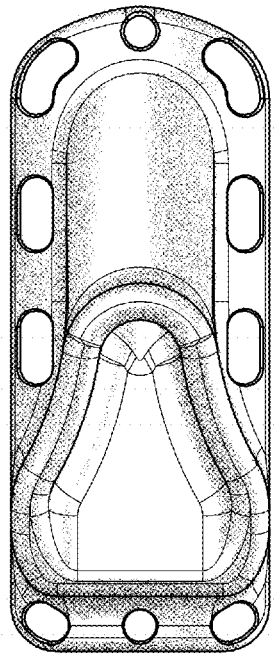
FIG. 19D is a top plan view thereof.
Figure 19E:
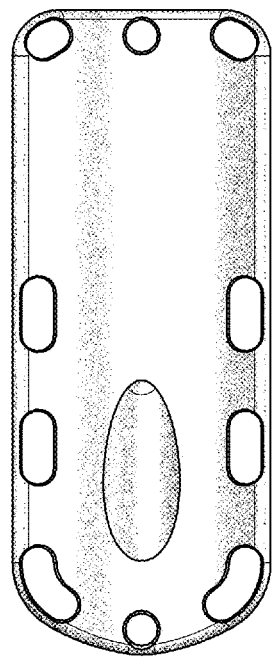
FIG. 19E is a bottom plan view thereof.
Figure 19F:
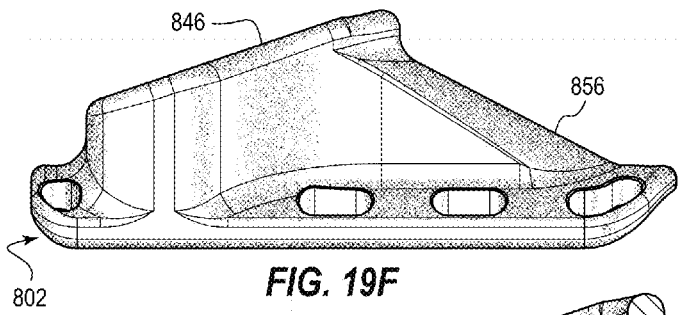
FIG. 19F is a right side elevation view thereof, wherein a left side elevation view is a mirror image of the right side elevation view.
Figure 19G:
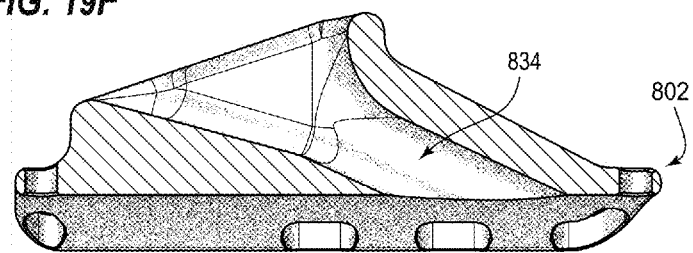
FIG. 19G is a cross-sectional view thereof.
Figure 20D:
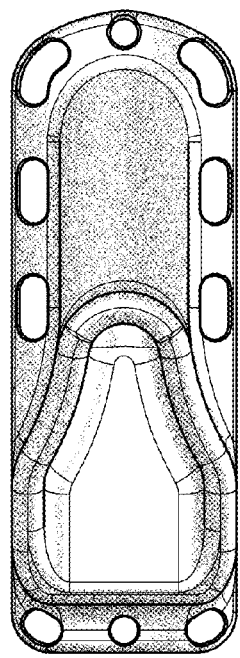
FIG. 20D is a top plan view thereof.
Figure 20E:
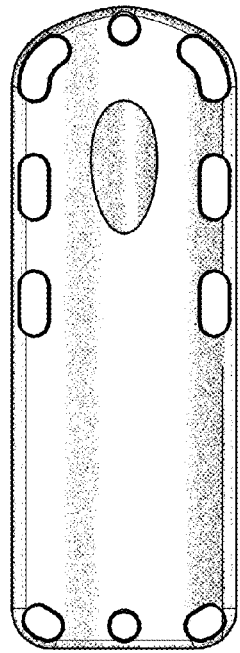
FIG. 20E is a bottom plan view thereof.
Figure 20F:
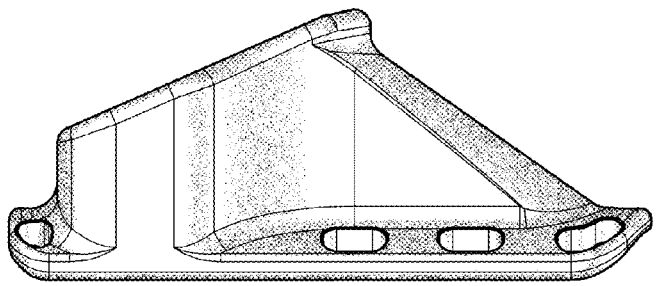
FIG. 20F is a right side elevation view thereof, wherein a left side elevation view is a mirror image of the right side elevation view.
Figure 20G:
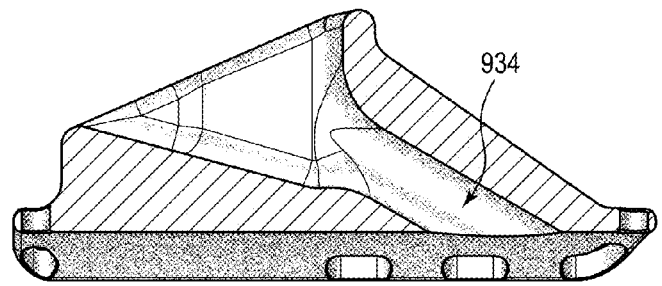
FIG. 20G is a cross-sectional view thereof.
Figure 21A:
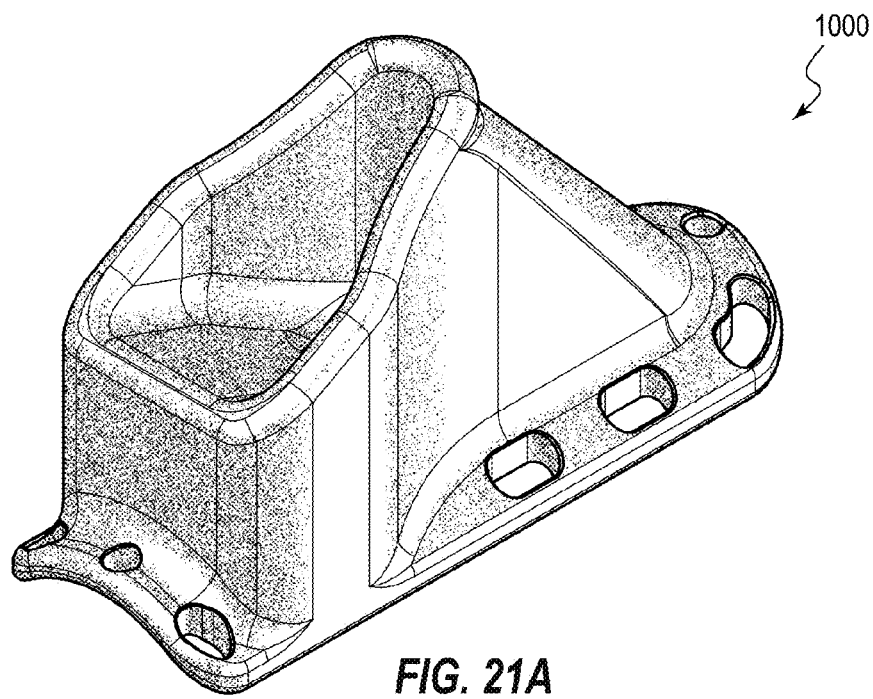
FIG. 21A is a perspective view of another embodiment of a vascular access port.
Figure 21B:
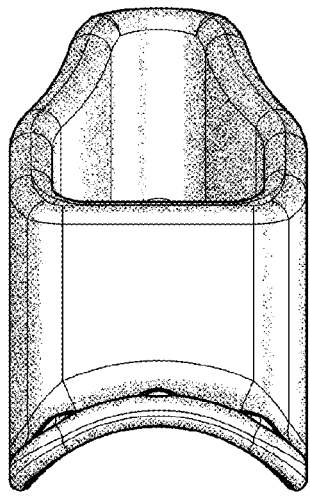
FIG. 21B is a rear elevation view thereof.
Figure 21C:
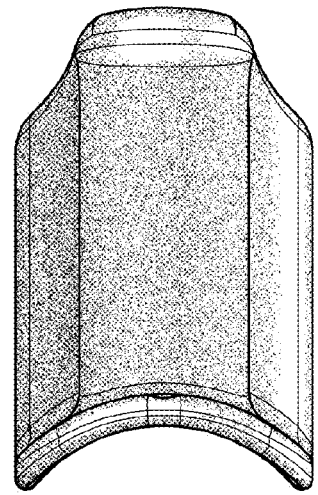
FIG. 21C is a front elevation view thereof.
Figure 21D:
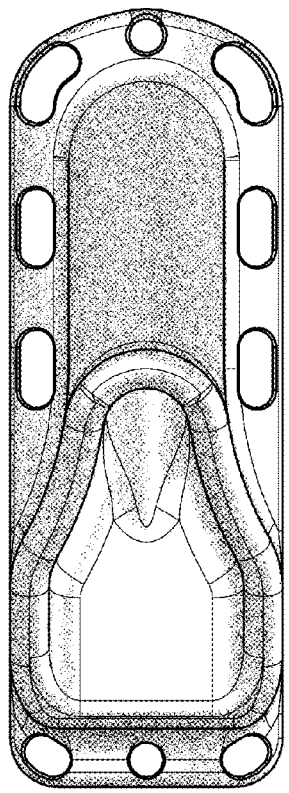
FIG. 21D is a top plan view thereof.
Figure 21E:
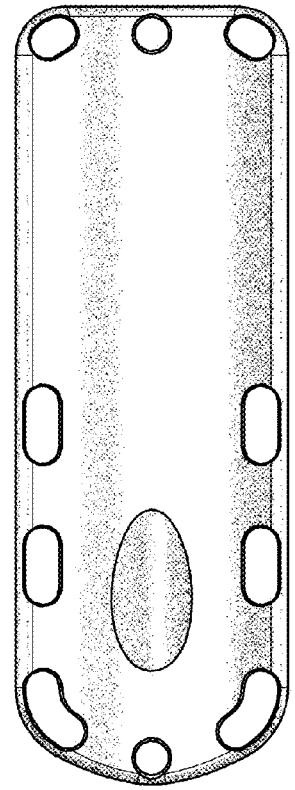
FIG. 21E is a bottom plan view thereof.
Figure 21F:
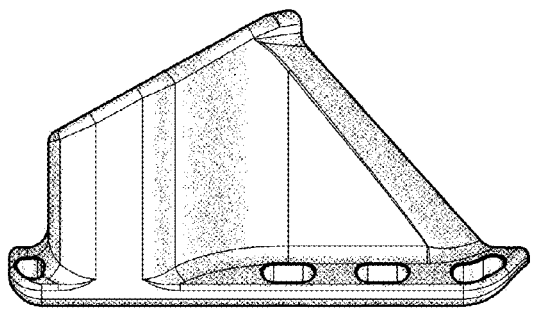
FIG. 21F is a right side elevation view thereof, wherein a left side elevation view is a mirror image of the right side elevation view.
Figure 21G:
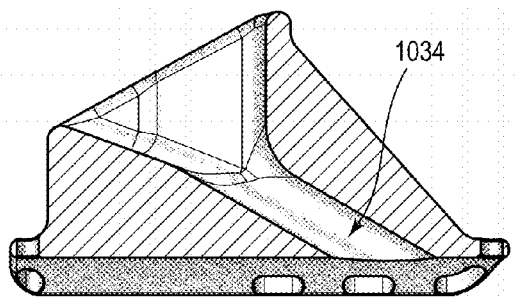
FIG. 21G is a cross-sectional view thereof.

The funnel region 632 can define multiple angles relative to the base 602. With reference to FIG. 17G, which represents a cross-section of the port 600 along a central vertical medial plane thereof, a front surface of the funnel region 632 can define a maximum angle $\beta$ relative to the base 602, and a rear surface of the funnel region 632 can define a minimum angle $\gamma$ relative to the base 602. A central axis AX of the guidance passageway 630 can pass through a center of the opening 650 along the central vertical medial plane at an angle relative to the base that has a value defined by $(\beta+\gamma)/2$.

FIGS. 18A-18G illustrate another embodiment of a vascular access port 700, which can resemble the vascular access ports described above in certain respects. A width WF of the vascular access port 700 can be less than a width WB thereof. Accordingly, wings 740 of the port 700 may not extend past a perimeter 706 of a base 702. In the illustrated embodiment, the outer edges of the wings 740 are substantially parallel to each other and extend upwardly from the base 702.

The port 700 can include a palpation projection 746 that fully encompasses a funnel region 732 of the port. As shown, for example, in FIG. 18F, the palpation projection 746 can be substantially planar, and only a small portion thereof may deviate from the plane defined thereby. A plane defined by the palpation projection 746 can define an acute angle relative to a bottom end of the base 702. Additionally, a forward face 756 of the port 700 can define an acute angle relative to the bottom end of the base 702. In the illustrated embodiment, the port 700 includes a channel 734 that defines an acute angle relative to the base 702.

FIGS. 19A-19G illustrate another embodiment of a vascular access port 800, which can resemble the vascular access ports described above in certain respects. The vascular access port 800 can particularly resemble the access port 700, but may be configured for deeper implantation within a patient. For example, in some embodiments, a base 802 of the port 800 and the base 702 of the port 700 have approximately the same width, yet the height of the port 800 can be greater than the height of the port 700. Each port 700, 800 may define a length that is approximately the same, but acute angles defined by a plane across a palpation projection 846 and by a forward face 856 of the port 800 may be greater than similar acute angles defined by a plane across the palpation projection 746 and the forward face 756 of the port 700 (compare FIGS. 18F and 19F). An angle of a channel 834 relative to the base 802 can be greater than the angle defined by the channel 734.

The port 800 thus can be configured for use with a somewhat deeper yet similarly sized vessel, as compared with the port 700. By way of example, the ports 700, 800 may each have a width of approximately 7 millimeters, yet the port 700 may have a height within a range of from about 2 millimeters to about 3 millimeters, while the port 800 may have a height within a range of from about 4 millimeters to about 5 millimeters. Similar methods for implantation and use may be performed for each port 700, 800.

Similarities and differences such as those just described with respect to the ports 700, 800 may also exist between these ports and the ports 900 and 1000, which are depicted in FIGS. 20A-20G and 21A-21G, respectively. For example, the ports 900, 1000 each may have a width of approximately 7 millimeters, yet the port 900 may have a height within a range of from about 6 millimeters to about 7 millimeters, while the port 1000 may have a height within a range of from about 9 millimeters to about 10 millimeters. In the foregoing examples, the channel 734 of the port 700 may define an angle of about 20 degrees, a channel 834 of the port 800 may define an angle of about 25 degrees, a channel 934 of the port 900 may define an angle of about 30 degrees, and a channel 1034 of the port 1000 may define an angle of about 35 degrees. In other embodiments, the channel 1034 may instead define an angle of about 30 degrees.

A system for providing a selection of vascular access ports for a given use may comprise any combination of the ports 700, 800, 900, 1000. For example, a distributor may offer two or more of the ports 700, 800, 900, 1000 as alternatives to accommodate varying needs of a customer, and/or the distributor may deliver one or both ports 700, 800, 900, 1000 to the customer.

Figure 22A:
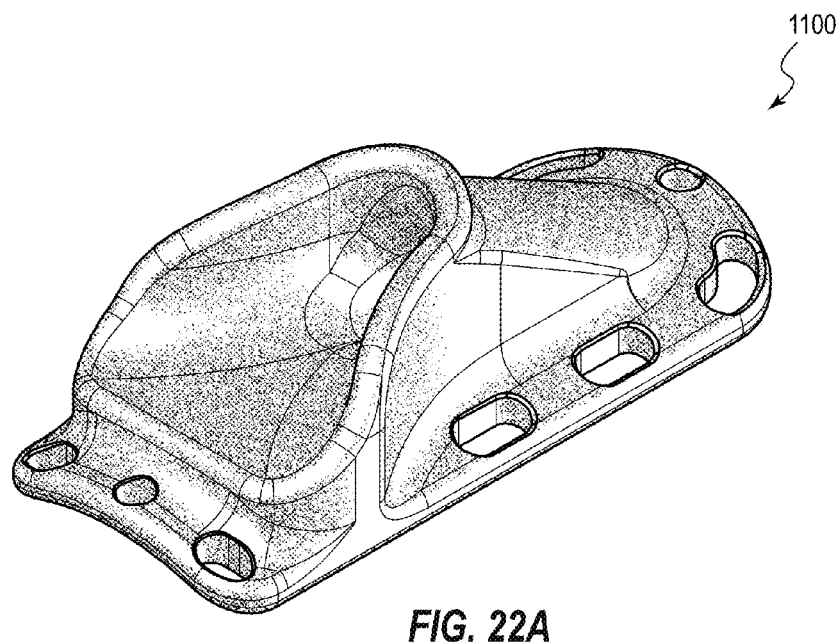
FIG. 22A is a perspective view of another embodiment of a vascular access port.
Figure 22B:
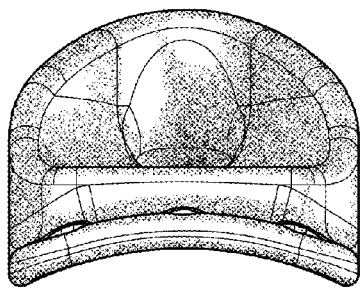
FIG. 22B is a rear elevation view thereof.
Figure 22C:
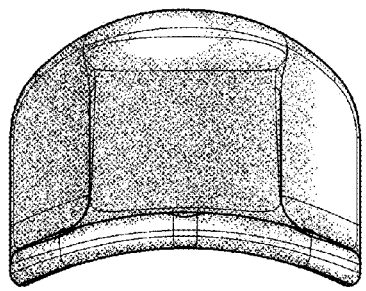
FIG. 22C is a front elevation view thereof.
Figure 22D:
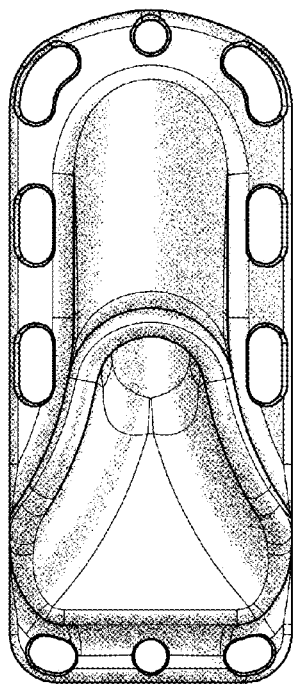
FIG. 22D is a top plan view thereof.
Figure 22E:
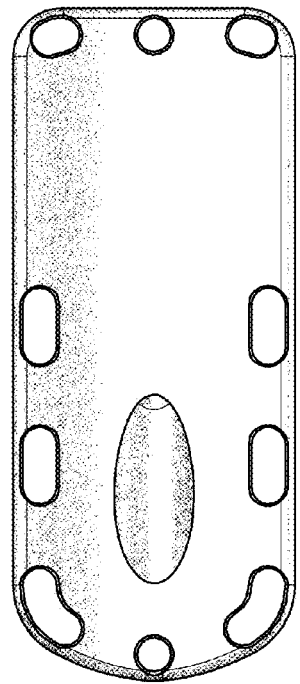
FIG. 22E is a bottom plan view thereof.
Figure 22F:
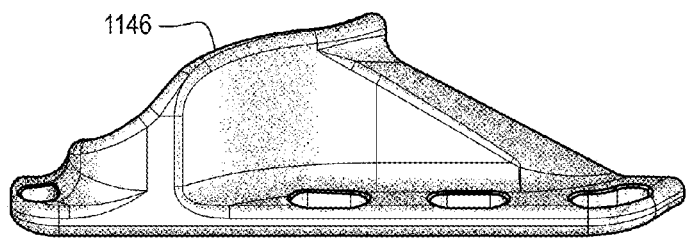
FIG. 22F is a right side elevation view thereof, wherein a left side elevation view is a mirror image of the right side elevation view.
Figure 22G:
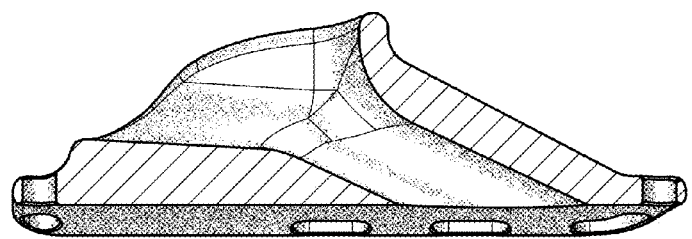
FIG. 22G is a cross-sectional view thereof.
Figure 23A:
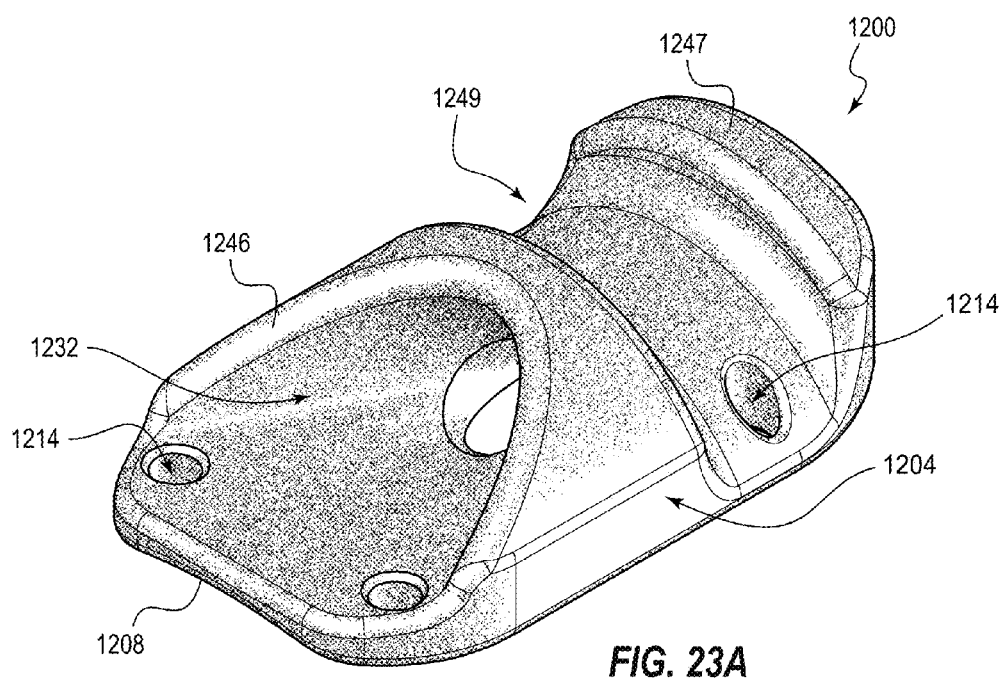
FIG. 23A is a perspective view of another embodiment of a vascular access port.
Figure 23B:
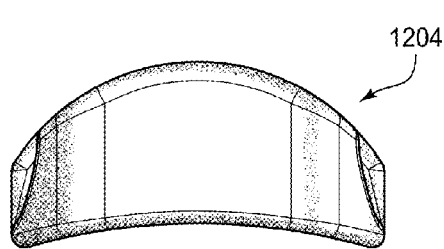
FIG. 23B is a rear elevation view thereof.
Figure 23C:
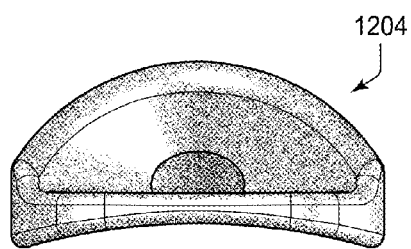
FIG. 23C is a front elevation view thereof.
Figure 23D:
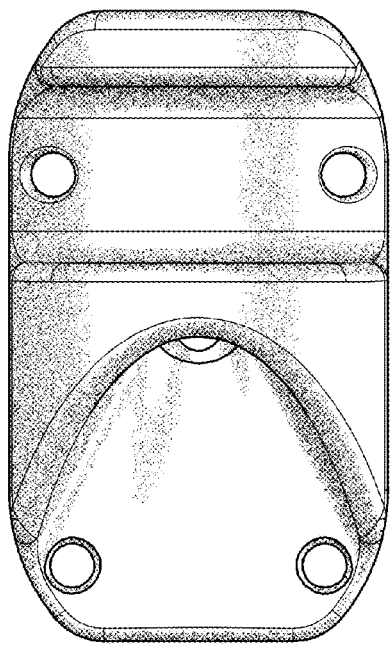
FIG. 23D is a top plan view thereof.
Figure 23E:
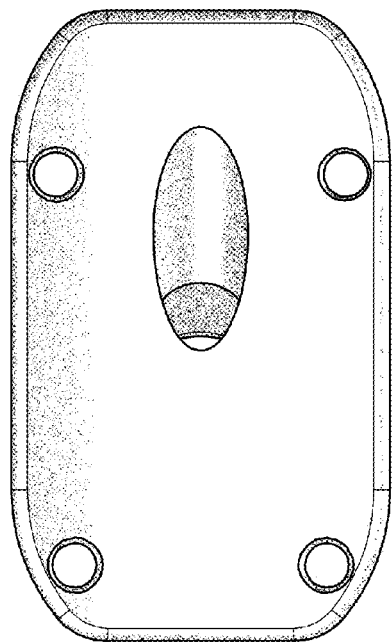
FIG. 23E is a bottom plan view thereof.
Figure 23F:
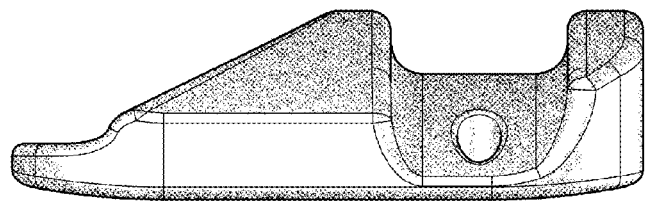
FIG. 23F is a right side elevation view thereof, wherein a left side elevation view is a mirror image of the right side elevation view.
Figure 23G:
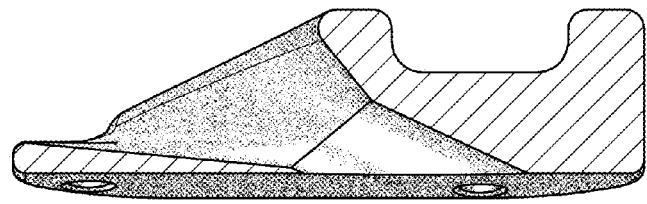
FIG. 23G is a cross-sectional view thereof.
Figure 24A:
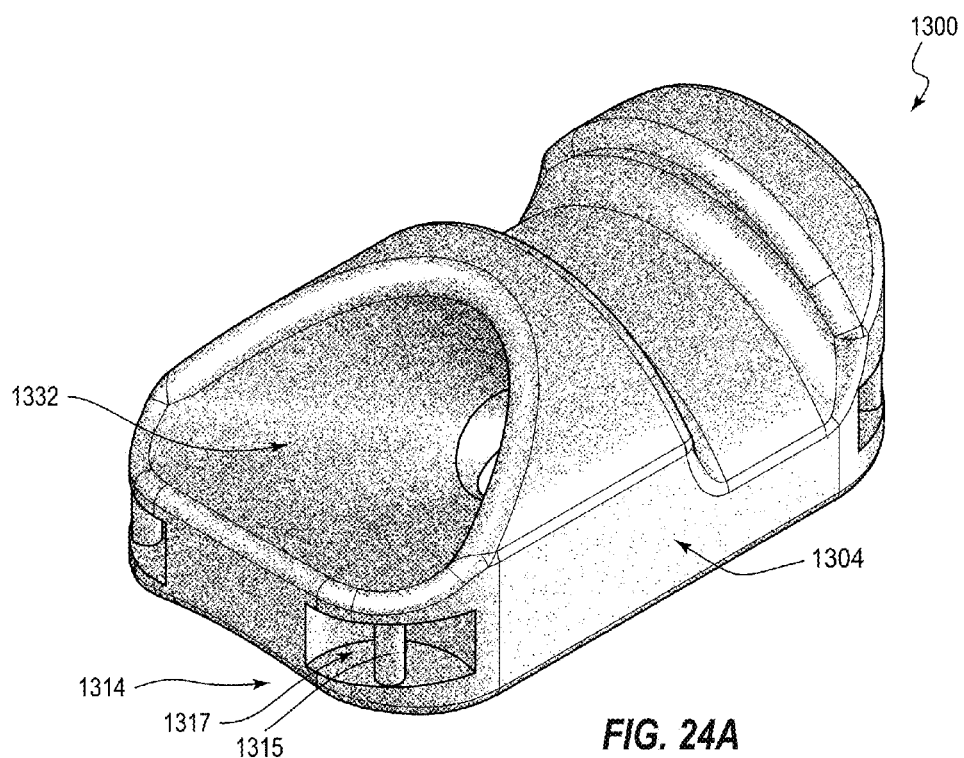
FIG. 24A is a perspective view of another embodiment of a vascular access port.
Figure 24B:
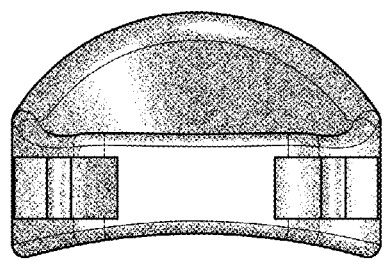
FIG. 24B is a rear elevation view thereof.
Figure 24C:
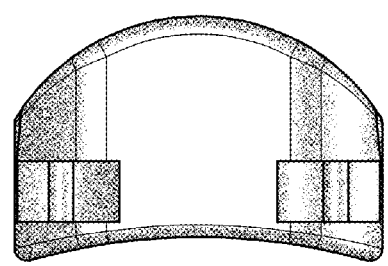
FIG. 24C is a front elevation view thereof.
Figure 24D:
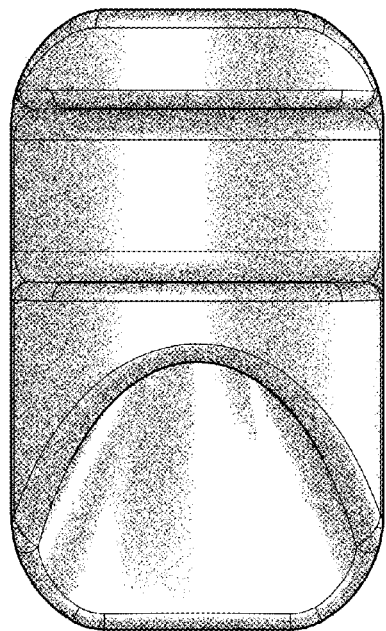
FIG. 24D is a top plan view thereof.
Figure 24E:
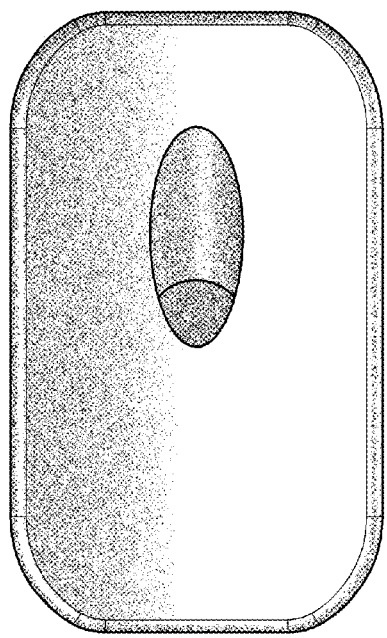
FIG. 24E is a bottom plan view thereof.
Figure 24F:
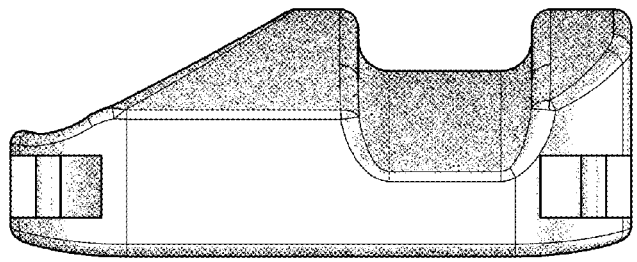
FIG. 24F is a right side elevation view thereof, wherein a left side elevation view is a mirror image of the right side elevation view.
Figure 24G:
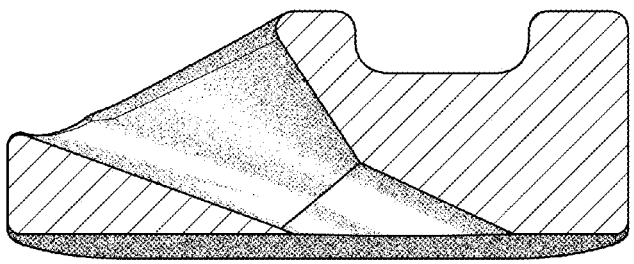
FIG. 24G is a cross-sectional view thereof.
Figure 25A:
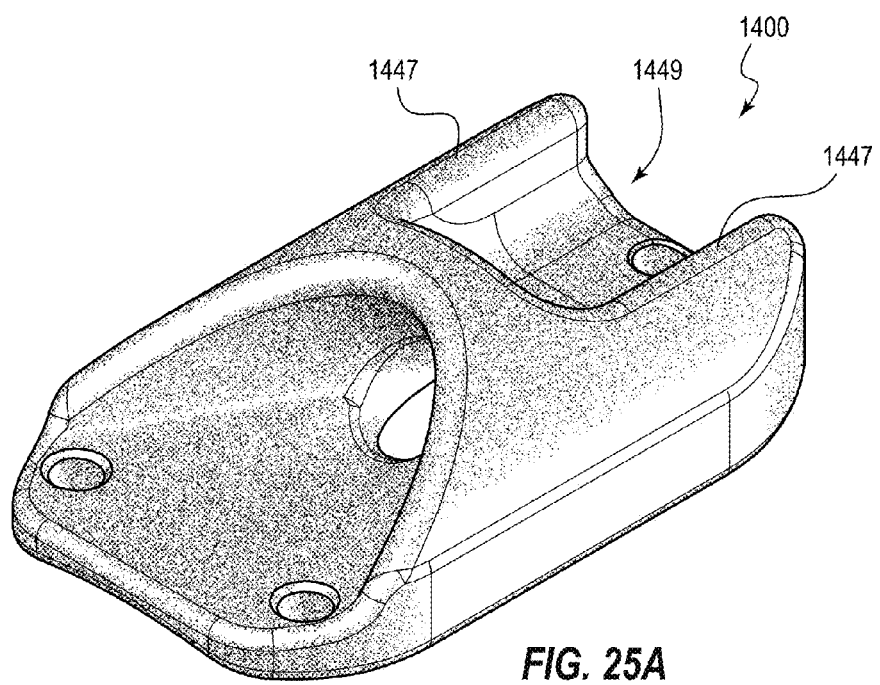
FIG. 25A is a perspective view of another embodiment of a vascular access port.
Figure 25B:
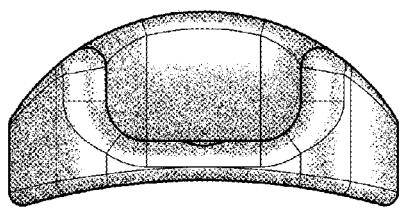
FIG. 25B is a rear elevation view thereof.
Figure 25C:
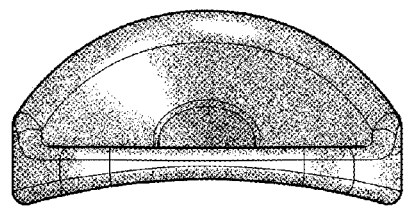
FIG. 25C is a front elevation view thereof.
Figure 25D:
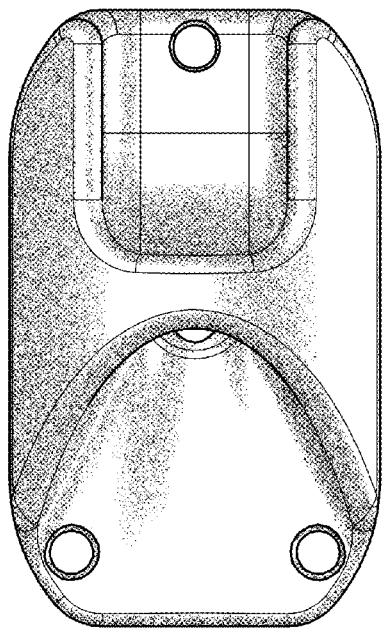
FIG. 25D is a top plan view thereof.
Figure 25E:
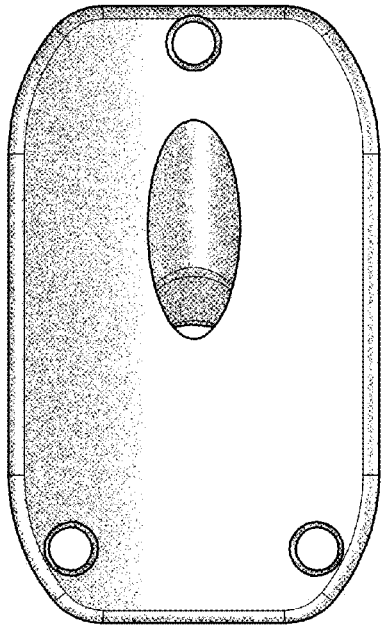
FIG. 25E is a bottom plan view thereof.
Figure 25F:
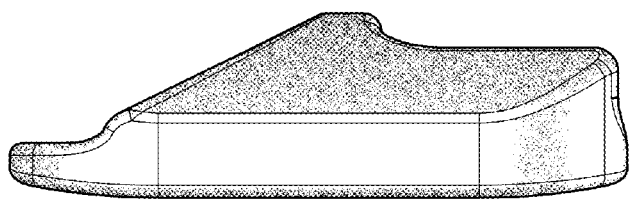
FIG. 25F is a right side elevation view thereof, wherein a left side elevation view is a mirror image of the right side elevation view.
Figure 25G:
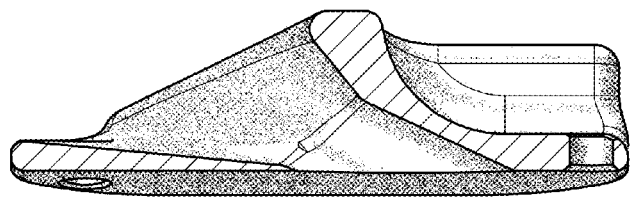
FIG. 25G is a cross-sectional view thereof.
Figure 26A:
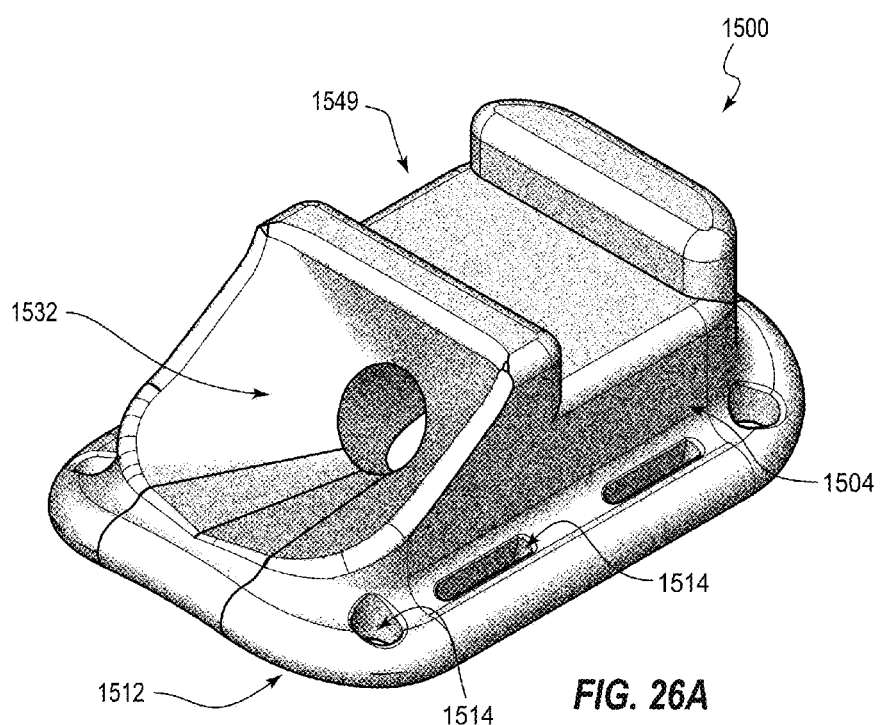
FIG. 26A is a perspective view of another embodiment of a vascular access port.
Figure 26B:
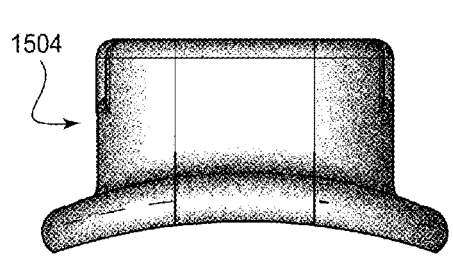
FIG. 26B is a rear elevation view thereof.
Figure 26C:
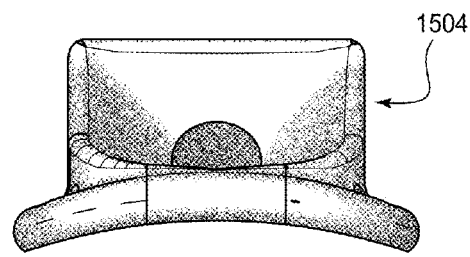
FIG. 26C is a front elevation view thereof.
Figure 26D:
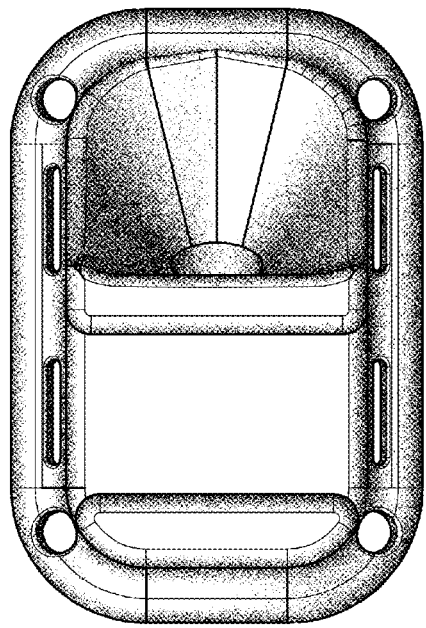
FIG. 26D is a top plan view thereof.
Figure 26E:
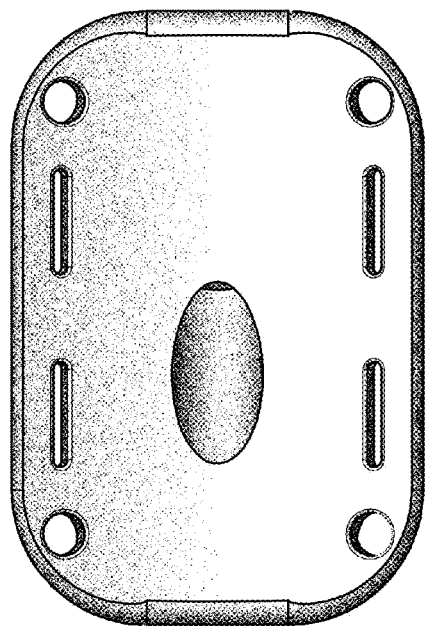
FIG. 26E is a bottom plan view thereof.
Figure 26F:
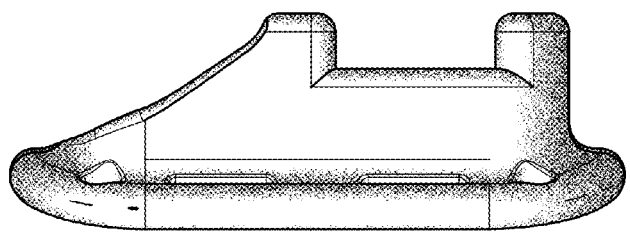
FIG. 26F is a right side elevation view thereof, wherein a left side elevation view is a mirror image of the right side elevation view.
Figure 26G:
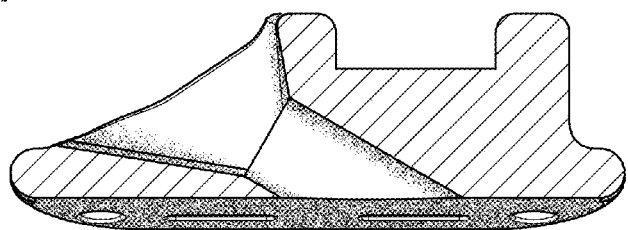
FIG. 26G is a cross-sectional view thereof.

FIGS. 22A-22G illustrate another embodiment of a vascular access port 1100, which can resemble the vascular access ports described above in certain respects. As shown in FIG. 22F, the port 1100 can comprise a palpation projection 1146 that is non-planar (i.e., that is not substantially planar).

FIGS. 23A-23G illustrate another embodiment of a vascular access port 1200, which can resemble the vascular access ports described above in certain respects. The port 1200 can include a body 1204 having an upper surface that is bowed in the transverse direction.

The port 1200 can include a palpation projection 1246 that borders a funnel region 1232. The palpation projection 1246 can comprise a radiused edge that protrudes very little from a body 1204 of the port 1200. The port 1200 can further comprise a supplemental palpation projection 1247, which is positioned at the forward end of the illustrated embodiment. The palpation projection 1247 can comprise a rounded protrusion that extends upwardly and in a transverse direction, and can be spaced from the funnel region 1232 by a recess 1249.

The port 1200 can include a plurality of attachment passages 1214. In the illustrated embodiment, the attachment passages 1214 extend through a bottom surface 1208 of the port 1200 within the recess 1249 and within the funnel region 1232.

FIGS. 24A-24G illustrate another embodiment of a vascular access port 1300, which can resemble the vascular access ports described above in certain respects. The port 1300 can particularly resemble the port 1200, but can include attachment passages 1314 that do not extend through a bottom surface 1308 of the port 1300. Rather, the attachment passages 1314 comprise vertical posts 1315 and recesses 1317 that extend into a body 1304 of the port 1300. The attachment passages 1314 can add height to the port 1300, as compared with the port 1200. However, the attachment passages 1314 also are spaced from and are beneath a funnel region 1332. Such an arrangement can avoid inadvertent insertion, or attempt at insertion, of an access device 144 into a vessel through an attachment passage 1314.

FIGS. 25A-25G illustrate another embodiment of a vascular access port 1400, which can resemble the vascular access ports described above in certain respects. The port 1400 can particularly resemble the port 1200, but can include supplemental palpation projections 1447 at a forward end that extend in a longitudinal direction. The palpation projections 1447 can be spaced from each other by a recess 1449.

FIGS. 26A-26G illustrate another embodiment of a vascular access port 1500, which can resemble the vascular access ports described above in certain respects. The port 1500 can particularly resemble the port 1200, but can include a body 1504 that defines a substantially rectangular profile as viewed from the front or rear. Additionally, the port 1500 can include a connection flange 1512 that fully encompasses the body 1504. The connection flange 1512 can include a plurality of attachment passages 1514 that pass therethrough. The attachment passages 1514 thus do not pass through a funnel region 1532 or a recess 1549.

FIG. 27A illustrates another embodiment of a vascular access port 1600, which can resemble the vascular access ports described above in certain respects. The port 1600 can include a base 1602 that comprises a graft extension 1605, which can aid in securely attaching the port 1600 to a vessel. In the illustrated embodiment, the graft extension 1605 can be fixedly attached to a remainder of the base 1602 via one or more sutures 116. Any other suitable method for attaching the graft extension 1605 to the base 1602 may be used. The graft extension 1605 can comprise any suitable material, which may be flexible so as to permit natural fluctuations in the vessel diameter. The material may also promote tissue ingrowth. In some embodiments, the graft extension 1605 comprises e-PTFE. In the illustrated embodiment, a first side of the graft extension 1605 (not shown) is coupled with the port 1600 and a second side 1609 is unattached thereto.

As shown in FIG. 27B, the graft extension 1605 can be positioned about a at least a portion of a vessel 200 and one or more attachment devices 116 can be inserted through the port 1600, through the various layers of the vessel 200, and through the graft extension 1605 and then secured (e.g., tied off). Additional attachment devices 116 may also be used relative to the port 1600 in manners such as discussed above.

In some embodiments, the vascular access port 1600 can be used to repair a fistula. For example, in some embodiments, the base 1602 (e.g., the graft extension 1605) can be positioned about an aneurism in a vessel wall.

In certain embodiments, the graft extension 1605 may be replaced with a housing element (not shown) that is configured to encompass at least a portion of the vessel 200 in a manner such as that depicted in FIG. 27B. The housing element can comprise any suitable biocompatible material, and may be sufficiently rigid to prevent an access device 144 from striking through a side of a vessel that is opposite the port 1600.

In various embodiments, at least a portion of the graft extension 1605 or the housing element can include a covering (not shown), such as a coating and/or an embedded portion, that comprises one or more materials or agents that provide antiseptic, antimicrobial, antibiotic, antiviral, antifungal, anti-infection, or other desirable properties to the vascular access port 1600, such as the ability to inhibit, decrease, or eliminate the growth of microorganisms at or near a surface of the port. For example, any suitable covering material listed above may be used.

Figure 28:
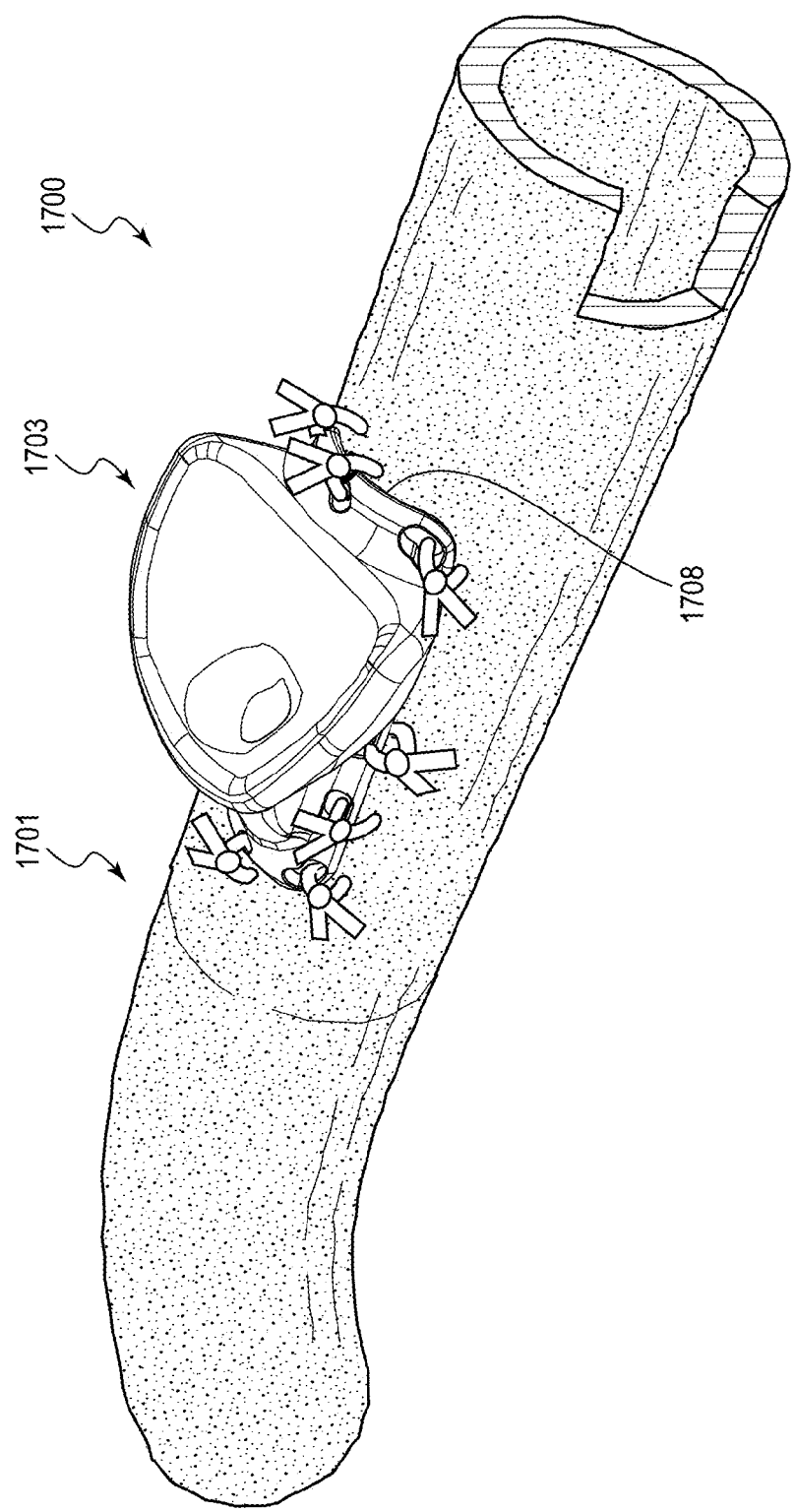
FIG. 28 is a perspective view of an embodiment of a vascular access system.

FIG. 28 illustrates an embodiment of a vascular access system 1700. The system 1700 includes an artificial graft vessel 1701 and a vascular access port 1703 attached thereto. The vascular access port 1703 can resemble any of the access ports described above. However, in some embodiments, a bottom surface 1708 of the port 1703 may be devoid of an ingrowth-inducing covering. The bottom surface 1708 may be provided with an adhesive to create a tight bond between the port 1703 and the graft vessel 1701. In some embodiments, a fluid-tight seal is provided between the port 1703 and the graft vessel 1701, which can prevent blood or other fluids from seeping between the port 1703 and the graft vessel 1701 during or after an access event. One or more attachment devices 116 may be used to attach the port 1703 to the graft vessel 1701. The graft vessel 1701 can comprise any suitable material, such as, for example, e-PTFE.

Figure 29:
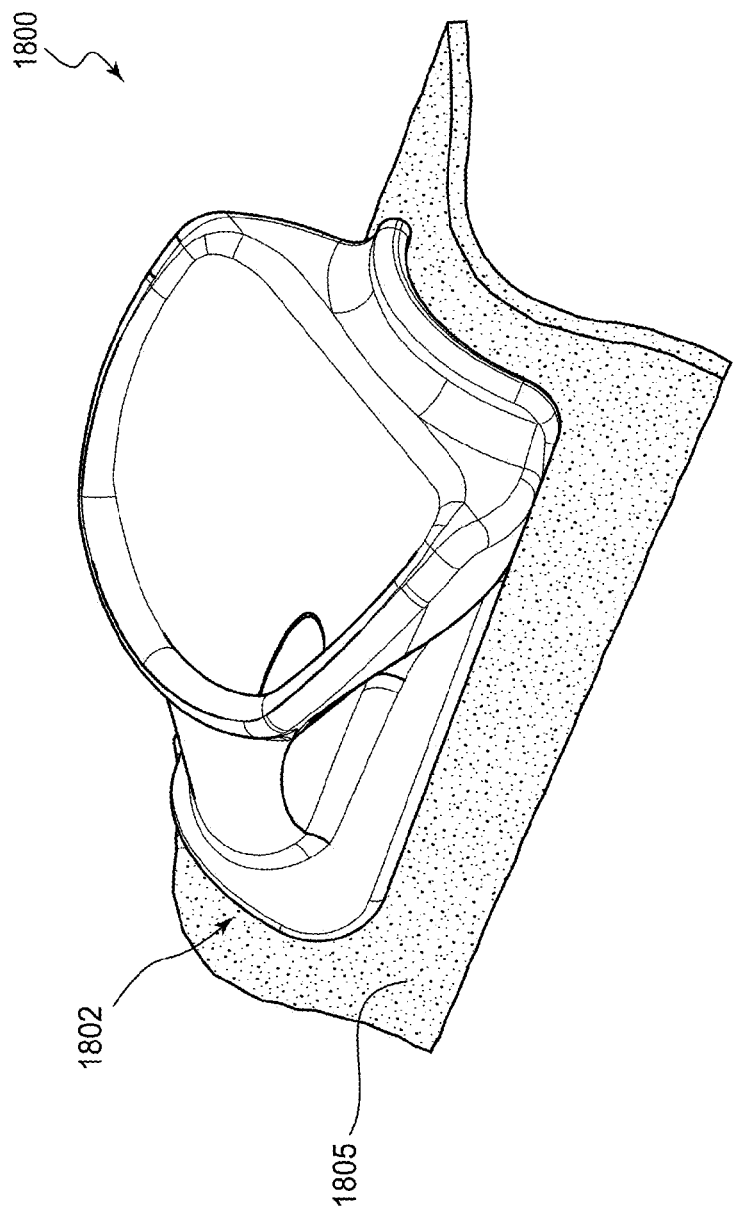
FIG. 29 is a perspective view of another embodiment of a vascular access port.

FIG. 29 illustrates another embodiment of a vascular access port 1800. The vascular access port 1800 includes a flexible patch 1805 connected to a base 1802 thereof. The patch 1805 extends outwardly beyond a periphery of the body 1802. The patch 1805 can comprise any suitable biocompatible material, and can promote tissue ingrowth therein. For example, in various embodiments, the patch 1805 comprises one or more of Dacron, e-PTFE, or polyurethane foam. The patch 1805 can be conformable to an exterior surface of a vessel to which it is attached, and it may be attached to the vessel by one or more of sutures, clips, or other suitable devices. The patch 1805 can be configured to encompass at least a portion of the vessel to which it is attached.

Figure 30:
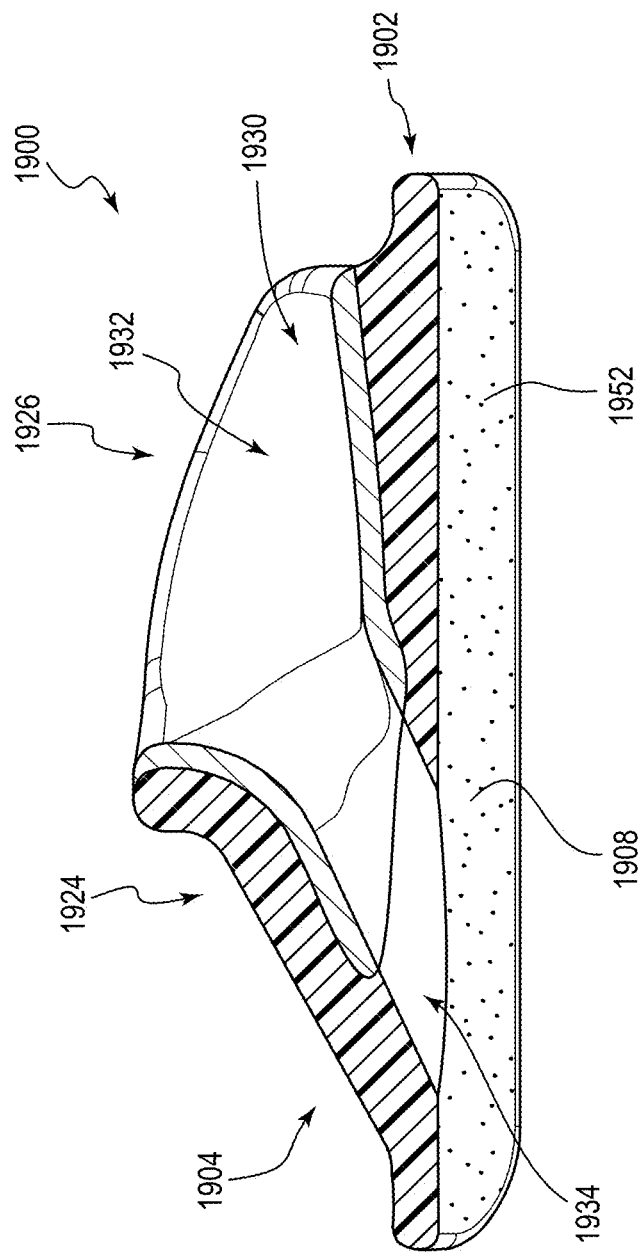
FIG. 30 is a cross-sectional view of another embodiment of a vascular access port.

FIG. 30 illustrates another embodiment of a vascular access port 1900. The vascular access port 1900 includes a supportive component 1924 and a directive component 1926 that have different properties, such as, for example, different resistances to puncturing, duration times once implanted in a patient, or material costs. In various embodiments, each of the supportive and directive components 1924, 1926 can form at least a portion of one or more of a base 1902 and a body 1904 of the vascular access port 1900. For example, in the illustrated embodiment, each of the supportive and directive components 1924, 1926 help form the body 1904, whereas, of the two, only the supportive component 1924 contributes to the base 1902.

In some embodiments, the supportive and directive components 1924, 1926 are configured to maintain a predetermined form within a patient for different periods of time once the vascular access port 1900 has been implanted. For example, in some embodiments, the supportive component 1924 is configured to be resorbed within a patient more quickly than is the directive component 1926. For example, in various embodiments, the supportive component 1924 is resorbed at a rate that is no more that about 1.5, 2, 3, 4, 5, 6, 7, 8, 9, or 10 times the rate at which the directive component 1926 is resorbed, or the supportive component 1924 is resorbed at a rate that is no less than about 1.5, 2, 3, 4, 5, 6, 7, 8, 9, or 10 times the rate at which the directive component 1926 is resorbed. In some embodiments, the directive component 1926 is configured to resist resorption, and may remain within a patient indefinitely without being resorbed. In some embodiments, the supportive component is configure to be fully resorbed within a period of no more than about 1, 2, 3, 4, 5, or 6 months or no less than about 1, 2, 3, 4, 5, or 6 months.

In various embodiments, one or both of the supportive and directive components 1924, 1926 can comprise a resorbable material, such as, for example, any suitable resorbable material described above. In other or further embodiments, the directive component 1926 can comprise a non-resorbable material, such as stainless steel, titanium, or the like.

A substantial portion of a guidance passageway 1930 can be defined by the directive component 1926. For example, in the illustrated embodiment, an entire funnel region 1932 and an entrance end of a channel 1934 are formed by the directive component 1926. In contrast, only an exit end of the channel 1934 is formed by the supportive component 1924. As it is more resistant to being resorbed, the directive component 1926 can resist coring and scraping by a needle or other insertion device 144 for a longer duration, and thus can assist in creating an insertion tract through the skin of a patient to a buttonhole, and in the creation of the buttonhole itself.

The supportive component 1924 can encompass a forward end of the directive component 1926, as shown. The supportive and directive components 1924, 1926 can be joined to each other in any suitable manner. For example, the components 1924, 1926 can be adhered or welded to each other. In some embodiments, the supportive component 1924 is overmolded onto the directive component 1926.

Tissue that replaces the supportive component 1924 can in turn support the directive component 1926 in a similar manner such that the directive component 1926 can generally maintain the same orientation within a patient. In some embodiments, an outer surface of the directive component 1926 (e.g., a surface opposite the guidance passageway 1930) can include an ingrowth-inducing covering such as the covering 152 described above. Accordingly, as the supportive component 1924 is replaced with tissue, the tissue can be firmly attached to the directive component. Additionally, as with the ports discussed above, at least a bottom surface 1908 of the vascular access port 1900 can include an ingrowth-inducing covering 1952.

In some embodiments, different materials may be used for the supportive and directive components 1924, 1926 as a cost-saving measure. For example, a less durable, less expensive material may be used for the supportive component 1924 with little or no difference in the performance of certain embodiments of vascular access ports described above. In some embodiments, the directive component 1926 may comprise a coating or layer of a material having intrinsic strength and/or that is capable of imparting strength to the supportive component 1924.

FIG. 31 illustrates an embodiment of a system 2000 configured for the external treatment of blood. The system 2000 is similar to the system 300 described above. The system 2000 includes two vascular access ports 100A, 100B, which can resemble any of the ports described above. Both of the ports 100A, 100B are shown attached to a vessel 200 that is associated with an arteriovenous fistula 218. One port 100A is directed upstream such that a forward end thereof points in a direction opposite to the flow of blood through the vessel 200, and the other port 100B is directed downstream such that a forward end thereof points in the direction of the blood flow through the vessel 200, although other arrangements are possible. A separate access device 144 (e.g., fistula needle or over-the-needle catheter) may be introduced into each of the ports 100A, 100B via any of the methods described above and connected to a blood treatment system 2002 (e.g., hemodialysis machine) via any suitable passageways 2004 (e.g., tubing).

Blood treatment then can then be performed. The first port 100A can be an uptake port through which blood is removed from the vessel 200 and delivered to the blood treatment system 2002, and the second port 100B can be a return port through which treated blood is returned to the vessel 200 from the blood treatment system 2002. Accordingly, in use, blood is removed from the patient via an access device 144 that is within the first port 100A and delivered to the blood treatment system 2002. The removed blood is treated in any suitable manner via the blood treatment system 2002. Treated blood is returned to the patient via an access device 144 that is within the second port 100B.

In other embodiments, the system 2000 can comprise only a single vascular access port 100A or 100B. Blood treatment may be conducted thereby via any suitable method (e.g., a single-needle hemodialysis technique). In still other embodiments, the system 2000 includes more than two vascular access ports 100A, 100B. A clinician thus can rotate among the ports 100A, 100B, thereby leaving one or more of the ports unused during any given blood treatment session.

As can be appreciated from the foregoing, embodiments of vascular access ports can be sized and dimensioned to reside within a patient and beneath an outer surface of the skin of the patient. For example, the vascular access ports can be sized to fit between a vessel (e.g., any suitable artery or vein, such as, for example, the cephalic, basilic, femoral, jugular, or subclavian vein) and the epidermis of an animal subject.

Moreover, embodiments of one or more vascular access ports can be included in various embodiments of kits. For example, in some embodiments, a kit can comprise a vascular access port such as any of the ports described above. The kit can further include one or more of: one or more sutures or other attachment devices by which the port can be attached to a vessel, one or more synthetic grafts (which may be pre-attached to the port or separate therefrom), one or more pads of ingrowth-inducing material (which may be pre-attached to the port or separate therefrom), and one or more additional vascular access ports of the same configuration and/or of one or more different configurations (e.g., different size, shape, etc.). For example, in some embodiments, the kit can include multiple ports such that a practitioner can select one or more of the ports for implantation. In further embodiments, the kit can include ports of different sizes such that the practitioner can further select an appropriate port (or appropriate ports) based on the particular anatomy of a patient and/or on the target location of the port (or ports).

It is noted that while many of the examples provided herein relate to the use of vascular access ports with blood vessels, this method of disclosure is employed for the sake of convenience and efficiency, but should not be construed as limiting of the types of procedures with which embodiments may be used. Indeed, embodiments of the apparatus, methods, and systems disclosed herein can be used with vessels other than blood vessels, such as, for example, vessels within the gastrointestinal tract. Accordingly, the term "vessel" is a broad term that can include any hollow or walled organ or structure of a living organism, whether natural or synthetic.

It will be understood by those having skill in the art that changes may be made to the details of the above-described embodiments without departing from the underlying principles presented herein. For example, any suitable combination of various embodiments, or the features thereof, is contemplated.

Likewise, although symmetries are present in the illustrated embodiments, some embodiments may be asymmetrical. For example in some embodiments, a guidance passageway of a vascular access port may extend generally at an angle relative to a vertical longitudinal plane through the port such that a funnel region may more readily receive an access device therein at one side of the port as opposed to an opposite side thereof. Such arrangements may be beneficial in some applications where a port is implanted on a vessel that may more easily be reached from a direction that is not generally aligned with (e.g., nonparallel to) the vessel.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the terms "about" or "approximately." For each such reference, it is to be understood that, in some embodiments, the value, feature, or characteristic may be specified without approximation. For example, although it is noted that in various embodiments, the height H of the vascular access port 100 is no greater than about 2, 3, 4, 5, 6, 7, 8, 9, 10, 11, 12, 13, 14, or 15 millimeters, it is understood that in some embodiments, the height H of the vascular access port 100 is no greater than 2, 3, 4, 5, 6, 7, 8, 9, 10, 11, 12, 13, 14, or 15 millimeters.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements specifically recited in means-plus-function format, if any, are intended to be construed in accordance with 35 U.S.C. §112 ¶6.

Embodiments of the invention in which an exclusive property or privilege is claimed are defined as follows:

1. A vascular access port comprising:
   a base that extends between a front end and a back end in a longitudinal direction and that comprises an opening;
   a guidance passageway that extends from an entry mouth at a proximal end thereof to the opening of the base, wherein the guidance passageway comprises a funnel region that decreases in size in a distal direction, wherein the entry mouth is open to permit one or more needles to be inserted individually through the guidance passageway and is configured to be positioned beneath a surface of the skin of a patient when the vascular access port has been implanted in the patient, wherein a central axis that extends through the guidance passageway defines an acute angle relative to a longitudinal length of the base, and wherein the acute angle points in a forward direction; and
   an ingrowth-inducing covering on the base that is configured to promote attachment of the vascular access port to the vessel so as to maintain the opening of the port at a fixed position relative to a wall of the vessel, wherein at least a portion of the ingrowth-inducing covering is forward of the opening of the base and is rearward of the front end of the base, and wherein the guidance passageway is configured to direct the one or more needles that are inserted individually through the guidance passageway to an insertion site of the vessel that is rearward of the front end of the base when the vascular access port is attached to the vessel.

2. The vascular access port of claim 1, wherein the base is configured to be bowed in a transverse direction that is perpendicular to the longitudinal direction when the vascular access port is attached to a vessel so as to conform to a contour of a wall of the vessel, and wherein the longitudinal direction of the base is configured to run substantially parallel to a lumen of the vessel when the vascular access port is attached to the vessel.

3. The vascular access port of claim 1, wherein the base comprises a bottom surface that is configured to face the vessel when the vascular access port is coupled to the vessel, and wherein the bottom surface comprises the opening.

4. The vascular access port of claim 1, wherein the ingrowth-inducing covering encompasses the opening of the guidance passageway.

5. The vascular access port of claim 1, further comprising a flange that at least partially encompasses the opening of the guidance passageway, wherein the flange comprises one or more attachment passages through which one or more attachment members can extend so as to attach the vascular access port to a vessel.

6. The vascular access port of claim 5, wherein the flange comprises an attachment passage at the front end of the vascular access port.

7. The vascular access port of claim 5, wherein the flange comprises a plurality of attachment passages that extend through the base, and wherein the attachment passages define a perimeter of an attachment area that is covered by the ingrowth-inducing covering.

8. The vascular access port of claim 7, wherein the guidance passageway opening is within the attachment area.

9. The vascular access port of claim 1, wherein the ingrowth-inducing covering is constrained to a bottom surface of the base of the vascular access port and an upper portion of the vascular access port is smooth so as to discourage ingrowth of fascia at the upper portion of the vascular access port.

10. The vascular access port of claim 1, wherein the ingrowth-inducing covering comprises a plurality of titanium beads that have an average diameter of no greater than about 5 thousandths of an inch.

11. The vascular access port of claim 1, wherein a height of the vascular access port is no less than about 0.5 times a width of the base.

12. The vascular access port of claim 1, wherein the acute angle between the central axis of the guidance passageway and the longitudinal length of the base is no greater than about 60 degrees.

13. The vascular access port of claim 1, further comprising a graft extension, a housing, or a patch configured to encompass at least a portion of a vessel in order to secure the vascular access port to the vessel.

14. The vascular access port of claim 1, wherein a portion of the vascular access port that is configured to be attached to the vessel comprises a first resorbable material.

15. The vascular access port of claim 14, wherein the guidance passageway comprises a non-resorbable material or a second resorbable material that has a slower resorption rate than the first resorbable material.

16. A vascular access port comprising:
a base that extends between a front end and a back end in a longitudinal direction and that comprises an opening;
a guidance passageway that extends from an entry mouth at a proximal end thereof to the opening of the base, wherein the guidance passageway comprises a funnel region that decreases in size in a distal direction, wherein the entry mouth is open to permit one or more needles to be inserted individually through the guidance passageway and is configured to be positioned beneath a surface of the skin of a patient when the vascular access port has been implanted in the patient, wherein a central axis that extends through the guidance passageway defines an acute angle relative to a longitudinal length of the base, and wherein the acute angle points in a forward direction; and
an attachment passage extending through the base at a position forward of the opening of the base, wherein the attachment passage is configured to permit an attachment device to pass therethrough to connect the vascular access port to the vessel so as to resist forward movement of the vascular access port relative the vessel as the one or more needles are inserted individually through the guidance passageway, and wherein the guidance passageway is configured to direct the one or more needles that are inserted individually through the guidance passageway to an insertion site of the vessel that is rearward of the front end of the base when the vascular access port is attached to the vessel.

17. The vascular access port of claim 16, wherein the base is configured to be bowed in a transverse direction that is perpendicular to the longitudinal direction when the vascular access port is attached to a vessel so as to conform to a contour of a wall of the vessel, and wherein the longitudinal direction of the base is configured to run substantially parallel to a lumen of the vessel when the vascular access port is attached to the vessel.

18. The vascular access port of claim 16, wherein the base comprises a bottom surface that is configured to face the vessel when the vascular access port is coupled to the vessel, and wherein the bottom surface comprises the opening.

19. The vascular access port of claim 16, wherein the attachment device comprises one of a suture, a pinch ring, a hook, and a wire.

20. The vascular access port of claim 16, further comprising an additional attachment passage at a rearward end of the vascular access port.

21. A kit comprising:
the vascular access port of claim 16; and
one or more of a suture, a synthetic graft, and one or more additional vascular access ports.

\* \* \* \* \*